United States Patent
BenMohamed

(10) Patent No.: US 11,213,582 B2
(45) Date of Patent: Jan. 4, 2022

(54) PROTECTION AGAINST RECURRENT GENITAL HERPES BY THERAPEUTIC IMMUNIZATION WITH HERPES SIMPLEX VIRUS TYPE 2 RIBONUCLEOTIDE REDUCTASE PROTEIN SUBUNITS

(71) Applicant: THE REGENTS OF THE UNIVERSITY OF CALIFORNIA, Oakland, CA (US)

(72) Inventor: Lbachir BenMohamed, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/535,534

(22) Filed: Aug. 8, 2019

(65) Prior Publication Data
US 2020/0046827 A1 Feb. 13, 2020

Related U.S. Application Data

(60) Provisional application No. 62/786,617, filed on Dec. 31, 2018, provisional application No. 62/716,347, filed on Aug. 8, 2018.

(51) Int. Cl.
| | | |
|---|---|---|
| A61K 39/245 | (2006.01) | |
| A61P 31/22 | (2006.01) | |
| C12N 7/00 | (2006.01) | |
| A61K 39/00 | (2006.01) | |

(52) U.S. Cl.
CPC ............ A61K 39/245 (2013.01); A61P 31/22 (2018.01); C12N 7/00 (2013.01); A61K 2039/545 (2013.01); A61K 2039/55516 (2013.01); A61K 2039/55522 (2013.01); A61K 2039/55561 (2013.01); C12N 2710/16634 (2013.01); C12N 2710/16671 (2013.01)

(58) Field of Classification Search
CPC ............ A61K 39/245; A61K 2039/545; A61K 2039/55522; A61K 2039/55516; 2039/55561; A61K 2039/575; A61K 2039/57; A61K 39/12; A61P 31/22; C12N 7/00; C12N 2710/16634; C12N 2710/16671; C12N 2710/16622; C07K 14/005
See application file for complete search history.

(56) References Cited

U.S. PATENT DOCUMENTS

| | | | |
|---|---|---|---|
| 8,546,337 B2 * | 10/2013 | Burkhard | A61K 39/015 514/21.3 |
| 8,575,110 B2 | 11/2013 | Burkhard | |
| 10,245,318 B2 | 4/2019 | Burkhard | |
| 2013/0224236 A1 * | 8/2013 | Koelle | A61K 39/12 424/186.1 |
| 2014/0127247 A1 * | 5/2014 | Dubensky, Jr. | A61K 39/245 424/186.1 |
| 2014/0227307 A1 * | 8/2014 | Long | A61P 31/22 424/186.1 |
| 2017/0216428 A1 * | 8/2017 | Truneh | A61P 37/04 |

FOREIGN PATENT DOCUMENTS

| | | |
|---|---|---|
| WO | 2018154010 | 8/2018 |
| WO | 2018172447 | 9/2018 |

OTHER PUBLICATIONS

Hensel MT, Marshall JD, Dorwart MR, Heeke DS, Rao E, Tummala P, Yu L, Cohen GH, Eisenberg RJ, Sloan DD. J Virol. Apr. 13, 2017;91(9). pii: e02257-16. Print May 1, 2017.*

Xu F, Schillinger JA, Sternberg MR, et al. Seroprevalence and coinfection with herpes simplex virus type 1 and type 2 in the United States, 1988-1994. J Infect Dis. 2002;185(8):1019-1024.*

Shin H, Iwasaki A. A vaccine strategy that protects against genital herpes by establishing local memory T cells. Nature. 2012;491(7424):463-467.*

Gong, A., Lipton, S. & Brunell, P. Does Live Varicella Vaccine (LVV) Protect Against Other Herpesviruses?. Pediatr Res 21, 325 (1987). (Year: 1987).*

Salvucci LA, Bonneau RH, Tevethia SS. Polymorphism within the herpes simplex virus (HSV) ribonucleotide reductase large subunit (ICP6) confers type specificity for recognition by HSV type 1-specific cytotoxic T lymphocytes. J Virol. Feb. 1995;69(2):1122-31. (Year: 1995).*

Van Velzen M, Jing L, Osterhaus AD, Sette A, Koelle DM, Verjans GM. Local CD4 and CD8 T-cell reactivity to HSV-1 antigens documents broad viral protein expression and immune competence in latently infected human trigeminal ganglia. PLoS Pathog. Aug. 2013;9(8):e1003547. Epub Aug. 15, 2013. (Year: 2013).*

Dasgupta G, Chentoufi AA, et al. Immunodominant "asymptomatic" herpes simplex virus 1 and 2 protein antigens identified by probing whole-ORFome microarrays with serum antibodies from seropositive asymptomatic versus symptomatic individuals. J Virol. Apr. 2012;86(8):4358-69. Epub Feb. 8, 2012. (Year: 2012).*

Belshe et al., 2012, "Efficacy Results of a Trial of a Herpes Simplex Vaccine," The New England journal of medicine, 366:34-43.

Johnston et al., 2011, "HSV-2: in pursuit of a vaccine," J Clin Invest. 121(12):4600-9.

Kalantari-Dehaghi et al., 2012, "Discovery of potential diagnostic and vaccine antigens in herpes simplex virus 1 and 2 by proteome-wide antibody profiling," J Virol. 2012;86(8):4328-39.

Long et al., 2014, "Identification of novel virus-specific antigens by CD4☐ and CD☐ T cells from asymptomatic HSV-2 seropositive and seronegative donors," Virology, 464-465.

(Continued)

*Primary Examiner* — Rachel B Gill
(74) *Attorney, Agent, or Firm* — Riverside Law LLP

(57) ABSTRACT

The present invention relates to compositions comprising HSV antigens and methods for their use in the treatment or prevention of asymptomatic and symptomatic herpesvirus infection, or recurrence.

12 Claims, 58 Drawing Sheets
Specification includes a Sequence Listing.

(56) References Cited

OTHER PUBLICATIONS

Peng et al., 2012, "An effector phenotype of CD8+ T cells at the junction epithelium during clinical quiescence of herpes simplex virus 2 infection," J Virol, 86(19):10587-96.
Zhu et al., 2007, "Virus-specific CD8+ T cells accumulate near sensory nerve endings in genital skin during subclinical HSV-2 reactivation," J Exp Med, 204(3):595-603.
Zhu et al., 2013, "Immune surveillance by CD8αα+ skin-resident T cells in human herpes virus infection," Nature. 2013;497(7450):494-7.
Awasthi et al., 2014, "Blocking herpes simplex virus 2 glycoprotein E immune evasion as an approach to enhance efficacy of a trivalent subunit antigen vaccine for genital herpes," J Virol, 88(15):8421-32.
Awasthi et al., 2014, "Protection provided by a herpes simplex virus 2 (HSV-2) glycoprotein C and D subunit antigen vaccine against genital HSV-2 infection in HSV-1-seropositive guinea pigs," J Virol, 88(4):2000-10.
Awasthi et al., 2011, "Immunization with a vaccine combining herpes simplex virus 2 (HSV-2) glycoprotein C (gC) and gD subunits improves the protection of dorsal root ganglia in mice and reduces the frequency of recurrent vaginal shedding of HSV-2 DNA in guinea pigs compared to immunization with gD alone," J Virol, 85(20):10472-86.
Thornton et al., 1984, "Herpes simplex virus genital infection of the female guinea pig as a model for the evaluation of an experimental vaccine," Vaccine, 2(2):141-8.
Veselenak et al., 2018, "Transcriptional Analysis of the Guinea Pig Mucosal Immune Response to Intravaginal Infection with Herpes Simplex Virus Type 2," Virology, 518:349-57.
Perry et al., 2016, "Detection of herpes simplex virus type 2 (HSV-2)-specific cell-mediated immune responses in guinea pigs during latent HSV-2 genital infection," J Immunol Methods, 439:1-7.
Xia et al., 2014, "Virus-specific immune memory at peripheral sites of herpes simplex virus type 2 (HSV-2) infection in guinea pigs," PloS one, 9(12):e114652, 22 pages.
Samandary et al., 2014, "Associations of HLA-A, HLA-B and HLA-C alleles frequency with prevalence of herpes simplex virus infections and diseases across global populations: implication for the development of an universal CD8+ T-cell epitope-based vaccine," Hum Immunol, 75(8):715-29.
Looker et al., 2008, "An estimate of the global prevalence and incidence of herpes simplex virus type 2 infection," Bull World Health Organ, 86(10):805-12.
Prodhan et al., 2010, "Neonatal herpes virus infection and extracorporeal life support," Pediatr Crit Care Med, 11(5):599-602.
Wald, 2006, "Genital HSV-1 infections," Sexually transmitted infections, 82(3):189-90.
Mertz et al., 2003, "Is herpes simplex virus type 1 (HSV-1) now more common than HSV-2 in first episodes of genital herpes?," Sex Transm Dis, 30(10):801-2.
Abu-Raddad et al., 2008, "Genital herpes has played a more important role than any other sexually transmitted infection in driving HIV prevalence in Africa," PloS one, 3(5):e2230, 15 pages.
Kuo et al., 2014, "The challenges and opportunities for the development of a T-cell epitope-based herpes simplex vaccine," Vaccine, 2014;32(50):6733-45.
Dasgupta and BenMohamed, 2011, "Of mice and not humans: how reliable are animal models for evaluation of herpes CD8(+)-T cell-epitopes-based immunotherapeutic vaccine candidates?" Vaccine, 29(35):5824-36.
Stanberry et al., 2002, "Glycoprotein-D-adjuvant vaccine to prevent genital herpes," N Engl J Med, 347(21):1652-61.
Van Wagoner et al., 2018, "Effects of Different Doses of GEN-003, a Therapeutic Vaccine for Genital Herpes Simplex Virus-2, on Viral Shedding and Lesions: Results of a Randomized Placebo-Controlled Trial," The Journal of infectious diseases, 218(12):1890-9.

Bernstein et al., 2017, "Therapeutic Vaccine for Genital Herpes Simplex Virus-2 Infection: Findings From a Randomized Trial," The Journal of infectious diseases, 215(6):856-64.
Flechtner et al., 2016, "Immune responses elicited by the GEN-003 candidate HSV-2 therapeutic vaccine in a randomized controlled dose-ranging phase 1/2a trial," Vaccine, 34(44):5314-20.
Freeman et al., 2007, "Psychological stress compromises CD8+ T cell control of latent herpes simplex virus type 1 infections," J Immunol, 179(1):322-8.
Horn et al, 2015, "Psychological distress, emotional stability, and emotion regulation moderate dynamics of herpes simplex virus type 2 recurrence," Ann Behav Med, 49(2):187-98.
Shirtcliff et al., 2009, "Early childhood stress is associated with elevated antibody levels to herpes simplex virus type 1," Proc Natl Acad Sci U S A, 106(8):2963-7.
Ortiz et al., 2003, "Stress-induced changes in pathophysiology and interferon gene expression during primary HSV-1 infection," Brain Behav Immun. 2003;17(5):329-38.
Dasgupta et al., 2009, "New concepts in herpes simplex virus vaccine development: notes from the battlefield," Expert Rev Vaccines, 8(8):1023-35.
Wald et al., 2006, "Comparative efficacy of famciclovir and valacyclovir for suppression of recurrent genital herpes and viral shedding," Sexually transmitted diseases, 33(9):529-33.
De Bruyn et al., 2006, "A randomized controlled trial of a replication defective (gH deletion) herpes simplex virus vaccine for the treatment of recurrent genital herpes among immunocompetent subjects," Vaccine. 2006;24(7):914-20.
Kriesel et al., 2005, "Recurrent antiviral-resistant genital herpes in an immunocompetent patient," The Journal of infectious diseases, 192(1): 156-61.
Zhang et al., 2012, "Targeting the genital tract mucosa with a lipopeptide/recombinant adenovirus prime/boost vaccine induces potent and long-lasting CD8+ T cell immunity against herpes: importance of MyD88," J Immunol, 189(9):4496-509.
Chentoufi et al., 2010, "A novel HLA (HLA-A*0201) transgenic rabbit model for preclinical evaluation of human CD8+ T cell epitope-based vaccines against ocular herpes," Journal of immunology, 184(5):2561-71.
Corey et al., 1999, "Recombinant glycoprotein vaccine for the prevention of genital HSV-2 infection: two randomized controlled trials. Chiron HSV Vaccine Study Group," Jama, 282(4):331-40.
Langenberg et al., 1999, "A prospective study of new infections with herpes simplex virus type 1 and type 2. Chiron HSV Vaccine Study Group," N Engl J Med, 341(19):1432-8.
Chentoufi et al., 2008, "HLA-A*0201-restricted CD8+ cytotoxic T lymphocyte epitopes identified from herpes simplex virus glycoprotein D," J Immunol, 180(1):426-37.
Tronstein et al., 2011, "Genital shedding of herpes simplex virus among symptomatic and asymptomatic persons with HSV-2 infection," JAMA, 305(14):1441-9.
Wald et al., 2000, "Reactivation of genital herpes simplex virus type 2 infection in asymptomatic seropositive persons," N Engl J Med, 342(12):844-50.
Rouse et al., 2006, "Regulatory T cells in virus infections," Immunological reviews, 212:272-86.
Cunningham et al., 2006, "The cycle of human herpes simplex virus infection: virus transport and immune control," The Journal of infectious diseases, 194 Suppl 1 :S11-8.
Koelle and Ghiasi, 2005, "Prospects for developing an effective vaccine against ocular herpes simplex virus infection," Curr Eye Res, 30(11):929-42.
Srivastava et al., 2015, "A Herpes Simplex Virus Type 1 Human Asymptomatic CD8+ T-Cell Epitopes-Based Vaccine Protects Against Ocular Herpes in a "Humanized" HLA Transgenic Rabbit Model," Invest Ophthalmol Vis Sci, 56(6):4013-28.
Khan et al., 2014, "Asymptomatic memory CD8+ T cells: from development and regulation to consideration for human vaccines and immunotherapeutics," Hum Vaccin Immunother, 10(4):945-63.
Dervillez et al., 2012, "Future of an "Asymptomatic" T-cell Epitope-Based Therapeutic Herpes Simplex Vaccine," Future virology, 7(4):371-8.

(56) References Cited

OTHER PUBLICATIONS

Chentoufi et al., 2012, "Towards a rational design of an asymptomatic clinical herpes vaccine: the old, the new, and the unknown," Clin Dev Immunol, 2012:187585, 16 pages.
Diaz et al., 2018, "Intramuscular delivery of replication-defective herpes simplex virus gives antigen expression in muscle syncytia and improved protection against pathogenic HSV-2 strains," Virology, 513:129-35.
Smith et al., 1998, "The PK domain of the large subunit of herpes simplex virus type 2 ribonucleotide reductase (ICP10) is required for immediate-early gene expression and virus growth," J Virol, 72(11):9131-41.
Hensel et al., 2017, "Prophylactic Herpes Simplex Virus 2 (HSV-2) Vaccines Adjuvanted with Stable Emulsion and Toll-Like Receptor 9 Agonist Induce a Robust HSV-2-Specific Cell-Mediated Immune Response, Protect against Symptomatic Disease, and Reduce the Latent Viral Reservoir," J Virol, 91(9), 19 pages.
Chentoufi et al., 2011, "The herpes simplex virus 1 latency-associated transcript promotes functional exhaustion of virus-specific CD8+ T cells in latently infected trigeminal ganglia: a novel immune evasion mechanism," J Virol. 2011;85(17):9127-38.
Allen et al., 2011, "The role of LAT in increased CD8+ T cell exhaustion in trigeminal ganglia of mice latently infected with herpes simplex virus 1," J Virol, 85(9):4184-97.
Mott et al., 2009, "Level of herpes simplex virus type 1 latency correlates with severity of corneal scarring and exhaustion of CD8+ T cells in trigeminal ganglia of latently infected mice," J Virol. 2009;83(5):2246-54.
Chentoufi et al., 2012, "The herpes simplex virus type 1 latency-associated transcript inhibits phenotypic and functional maturation of dendritic cells," Viral Immunol, 25(3):204-15.
Allen et al., 2010, "Immunization with different viral antigens alters the pattern of T cell exhaustion and latency in herpes simplex virus type 1-infected mice," J Virol, 84(23):12315-24.
Frank et al., 2010, "Early CD4(+) T cell help prevents partial CD8(+) T cell exhaustion and promotes maintenance of Herpes Simplex Virus 1 latency," J Immunol, 184(1):277-86.
Wherry, 2011, "T cell exhaustion," Nat Immunol. 2011;12(6):492-9.
Day et al., 2006, "PD-1 expression on HIV-specific T cells is associated with T-cell exhaustion and disease progression," Nature, 443(7109):350-4.
Anderson et al., 2016, "Lag-3, Tim-3, and TIGIT: Co-inhibitory Receptors with Specialized Functions in Immune Regulation," Immunity. 2016;44(5):989-1004.
Van Velzen et al., 2009, "Neuron-interacting satellite glial cells in human trigeminal ganglia have an ARC phenotype," J Immunol, 183(4):2456-61.
White et al., 2001, "Human immunodeficiency virus-specific and CD3-redirected cytotoxic T lymphocyte activity in the human female reproductive tract: lack of correlation between mucosa and peripheral blood," The Journal of infectious diseases, 183(6):977-83.
Wodal et al., 2015, "Immunogenicity and protective efficacy of a Vero cell culture-derived whole-virus H7N9 vaccine in mice and guinea pigs," PloS one. 2015;10(2):e0113963, 16 pages.
Swanson et al., 2015, "Comparison of monovalent glycoprotein B with bivalent GB/pp65 (GP83) vaccine for congenital cytomegalovirus infection in a guinea pig model: Inclusion of GP83 reduces GB antibody response but both vaccine approaches provide equivalent protection against pup mortality," Vaccine. 2015;33(32):4013-8.
Gillis et al., 2014, "Development of a novel, guinea pig-specific IFN-γ ELISPOT assay and characterization of guinea pig cytomegalovirus GP83-specific cellular immune responses following immunization with a modified vaccinia virus Ankara (MVA)-vectored GP83 vaccine," Vaccine. 2014;32(31):3963-70.
Mestecky et al., 1999, "Mucosal immune system of the human genital tract," The Journal of infectious diseases, 179 Suppl 3:S470-4.
Koutsky et al., 1992, "Underdiagnosis of genital herpes by current clinical and viral-isolation procedures," N Engl J Med, 326:1533-9.

Reeves et al., 1981, "Risk of recurrence after first episodes of genital herpes. Relation to HSV type and antibody response," N Engl J Med, 305: 315-9.
Corey et al., 1978, "Ineffectiveness of topical ether for the treatment of genital herpes simplex virus infection," N Engl J Med, 299:237-9.
Fleming et al., 1997, "Herpes simplex virus type 2 in the United States, 1976 to 1994," N Engl J Med, 337:1105-11.
Stanberry et al., 1999, "New developments in the epidemiology, natural history and management of genital herpes," Antiviral Res, 42:1-14.
Stanberry et al., 2000, "Prospects for control of herpes simplex virus disease through immunization," Clin Infect Dis, 30: 549-66.
Cunningham et al., 2012, "Current management and recommendations for access to antiviral therapy of herpes labialis," J Clin Virol, 53:6-11.
Stanberry et al., 2002, "Glycoprotein-D-adjuvant vaccine to prevent genital herpes," N Engl J Med, 347:1652-61.
Burkhard et al., 2015, "Malaria vaccine based on self-assembling protein nanoparticles," Expert Rev Vaccines, 14: 1525-7.
Doll et al., 2015, "Optimizing the design of protein nanoparticles as carriers for vaccine applications," Nanomedicine, 11:1705-13.
El Bissati et al., 2014, "Effectiveness of a novel immunogenic nanoparticle platform for Toxoplasma peptide vaccine in HLA transgenic mice," Vaccine, 32: 3243-8.
El Bissati et al., 2017, "Protein nanovaccine confers robust immunity against Toxoplasma," NPJ Vaccines, 2: 24, 12 pages.
Guo et al. 2013, "Expression, purification and refolding of a self-assembling protein nanoparticle (SAPN) malaria vaccine," Methods, 60: 242-7.
Kaba et al., 2009, "A nonadjuvanted polypeptide nanoparticle vaccine confers long-lasting protection against rodent malaria," J Immunol, 183: 7268-77.
Kaba et al., 2012, "Protective antibody and CD8+ T-cell responses to the Plasmodium falciparum circumsporozoite protein induced by a nanoparticle vaccine," PLoS One, 7: e48304, 11 pages.
Kaba et al., 2018, "Self-assembling protein nanoparticles with built-in flagellin domains increases protective efficacy of a Plasmodium falciparum based vaccine," Vaccine, 36: 906-14.
Karch et al., 2017, "The use of a P. falciparum specific coiled-coil domain to construct a self-assembling protein nanoparticle vaccine to prevent malaria," J Nanobiotechnology, 15: 62, 10 pages.
McCoy et al., 2013, "Mechanisms of protective immune responses induced by the Plasmodium falciparum circumsporozoite protein-based, self-assembling protein nanoparticle vaccine," Malar J, 12: 136, 12 pages.
Seth et al., 2017, "Development of a self-assembling protein nanoparticle vaccine targeting Plasmodium falciparum Circumsporozoite Protein delivered in three Army Liposome Formulation adjuvants," Vaccine, 35: 5448-54.
Ohmori et al., 1997, "Synergy between interferon-gamma and tumor necrosis factor-alpha in transcriptional activation is mediated by cooperation between signal transducer and activator of transcription 1 and nuclear factor kappaB," J Biol Chem, 272: 14899-907.
Thapa et al., 2008, "CXCL9 and CXCL10 expression are critical for control of genital herpes simplex virus type 2 infection through mobilization of HSV-specific CTL and NK cells to the nervous system," J Immunol, 180: 1098-106.
Thapa et al., 2009, "CXCR3 deficiency increases susceptibility to genital herpes simplex virus type 2 infection: Uncoupling of CD8+ T-cell effector function but not migration," J Virol, 83: 9486-501.
Wuest et al., 2011, "CXCL10 expressing hematopoietic-derived cells are requisite in defense against HSV-1 infection in the nervous system of CXCL10 deficient mice," J Neuroimmunol, 234:103-8.
Bloom et al., 2019, "Peripheral AAV Injection for Retrograde Transduction of Dorsal Root and Trigeminal Ganglia," Methods Mol Biol, 1950: 237-47.
Watson et al., 2016, "Adeno-associated Virus Vectors Efficiently Transduce Mouse and Rabbit Sensory Neurons Coinfected with Herpes Simplex Virus 1 following Peripheral Inoculation," J Virol, 90: 7894-901.

(56) References Cited

OTHER PUBLICATIONS

Khan et al., 2017, "Bolstering the Number and Function of HSV-1-Specific CD8+ TEM and TRM cells in Latently Infected Trigeminal Ganglia Reduces Recurrent Ocular Herpes Infection and Disease," J Immunol, 199:186-203.
Liu et al., 2008, "Reduction in severity of a herpes simplex virus type 1 murine infection by treatment with a ribozyme targeting the UL20 gene RNA," J Virol, 82: 7467-74.
Foust et al., 2008, "Neonatal intraperitoneal or intravenous injections of recombinant adeno-associated virus type 8 transduce dorsal root ganglia and lower motor neurons," Hum Gene Ther, 19: 61-70.
Zheng et al., 2010, "Expression of HGF/c-Met is dynamically regulated in the dorsal root ganglions and spinal cord of adult rats following sciatic nerve ligation," Neurosignals, 18: 49-56.
Zhang et al., 2009, "A genital tract peptide epitope vaccine targeting TLR-2 efficiently induces local and systemic CD8+ T cells and protects against herpes simplex virus type 2 challenge," Mucosal Immunol, 2: 129-43.
Pieknik et al., 2019, "Herpes Simplex Virus 2 in Autonomic Ganglia: Evidence for Spontaneous Reactivation," J Virol, 3(11):e00227-19, 10 pages.
Khan et al., 2015, "Phenotypic and functional characterization of herpes simplex virus glycoprotein B epitope-specific effector and memory CD8+ T cells from symptomatic and asymptomatic individuals with ocular herpes," J Virol, 89(7):3776-92.
Ohashi et al., 2011, "Spread of herpes simplex virus to the spinal cord is independent of spread to dorsal root ganglia," J Virol, 85: 3030-2.
Bertke et al., 2009, "Latency-associated transcript (LAT) exon 1 controls herpes simplex virus species-specific phenotypes: reactivation in the guinea pig genital model and neuron subtype-specific latent expression of LAT," J Virol, 83: 10007-15.
Bertke et al., 2011, "A5-positive primary sensory neurons are nonpermissive for productive infection with herpes simplex virus 1 in vitro," J Virol, 85: 6669-77.
Tang et al., 2011, "Herpes simplex virus 2 microRNA miR-H6 is a novel latency-associated transcript-associated microRNA, but reduction of its expression does not influence the establishment of viral latency or the recurrence phenotype," J Virol, 85: 4501-9.
Bertke et al., 2012, "LAT region factors mediating differential neuronal tropism of HSV-1 and HSV-2 do not act in trans," PLoS One, 7: e53281, 7 pages.
Bertke et al., 2013, "Different mechanisms regulate productive herpes simplex virus 1 (HSV-1) and HSV-2 infections in adult trigeminal neurons," J Virol, 87: 6512-6.
Theil et al., 2003, "Dually infected (HSV-1/VZV) single neurons in human trigeminal ganglia," Ann Neurol, 54:678-82.
Derfuss et al., 2007, "Presence of HSV-1 immediate early genes and clonally expanded T-cells with a memory effector phenotype in human trigeminal ganglia," Brain Pathol, 17:389-98.
Hufner et al., 2006, "Latency of alpha-herpes viruses is accompanied by a chronic inflammation in human trigeminal ganglia but not in dorsal root ganglia," J Neuropathol Exp Neurol, 65:1022-30.
Theil et al., 2001, "Prevalence of HSV-1 LAT in human trigeminal, geniculate, and vestibular ganglia and its implication for cranial nerve syndromes," Brain Pathol, 11:408-13.
Liu et al., 1996, "Inflammatory infiltration of the trigeminal ganglion after herpes simplex virus type 1 corneal infection," J Virol, 70:264-71.
Dervillez et al., 2013, "Asymptomatic HLA-A*02:01-restricted epitopes from herpes simplex virus glycoprotein B preferentially recall polyfunctional CD8+ T cells from seropositive asymptomatic individuals and protect HLA transgenic mice against ocular herpes," J Immunol, 191:5124-38.
Mackay et al., 2013, "The developmental pathway for CD103(+)CD8+ tissue-resident memory T cells of skin," Nat Immunol, 14:1294-301.
Mackay et al., 2015, "T-box Transcription Factors Combine with the Cytokines TGF-β and IL-15 to Control Tissue-Resident Memory T Cell Fate," Immunity, 43:1101-11.
Tian et al., 2019, "CD28H expression identifies resident memory CD8+ T cells with less cytotoxicity in human peripheral tissues and cancers," Oncoimmunology, 8:e1538440, 9 pages.
Mami-Chouaib et al., 2018, "Resident memory T cells, critical components in tumor immunology," J Immunother Cancer. (2018); 6: 87.
Woon et al., 2016, "Compartmentalization of Total and Virus-Specific Tissue-Resident Memory CD8+ T Cells in Human Lymphoid Organs," PLoS Pathog, 12:e1005799, 19 pages.
Johnson et al., 2010, "Reconstitution of circulating lymphocyte counts in FTY720-treated MS patients," Clin Immunol, 137:15-20.
Pinschewer et al., 2000, "FTY720 immunosuppression impairs effector T cell peripheral homing without affecting induction, expansion, and memory," J Immunol, 164:5761-70.
Johnson et al., 2010, "Distinct properties of circulating CD8+T cells in FTY720-treated patients with multiple sclerosis," Arch Neurol, 67:1449-55.

\* cited by examiner

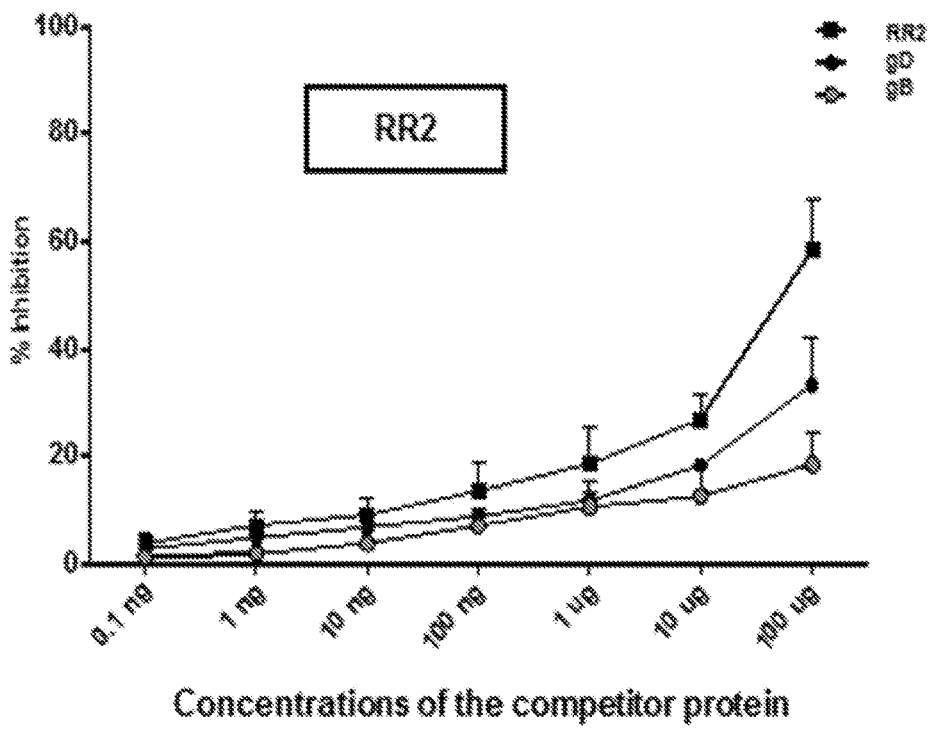
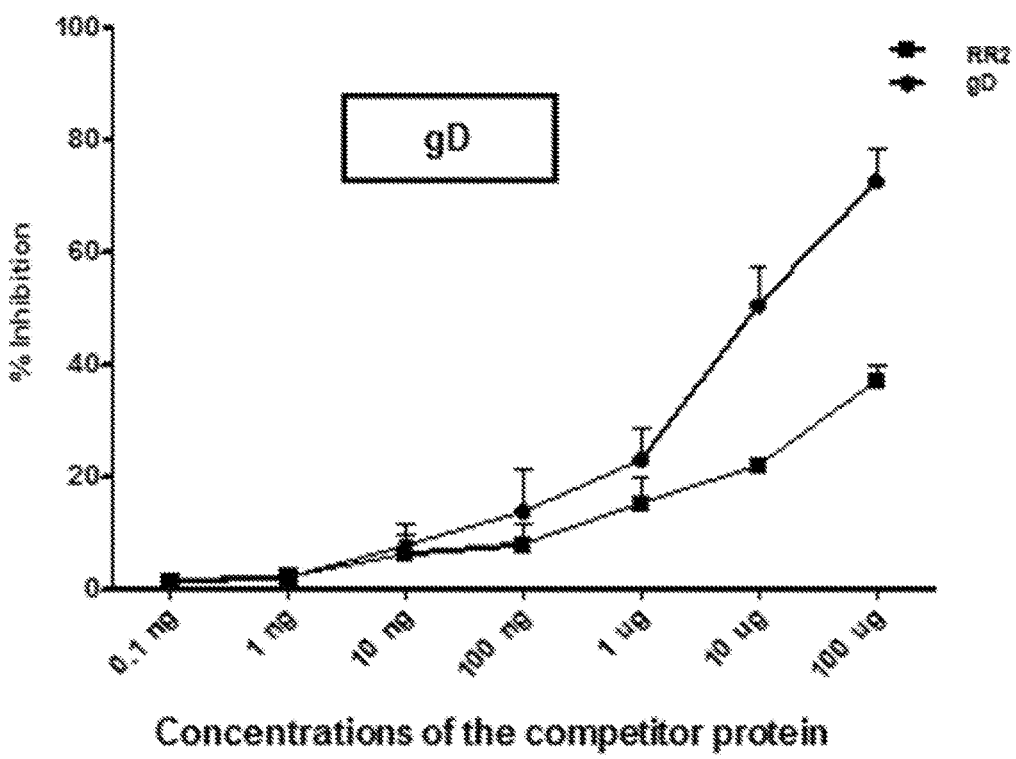
Fig. 3D

| SAPN-Ags (Prime) | AAV-8 expressing chemokines (Pull) | | | |
|---|---|---|---|---|
| | CXCL9 | CXCL10 | CXCL11 | None |
| SAPN-VP16 | G1 | G2 | G3 | G25 |
| SAPN-VP22 | G4 | G5 | G6 | G26 |
| SAPN-RR1 | G7 | G8 | G9 | G27 |
| SAPN-RR2 | G10 | G11 | G12 | G28 |
| SAPN-VP16/VP22 | G13 | G14 | G15 | G29 |
| SAPN-RR1/RR2 | G16 | G17 | G18 | G30 |
| SAPN-gD | G19 | G20 | G21 | G31 |
| Mock | G22 | G23 | G24 | G32 |

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Seqence
<220> FEATURE:
<223> OTHER INFORMATION: CpG oligonucleotide

<400> SEQUENCE: 1
tcgtcgttgt cgttttgtcg tt                                             22

<210> SEQ ID NO 2
<211> LENGTH: 23
<212> TYPE: DNA
<213> ORGANISM: Artificial Seqence
<220> FEATURE:
<223> OTHER INFORMATION: Forward primer for HSV-2 Us9

<400> SEQUENCE: 2
ggcagaagcc tactactcgg aaa                                            23

<210> SEQ ID NO 3
<211> LENGTH: 18
<212> TYPE: DNA
<213> ORGANISM: Artificial Seqence
<220> FEATURE:
<223> OTHER INFORMATION: Reverse primer for HSV-2 Us9

<400> SEQUENCE: 3
ccatgcgcac gaggaagt                                                  18

<210> SEQ ID NO 4
<211> LENGTH: 13
<212> TYPE: DNA
<213> ORGANISM: Artificial Seqence
<220> FEATURE:
<223> OTHER INFORMATION: Probe for HSV-2 Us9

<400> SEQUENCE: 4
cgaggccgcc aac                                                       13
```

PROTECTION AGAINST RECURRENT GENITAL HERPES BY THERAPEUTIC IMMUNIZATION WITH HERPES SIMPLEX VIRUS TYPE 2 RIBONUCLEOTIDE REDUCTASE PROTEIN SUBUNITS

CROSS REFERENCE TO RELATED APPLICATIONS

This application claims priority to U.S. Provisional Application No. 62/786,617, filed Dec. 31, 2018 and to U.S. Provisional Application No. 62/716,347, filed Aug. 8, 2018 which are hereby incorporated by reference herein in their entirety.

BACKGROUND OF THE INVENTION

Herpes simplex virus type 2 (HSV-2) affects more women than men, with 350 million women worldwide, 15-49 years old, currently infected. After vaginal mucosa (VM) exposure, HSV-2 replicates in the mucosal epithelial cells thereby causing acute genital herpetic lesions. Once the acute primary infection is cleared, the virus enters the nerve termini innervating peripheral vaginal tissues, and is subsequently transported to the nucleus of the sensory neurons of dorsal root ganglia (DRG) where it goes into a lifelong "steady-state" latency. Roughly 80% of HSV-2-seropositive asymptomatic women are unaware of their infection as they never develop any apparent recurrent symptoms. In contrast, in symptomatic women, the latent infection is often interrupted by sporadic reactivation that leads to recurrences of genital lesions, painful blisters that can burst and form ulcers. Despite the availability of many intervention strategies, such as sexual behavior education, barrier methods, and the costly guanine nucleoside anti-viral drug therapies (e.g. Acyclovir and derivatives), eliminating or at least reducing recurrent genital herpes remains a challenge (Zhang et al., 2009, Mucosal Immunol, 2(2):129-43; Dasgupta et al., 2010, Future Microbiol, 5(1):1-4; Zhang et al., 2008, Clinical and vaccine immunology, 15(9):1436-49; Dasgupta et al., 2012, J Virol, 86(8):4358-69; Chentoufi et al., 2012, Clin Dev Immunol, 2012:187585). Moreover, both symptomatic and asymptomatic women experience subclinical virus shedding and, hence, can transmit the virus, underscoring the need for an anti-viral therapeutic vaccine to prevent or reduce virus reactivation and/or its shedding in the genital tract (instead of a therapeutic vaccine that would just reduce symptoms). Currently, the medical opinion is that an effective therapeutic vaccine that prevents or reduces virus shedding in the genital tract would constitute the best approach to protect from recurrent genital herpes (Dasgupta et al., 2012, J Virol, 86(8):4358-69; Kalantari-Dehaghi et al., 2012, J Virol, 86(8):4328-39; Dervillez et al., 2012, Future Virol, 7(4):371-378). It is becoming increasingly clear that the acquired immune responses that occur following natural exposure to the virus in symptomatic women are not sufficient for protection against recurrent genital herpes (Rouse et al., 2006, Immunological reviews, 212:272-86; Cunningham et al., 2006, The Journal of infectious diseases, 194 Suppl 1:S11-8; MasCasullo et al., 2005, Viral Immunol, 18(4):595-606; Koelle and Ghiasi, 2005, Curr Eye Res, 30(11):929-42; Jones and Cunningham, 2004, Herpes, 11(1):12-7). This implies that a successful therapeutic vaccine must be able to boost an immune response that is stronger and/or different than the natural immunity induced by the virus itself (Dervillez et al., 2012, Future Virol, 7(4):371-378). Therapeutic human vaccination with the whole herpes HSV-2 live attenuated vaccines induced B- and T-cell protective immunity against recurrent genital herpes in animal models (Dropulic and Cohen, 2012, Expert Rev Vaccines, 11(12):1429-40). The same level of protection has yet to be achieved by a subunit vaccine (Stanberry, 2004, Herpes, 11 Suppl 3:161A-9A; Belshe et al., 2012, The New England journal of medicine, 366:34-43). Protein are proven excellent candidates for subunit vaccine development due to their safety, cost effectiveness, and rapid preparation (Skoberne et al., 2013, J Virol, 87(7):3930-42). Previous studies have identified T cell antigens by screening HSV-2 open-reading frames (ORFs) by PBMC-derived T cells from HSV-2 seropositive individuals (Laing et al., 2010, J Clin Immunol, 30(5):703-22). However, aside from three reports (Dasgupta et al., 2012, J Virol, 86(8):4358-69; Kalantari-Dehaghi et al., 2012, J Virol, 86(8):4328-39; Long et al., 2014, Virology, 464-465:296-311), the breadth of antigens recognized by B- and T-cells from HSV-2 seropositive symptomatic versus asymptomatic individuals is largely unknown.

Over the last two decades, a single subunit vaccine strategy, based on HSV-2 glycoprotein D (gD), delivered with or without gB, has been tested and retested in clinical trials (Belshe et al., 2012, The New England journal of medicine, 366:34-43; Johnston et al., 2011, J Clin Invest. 121(12):4600-9). This subunit vaccine strategy proved unsuccessful in clinical trials despite inducing strong neutralizing antibodies (Belshe et al., 2012, The New England journal of medicine, 366:34-43).

Further, characterization of HSV-specific CD4+ and CD8+ cells in genital herpes symptomatic and asymptomatic individuals have been limited to blood-derived T cells (Kalantari-Dehaghi et al., 2012, J Virol. 2012;86(8):4328-39; Long et al., 2014, Virology, 464-465). This is mainly because of the ethical and practical limitations in obtaining DRG- and vaginal mucosa tissues-derived T cells that would allow routine characterization of phenotype and function in a large scale (Peng et al., 2012, J Virol, 86(19):10587-96; Zhu et al., 2007, J Exp Med, 204(3):595-603; Zhu et al., 2013, Nature. 2013;497(7450):494-7). Thus, a reliable animal model that would mimic recurrent genital herpes as occurs in humans would help speed up the characterization of tissue-resident HSV-specific CD4+ and CD8+ cells and to compare the contribution of DRG- and vaginal mucosa-derived versus peripheral blood-derived CD4+ and CD8+ cells in protection against recurrent genital herpes. The most commonly-used small animal model for preclinical testing of immunotherapeutic vaccine candidates against recurrent genital herpes has been the guinea pig model (Awasthi et al., 2014, J Virol, 88(15):8421-32; Awasthi et al., 2014, J Virol, 88(4):2000-10; Awasthi et al., 2011, J Virol, 85(20):10472-86). Unlike in mice, intravaginal HSV-2 infections in guinea pigs: (i) leads to intermittent, spontaneous reactivation events resulting in recurrent virus shedding in the genital tract, as occurs in women; (ii) this virus shedding leads to clinical and pathological features of recurrent genital lesions, with self-limiting quantifiable vulvo-vaginitis, akin to those seen in women (Awasthi et al., 2014, J Virol, 88(15):8421-32; Awasthi et al., 2014, J Virol, 88(4):2000-10; Awasthi et al., 2011, J Virol, 85(20):10472-86; Thornton et al., 1984, Vaccine, 2(2):141-8; Veselenak et al., 2018, Virology, 518:349-57; Perry et al., J Immunol Methods, 439:1-7; Xia et al., 2014, PloS one, 9(12):e114652).

Given the limitations of current therapy, there is a need in the art for therapeutic vaccines for the treatment and prevention of herpes simplex virus infection and associated diseases. The present invention addresses this unmet need in the art.

SUMMARY OF THE INVENTION

In one embodiment, the invention relates to a composition for treating or preventing a herpesvirus infection comprising at least one of: a) a gD, RR2, RR1, VP22, gB, VP16, VP13/14, VP11/12 or UL25 HSV antigen; or b) a nucleic acid molecule encoding a gD, RR2, RR1, VP22, gB, VP16, VP13/14, VP11/12 or UL25 HSV antigen. In one embodiment, the composition comprises at least one of a gD, RR2 or VP22 HSV antigen. In one embodiment, the composition comprises a nucleotide sequence encoding at least one of a gD, RR2 or VP22 HSV antigen. In one embodiment, the composition comprises a RR2 HSV antigen. In one embodiment, the composition comprises a nucleotide sequence encoding a RR2 HSV antigen. In one embodiment, the composition comprises a UL25 HSV antigen. In one embodiment, the composition comprises a nucleotide sequence encoding a UL25 HSV antigen.

In one embodiment, the composition comprises one or more isolated nucleic acids, where the one or more isolated nucleic acids encode multiple HSV antigens, wherein each nucleic acid molecule comprises a nucleotide sequence encoding a gD, RR2, VP22, gB, VP16, VP13/14, VP11/12 or UL25 HSV antigen.

In one embodiment, the composition comprises a self-assembling protein nanoparticle (SAPN) comprising at least one gD, RR2, RR1, VP22, gB, VP16, VP13/14, VP11/12 or UL25 HSV antigen. In one embodiment, the SAPN further comprises flagellin. In one embodiment, the SAPN comprises a VP16 HSV antigen. In one embodiment, the SAPN comprises a VP22 HSV antigen. In one embodiment, the SAPN comprises a RR1 HSV antigen. In one embodiment, the SAPN comprises a RR2 HSV antigen. In one embodiment, the SAPN comprises VP16 and VP22 HSV antigens. In one embodiment, the SAPN comprises RR1 and RR2 HSV antigens.

In one embodiment, the herpesvirus infection is associated with herpes simplex type I (HSV1), herpes simplex virus 2 (HSV2), human herpresvirus-3 (HHV-3; varicella zoster virus (VZV), human herpesvirus-4 (HHV-4; Epstein-Barr virus (EBV)), human herpesvirus-5 (HHV-5; Cytomegalovirus (CMV)), human herpesvirus-6 (HHV-6; roseolovirus), human herpes virus-7 (HHV-7), or human herpesvirus-8 (HHV-8; Karposi's sarcoma-associated herpesvirus (KSHV)).

In one embodiment, the invention relates to a pharmaceutical composition comprising at least one of: a) a gD, RR2, RR1, VP22, gB, VP16, VP13/14, VP11/12 or UL25 HSV antigen; or b) a nucleic acid molecule encoding a gD, RR2, RR1, VP22, gB, VP16, VP13/14, VP11/12 or UL25 HSV antigen; and a pharmaceutically acceptable excipient. In one embodiment, the composition comprises at least one of a gD, RR2 or VP22 HSV antigen. In one embodiment, the composition comprises a nucleotide sequence encoding at least one of a gD, RR2 or VP22 HSV antigen. In one embodiment, the composition comprises a RR2 HSV antigen. In one embodiment, the composition comprises a nucleotide sequence encoding a RR2 HSV antigen. In one embodiment, the composition comprises a UL25 HSV antigen. In one embodiment, the composition comprises a nucleotide sequence encoding a UL25 HSV antigen.

In one embodiment, the pharmaceutical composition comprises a SAPN comprising at least one gD, RR2, RR1, VP22, gB, VP16, VP13/14, VP11/12 or UL25 HSV antigen. In one embodiment, the SAPN further comprises flagellin. In one embodiment, the SAPN comprises a VP16 HSV antigen. In one embodiment, the SAPN comprises a VP22 HSV antigen. In one embodiment, the SAPN comprises a RR1 HSV antigen. In one embodiment, the SAPN comprises a RR2 HSV antigen. In one embodiment, the SAPN comprises VP16 and VP22 HSV antigens. In one embodiment, the SAPN comprises RR1 and RR2 HSV antigens.

In one embodiment, the invention relates to a method of treating or preventing a herpesvirus infection or herpesvirus-associated disorder in a subject, the method comprising contacting a cell of the subject with a therapeutically effective amount of a composition comprising at least one of: a) a gD, RR2, RR1, VP22, gB, VP16, VP13/14, VP11/12 or UL25 HSV antigen; or b) a nucleic acid molecule encoding a gD, RR2, RR1, VP22, gB, VP16, VP13/14, VP11/12 or UL25 HSV antigen. In one embodiment, the composition comprises at least one of a gD, RR2 or VP22 HSV antigen. In one embodiment, the composition comprises a nucleotide sequence encoding at least one of a gD, RR2 or VP22 HSV antigen. In one embodiment, the composition comprises a RR2 HSV antigen. In one embodiment, the composition comprises a nucleotide sequence encoding a RR2 HSV antigen. In one embodiment, the composition comprises a UL25 HSV antigen. In one embodiment, the composition comprises a nucleotide sequence encoding a UL25 HSV antigen.

In one embodiment, the composition comprises a SAPN comprising at least one gD, RR2, RR1, VP22, gB, VP16, VP13/14, VP11/12 or UL25 HSV antigen. In one embodiment, the SAPN further comprises flagellin. In one embodiment, the SAPN comprises a VP16 HSV antigen. In one embodiment, the SAPN comprises a VP22 HSV antigen. In one embodiment, the SAPN comprises a RR1 HSV antigen. In one embodiment, the SAPN comprises a RR2 HSV antigen. In one embodiment, the SAPN comprises VP16 and VP22 HSV antigens. In one embodiment, the SAPN comprises RR1 and RR2 HSV antigens.

In one embodiment, the composition is administered as a prime vaccine in a prime and pull treatment regimen. In one embodiment, the pull treatment of the prime and pull treatment regimen comprises administration of at least one cytokine selected from CXCL9, CXCL10 and CXCL11.

In one embodiment, the herpesvirus infection or herpesvirus-associated disorder is associated with herpes simplex type I (HSV1), herpes simplex virus 2 (HSV2), human herpresvirus-3 (HHV-3; varicella zoster virus (VZV), human herpesvirus-4 (HHV-4; Epstein-Barr virus (EBV)), human herpesvirus-5 (HHV-5; Cytomegalovirus (CMV)), human herpesvirus-6 (HHV-6; roseolovirus), human herpes virus-7 (HHV-7), or human herpesvirus-8 (HHV-8; Karposi's sarcoma-associated herpesvirus (KSHV)).

In one embodiment, the herpesvirus-associated disorder is labial herpes, genital herpes, chickenpox, shingles, primary herpes infection with a human alpha-herpesvirus, Bell's palsy, vestibular neuritis, or herpetic neuralgia.

In one embodiment, the subject has an asymptomatic herpesvirus infection, and the method comprises contacting a cell of the subject with a therapeutically effective amount of a composition comprising at least one of: a) a gD, RR2, RR1, VP22, gB, VP16, VP13/14, or VP11/12 HSV antigen; or b) a nucleic acid molecule encoding a gD, RR2, RR1, VP22, gB, VP16, VP13/14, or VP11/12 HSV antigen.

In one embodiment, the subject has a symptomatic herpesvirus infection, and the method comprises contacting a cell of the subject with a therapeutically effective amount of a composition comprising a) a UL25 HSV antigen; or b) a nucleic acid molecule encoding a UL25 HSV antigen.

BRIEF DESCRIPTION OF THE DRAWINGS

The following detailed description of preferred embodiments of the invention will be better understood when read in conjunction with the appended drawings. It should be understood, however, that the invention is not limited to the precise arrangements and instrumentalities of the embodiments shown in the drawings.

FIG. 1, comprising FIG. 1A depicts the average intensity of recognition of ORFs expressing HSV-2 proteins by T cells from HSV-2 seropositive symptomatic (n=10) and asymptomatic individuals (n=10), as tested by IFN-γ-production. The names of HSV-2 ORFs driving two representative positive responses are indicated. FIG. 1B depicts VP11/12 and VP13/14-specific CFSE(+) proliferative T cells from symptomatic and asymptomatic individuals represented in FIG. 1A. FIG. 1C and FIG. 1D depict representative analyses of HSV-2 VP11/12 and VP13/14-specific IFN-γ-producing CD4+ T cells and CD8+ T cells, respectively, from one symptomatic and one asymptomatic individual. Representative analysis from the one symptomatic and one asymptomatic individual (top panels) and average from the 10 symptomatic and 10 asymptomatic individuals (bottom panels). The results are representative from 3 independent experiments. The P-value compares the results from 10 symptomatic and 10 asymptomatic individuals. Values were calculated using the ANOVA two-tail test.

FIG. 2, comprising FIG. 2A depicts a timeline of HSV-2 infection, immunization, immunological and virological analyses. Guinea pigs (n=60) are infected intravaginally on day 0 with $5 \times 10^5$ pfu of HSV-2 (strain MS). Once acute infection is resolved, the remaining latently infected animals are randomly divided into 8 groups (n=4) and then vaccinated intramuscularly twice, on day 15 and on day 25 post-infection, with 10 μg of the indicated HSV-2 protein-based subunit vaccine (gD, RR2, VP22, gB, VP16, VP13/14, VP11/12 and UL25) emulsified in Alum+CpG adjuvants. The replication defective HSV-2 d15-29 mutant vaccine (DL5-29) is used as a positive control (d15-29). Mock-vaccinated guinea pigs which received Alum+CpG adjuvants alone are used as negative control (Mock). From day 35 to day 80 post-infection (i.e. day 10 to day 55 after final immunization), vaccinated and non-vaccinated animals were observed daily for: (i) the severity of genital herpetic lesions scored on a scale of 0 to 4 and pictures of genital areas taken; and (ii) vaginal swabs were collected daily from day 35 to day 65 post-infection (i.e. day 10 to day 40 after final immunization) to detect virus shedding and to quantify HSV-2 DNA copy numbers. FIG. 2B depicts HSV-2 DNA copy numbers detected in the DRG of each group of vaccinated and mock-vaccinated guinea pigs. FIG. 2C depicts the cumulative vaginal shedding of HSV-2 during recurrent infection (virus titers). FIG. 2D shows cumulative vaginal lesions (left panel) and cumulative positive days with recurrent genital lesions (left panel). The severity of genital herpetic lesions was scored on a scale of 0 to 4, where 0 reflects no disease, 1 reflects redness, 2 reflects a single lesion, 3 reflects coalesced lesions, and 4 reflects ulcerated lesions. FIG. 2E depicts representative images of genital lesions in guinea pigs vaccinated with: (i) protective antigens (PI=gD, RR2 and VP22 proteins (6 pictures in left); (ii) with moderately-protective antigens (MP=gB, VP16, VP13/14 and VP11/12) (8 pictures in middle); and (iii) with non-protective antigen (NP=UL25), mock-vaccinated control and d15-29 positive control (6 pictures in right). The indicated P values show statistical significance between the HSV-2 vaccinated and mock-vaccinated control groups. * $P<0.05$ is considered significant.

FIG. 3, comprising FIG. 3A depicts levels of Ag-specific IgG detected by ELISA from the guinea pigs vaccinated with gD, RR2, VP22, gB, VP16, VP13/14, VP11/12 and UL25, the mock-vaccinated group (Mock) and the DL5-29 vaccine positive control group. All sera were evaluated at 1:1000. FIG. 3B depicts the binding affinity of IgG from the indicated HSV-2 antigen vaccinated compared to the mock-vaccinated groups (Mock) to native proteins on HSV-2 (MS strain) by ELISA. FIG. 3C depicts that immune sera were tested for neutralizing antibody titers. The dotted line represents neutralizing antibody titers in mock-vaccinated guinea pigs. The neutralization point was defined as the serum dilution that reduces the number of plaques by 50% compared to positive control (cells only). FIG. 3D depicts that ELISA plates were coated with 1 μg of RR2 protein (left panel), 1 μg of gD protein (middle panel), or 1 μg of gB protein (right panel). ELISA plates were then incubated with serum from RR2, gD or gB immunized guinea pigs and pre-incubated with different concentrations of the competitor protein (i.e. RR2, gB or gD). The percentage of inhibition at each tested concentration of the competitor protein was calculated with respect to the OD value of the respective immune serum alone, incubated in the absence of the competitor protein. Statistical analysis was performed by 2-way ANOVA for repeated measures followed by Bonferroni's post-test for significance. * $P<0.05$ is considered significant.

FIG. 4, comprising FIG. 4A depicts representative FACS data of the frequencies of CD4+ and CD8+ T cells detected in the VM of vaccinated and mock-vaccinated animals. FIG. 4B depicts quantification of VM-resident CD4+ and CD8+ T cells following therapeutic vaccination with various HSV-2 Antigens. Average frequencies and absolute numbers of CD4+ T cells (top panels) and CD8+ T cells (bottom panels) were determined using FACS in the VM of vaccinated and mock-vaccinated animals. Cells were analyzed using a BD FACSCalibur with a total of $4 \times 10^5$ events. Density plot showing the percentage of CD4+ T cells and CD8+ T cells representative of two independent experiments. The indicated P values performed by 2-way ANOVA for repeated measures followed by Bonferroni's post-test for significance, show statistical significance between HSV-2 vaccinated and mock-vaccinated control groups. * $P<0.05$ is considered significant. FIG. 4C depicts a visualization of CD4+ and CD8+ T cell infiltration, using fluorescence microscopy, within the vaginal mucosa of HSV-2 infected guinea pigs following therapeutic vaccination with various HSV-2 antigens. Sections of the vaginal mucosa from vaccinated and mock-vaccinated animals were co-stained using mAb specific to CD4+ T cells, CD8+ T cells and DAPI (DNA stain).

FIG. 5, comprising FIG. 5A depicts the enumeration of IFN-γ spot forming units (SFU) from guinea pigs immunized with various antigens. Representative wells of IFN-γ-producing cells measured ex vivo by ELISpot assay from VM cells ($10^5$ cells/well) and stimulated for 48 hours with 10 μg of various HSV-2 proteins are depicted. The number on the top of each image of representative ELISpot wells represents the number of IFN-γ producing spot forming T cells (SFC) per one million total vaginal mucosal cells. FIG. 5B depicts the average data of IFN-γ-producing cells measured by ELISpot assay from the VM of four guinea pigs/per group, either ex vivo or after 48 hours in vitro stimulation with the indicated immunizing HSV-2 protein. Vaginal mucosa cell suspensions plated $10^5$ cells/well and either left unstimulated (Un-Stim) or stimulated with 10 μg (Stim) with the indicated HSV-2 proteins. IFN-γ production is depicted by the number of spot forming cells (SFC) per one million VM cells of HSV-2 infected vaccinated and mock-vaccinated control groups. FIG. 5C depicts the frequencies of vaginal mucosa-resident CRTAM+CD4+ T cells (top row) and of CRTAM+CD8+ T cells (bottom row). VM cell suspensions were stained with either a mAb specific to the activation marker CRTAM, CD4 and CD8 and analyzed by FACS. The numbers on the top of each dot plot indicate the percentage of CRTAM+CD4+ T cells (top row) and of CRTAM+CD8+ T cells (bottom row) per vaginal mucosal total cells, as determined by FACS. FIG. 5D depicts the proliferative response of vaginal mucosa-resident CFSE+CD4+ T cells (top row) and of CFSE+CD8+ T cells (bottom row). VM cell suspensions were labeled with CFSE ($2.5 \times 10^6$ cells/well) either alone (Mock) and in the presence of the indicated immunizing HSV-2 protein and proliferative cells quantified by FACS. The indicated P values show statistical significance between HSV-2 infected vaccinated and mock-vaccinated control groups. * P<0.05 is considered significant.

FIG. 6, comprising FIG. 6A depicts a timeline of HSV-2 infection, IVAG and IM immunization, immunological and virological analyses. Once acute infection is resolved, latently infected animals are randomly divided into three groups (n=11) and then vaccinated twice intramuscularly, on days 15 and 25 post-infection, with either RR2 protein emulsified in Alum+CpG adjuvants (group 1) or with the replication defective d15-29 vaccine (positive control, group 2). Mock-vaccinated guinea pigs, which received adjuvant alone, are used as negative control (Mock, group 3). FIG. 6B depicts the cumulative virus shedding detected in RR2-vaccinated, d15-29-vaccinated and mock-vaccinated controls. FIG. 6C depicts the cumulative vaginal lesions (left panel) and cumulative number of days with recurrent genital lesions (right panel) detected in RR2-vaccinated, d15-29-vaccinated and mock-vaccinated controls. FIG. 6D depicts representative images of genital lesions in guinea pigs vaccinated with RR2 protein or d15-29 vaccine and mock vaccinated animals. FIG. 6E depicts frequencies of CD4+ and CD8+ T cells detected by FACS in the VM tissue of RR2 vaccinated animals. FIG. 6F depictsfFrequencies of functional CRTAM+CD8+ T cells (top row) and of CFSE+CD8+ T cells (bottom row) and IFN-γ-producing cells, enumerated ex vivo by ELISPOT assay (bottom panel) in the VM of RR2 vaccinated and d15-29-vaccinated animals compared to mock-vaccinated animals. FIG. 6G depicts frequencies of exhausted PD-1+CD8+ T cells (top panels) and TIM-3+CD8+ T cells (bottom panels) detected in the VM of RR2 vaccinated and d15-29-vaccinated animals compared to mock-vaccinated animals. The indicated P values show statistical significance between RR2-vaccinated and mock-vaccinated control groups. * P <0.05 is considered significant.

FIG. 7, comprising FIG. 7A depicts a timeline of HSV-2 infection, IVAG and IM immunization, immunological and virological analyses. Guinea pigs (n=30) were infected intravaginally with $5 \times 10^5$ pfu of HSV-2 (MS strain). Once acute infection resolved, latently infected animals were randomly divided into four groups (n=10) and then vaccinated with RR2 protein emulsified in Alum+CpG adjuvant either intravaginally (IVAG) or intramuscularly (IM) on days 15 and 25. Replication defective HSV-2 d15-29 mutant virus vaccine delivered IVAG was used as a positive control (DI5-29). Mock-vaccinated guinea pigs, which received IVAG Alum+CpG adjuvants alone, were used as negative control (Mock). FIG. 7B depicts representative images of genital lesions in guinea pigs vaccinated with RR2 protein either by IVAG or IM route (4 pictures in left). Representative images of DI5-29 vaccinated and mock-vaccinated animals (4 pictures in right) are shown. FIG. 7C depicts cumulative vaginal lesions (left panel) and cumulative positive days with recurrences (right panel) following IVAG versus IM vaccinations. FIG. 7D depicts HSV-2 DNA copy numbers detected in the DRG on day 80 PI following vaccination by either IVAG or IM route. FIG. 7E depicts representative FACS data (left panels) and average frequencies and numbers (right panels) of CD4+ T cells and CD8+ T cells in guinea pigs vaccinated with RR2 protein either by IVAG or IM route. FIG. 7F depicts representative FACS data (left panels) and average frequencies and numbers (right panels) of IFN-γ+CD4+T cells and IFN-γ+CD8+ T cells vaccinated either by IVAG or IM route. The indicated P values show statistical significance between the groups of animals vaccinated IVAG versus IM. *P<0.05 is considered significant.

FIG. 8, comprising FIG. 8A depicts a timeline of HSV-2 infection, IVAG and IM immunization and CD4+ and CD8+ T cell depletion. FIG. 8B depicts representative FACS data of the frequencies of CD4+ T cells detected in the SPL. FIG. 8C depicts representative FACS data of the frequencies of CD8+ T cells detected in the SPL. FIG. 8D depicts representative FACS data of the frequencies of CD4+ T cells detected in the VM. FIG. 8E depicts representative FACS data of the frequencies of CD8+ T cells detected in the VM. FIG. 8F depicts cumulative vaginal lesion in RR2 and d15-29 vaccinated groups following CD4+ or CD8+ T cell depletion. FIG. 8G depicts representative images of genital lesions in guinea pigs vaccinated with RR2 protein or DI5-29 and depleted from either CD4+ or CD8+ cells. The indicated P values show statistical significance between CD4+/CD8+ T cells depleted groups and mock-depleted group. * P<0.05 is considered significant.

FIG. 12A depicts the profile of CXCR3 gene expression detected in HSV-specific CD8+ T cells from asymptomatic (ASYMP) humans. FIG. 12B depicts the profile of CXCR3 gene expression detected in protected guinea pigs by RNA-Seq. FIG. 12C depicts the frequency of CXCR3+CD8+ T cells detected by FACS, FIG. 12D depicts the expression levels of CXCR3, CXCL9, CXCL10 and CXCL11 proteins detected by IHC. FIG. 12E depicts the expression levels of CXCR3, CXCL9, CXCL10 and CXCL11 proteins detected by western blot in DRG-resident CD8+ T cells from protected vs. non-protected guinea pigs. FIG. 12F depicts that there are increased numbers of CD4+ and CD8+ T cells localized to DRG tissues of protected guinea (top) compared to DRG of non-protected guinea pigs (bottom).

FIG. 5A depicts a schematic diagram of the treatment. FIG. 5B depicts representative data of expression of GFP in the DRG and VMC of HSV-2 infected guinea pigs. FIG. 15C depicts the average GFP expression in 5 guinea pigs. (*) and (**)<0.05.

FIG. 18 depicts a table showing the groups for immunization with the prime/pull vaccine.

FIG. 19A depicts that the viral particle comprises 60 copies of VP22 protein and a flagellin adjuvant. FIG. 19B depicts transmission electron microscopy of a nanoparticle preparation.

FIG. 23A depicts a flow cytometry analysis of CD4+ and CD8+ expression. Gated on CD44pos cells. FIG. 23A depicts a quantification of the number of CD4+ and CD8+ T cells.

DETAILED DESCRIPTION

Figure 1A:
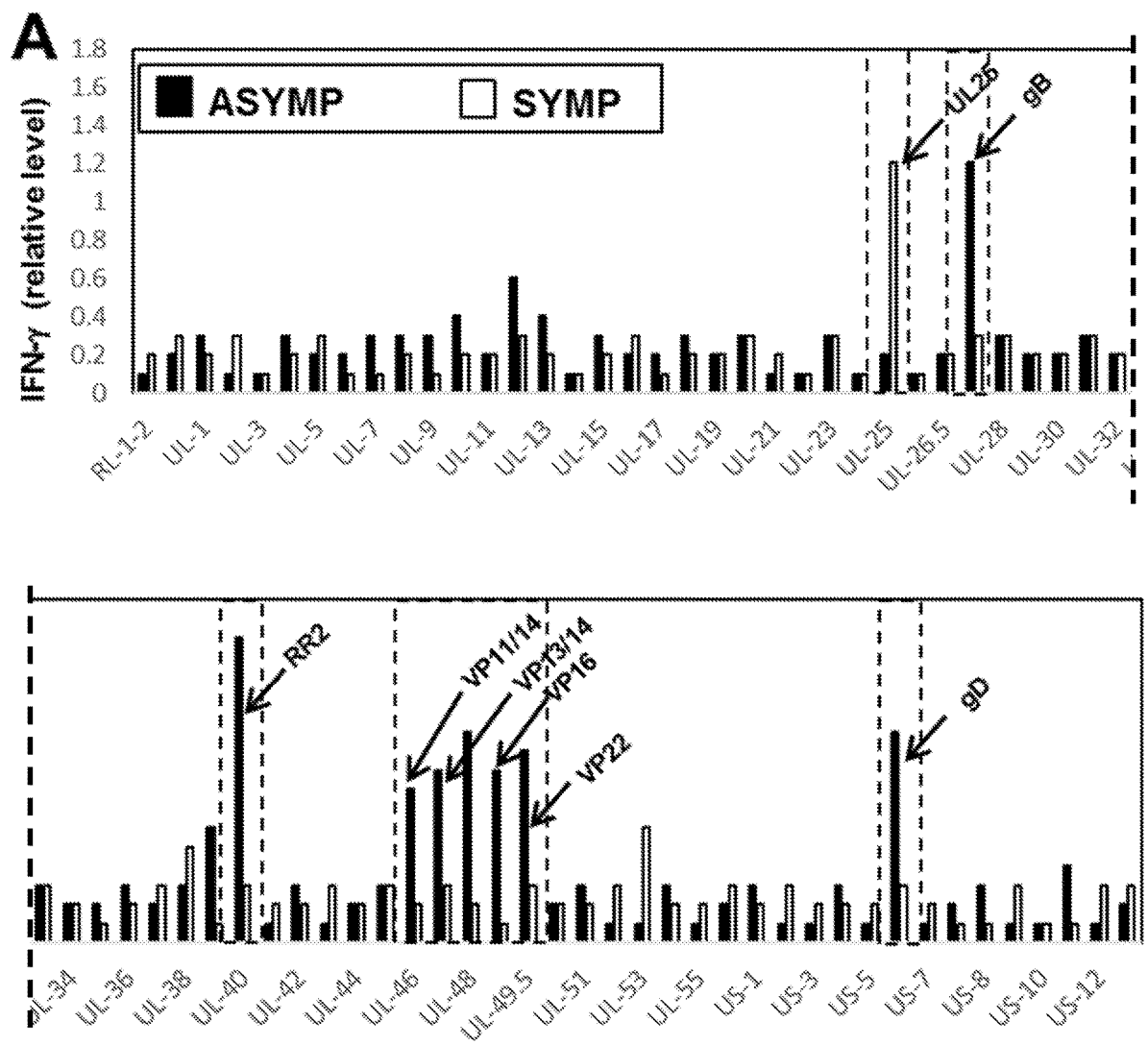
FIG. 1A through FIG. 1D, depicts the results of example experiments demonstrating CD4+ and CD8+ T cell responses against HSV-2 herpes antigens detected from symptomatic and asymptomatic patients.

The present invention relates to compositions and methods for the treatment or prevention of a herpesvirus infection in a subject in need thereof. For example, in certain embodiments, the present invention provides compositions that specifically induce an immune response against human herpesviruses, for example, human herpes simplex type 2 (HSV-2). Such compositions can be administered to a subject having acute or latent herpesvirus infections.

In one embodiment, the invention relates to a composition for inducing an immune response in a subject with an asymptomatic (ASYMP) herpesvirus infection. In one embodiment, the composition comprises at least one herpesvirus antigen selected from gD, RR2, VP22, gB, VP16, VP13/14, and VP11/12. In one embodiment, the composition comprises a combination of gD, RR2 and VP22 antigens, or nucleic acid molecules encoding the same. In one embodiment, the composition comprises a RR2 antigen, or nucleic acid molecule encoding the same.

In one embodiment, the invention relates to a composition for inducing an immune response in a subject with a symptomatic (SYMP) herpesvirus infection. In one embodiment, the composition comprises a UL25 antigen, or nucleic acid molecule encoding the same.

Another aspect of the present invention provides immunological compositions, such as vaccines, that are capable of generating in a mammal an immune response against a HSV antigen. In one embodiment, the invention provides nucleic acid vaccines comprised of a nucleic acid capable of expressing one or more HSV antigen in a mammal. The nucleic acid is comprised of a promoter operably linked to a coding sequence that encodes one or more HSV antigen.

The present invention also provides methods for inducing an immune response by administering an effective amount of one or more nucleic acid molecules encoding one or more HSV antigens. In some embodiments, immune response is an anti-HSV immune response. In some embodiments, the immune response is persistent. In some embodiments, the immune response is immediate. In some embodiments, the immune response is systemic.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Fragment" may mean a polypeptide fragment of a longer amino acid sequence that is functional, i.e., has the same intended effect as the full length amino acid sequence. A fragment of an polypeptide may be 100% identical to the full length except missing at least one amino acid from the N and/or C terminal end. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length amino acid sequence, excluding any heterologous peptide sequence added. Fragments may further comprise a fusion at an N terminal or C terminal of the peptide sequence to a heterologous peptide sequence.

"Genetic construct" as used herein refers to the DNA or RNA molecules that comprise a nucleotide sequence which encodes a protein, such as an antigen. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence is expressed.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Immune response" as used herein may mean the activation of a host's immune system, e.g., that of a mammal, in response to the introduction of one or more nucleic acids and/or peptides. The immune response can be in the form of a cellular, mucosal or humoral response, or a combination thereof. The term immune response includes T cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

A "therapeutic" treatment is a treatment administered to a subject who exhibits signs of pathology, for the purpose of diminishing or eliminating those signs.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating and preventing a herpesvirus infection in a subject in need thereof. For example, in certain embodiments, the present invention provides a composition that specifically induces an immune response against herpesvirus. In one embodiment, the composition of the invention boosts the natural immune response against herpesvirus. In one embodiment, the composition of the invention initiates an immune response against one or more herpesvirus antigen.

In one embodiment, the present invention provides a composition for the treatment or prevention of a herpesvirus infection in a subject in need thereof. In one embodiment, the composition comprises at least one isolated herpesvirus antigen, or a fragment thereof. In one embodiment, one or more herpesvirus antigen is selected from gD, RR2, VP22, gB, VP16, VP13/14, VP11/12, UL25 or a combination thereof The composition also encompasses isolated nucleic acids encoding one or more herpesvirus antigen. For example, in one embodiment, the composition comprises an isolated nucleic acid encoding at least one of gD, RR2, VP22, gB, VP16, VP13/14, VP11/12, UL25 or functional fragment or derivative thereof.

In one embodiment, the invention relates to a composition for inducing an immune response in a subject with an asymptomatic (ASYMP) herpesvirus infection. In one embodiment, the composition comprises at least one herpesvirus antigen selected from gD, RR2, VP22, gB, VP16, VP13/14, and VP11/12. In one embodiment, the composition comprises a combination of gD, RR2 and VP22 antigens, or nucleic acid molecules encoding the same. In one embodiment, the composition comprises a RR2 antigen, or nucleic acid molecule encoding the same.

In one embodiment, the invention relates to a composition for inducing an immune response in a subject with a symptomatic (SYMP) herpesvirus infection. In one embodiment, the composition comprises a UL25 antigen, or nucleic acid molecule encoding the same.

In one embodiment, the present invention provides methods for the treatment or prevention of a herpesvirus infection in a subject in need thereof. In one embodiment, the method comprises administering to the subject an effective amount of a composition comprising at least one herpesvirus antigen selected from gD, RR2, VP22, gB, VP16, VP13/14, VP11/12, UL25, or functional fragment or derivative thereof. In certain instances, the method comprises administering a composition comprising an isolated nucleic acid encoding at least one herpesvirus antigen selected from gD, RR2, VP22, gB, VP16, VP13/14, VP11/12, UL25, or functional fragment or derivative thereof. In certain embodiments, the method comprises administering a composition described herein to a subject diagnosed with a herpesvirus infection, at risk for developing a herpesvirus infection, a subject with a latent herpesvirus infection, a subject with recurrent herpesvirus infection and the like.

In one embodiment, the method is used to treat or prevent a herpesvirus infection, including but not limited to herpes simplex type I (HSV1), herpes simplex virus 2 (HSV2), human herpresvirus-3 (HHV-3; varicella zoster virus (VZV), human herpesvirus-4 (HHV-4; Epstein-Barr virus (EBV)), human herpesvirus-5 (HHV-5; Cytomegalovirus (CMV)), human herpesvirus-6 (HHV-6; roseolovirus), human herpes virus-7 (HHV-7), and human herpesvirus-8 (HHV-8; Karposi's sarcoma-associated herpesvirus (KSHV)).

Compositions

In one aspect, the present invention provides a composition that elicits an immune response in a mammal against a herpesvirus (HSV) antigen. In one embodiment, the composition comprises a recombinant nucleic acid sequence encoding an HSV antigen. In one embodiment, the composition can be administered to a subject in need thereof to facilitate in vivo expression of an HSV antigen. In certain embodiments, the herpesvirus antigen is selected from gD, RR2, VP22, gB, VP16, VP13/14, VP11/12, UL25, and a combination thereof.

In one embodiment, the invention provides compositions for inducing an immune response in a subject with an asymptomatic (ASYMP) herpesvirus infection. In one embodiment, the composition comprises at least one herpesvirus antigen selected from gD, RR2, VP22, gB, VP16, VP13/14, and VP11/12. In one embodiment, the composition comprises a combination of gD, RR2 and VP22 antigens, or nucleic acid molecules encoding the same. In one embodiment, the composition comprises a RR2 antigen, or nucleic acid molecule encoding the same.

In one embodiment, the invention provides compositions for inducing an immune response in a subject with a symptomatic (SYMP) herpesvirus infection. In one embodiment, the composition comprises a UL25 antigen, or nucleic acid molecule encoding the same.

Herpesvirus

The herpesvirus genus is divided into three genera: alpha-herpesviruses (e.g., HSV1, HSV2 which causes genital herpes, and varicella-zoster virus (VZV) which causes chickenpox and shingles); beta-herpesviruses (e.g. HHV-6 which causes sixth disease, and HHV-7, which causes roseola infantum); and gamma-herpesviruses (e.g. Epstein-Barr virus which causes mononucleosis and other disease, and HHV-8 which causes Kaposi's sarcoma). The alpha-herpesviruses not only share a similar lifecycle but also have homologous DNA sequences in many of the viral proteins that are essential for viral replication and reactivation.

As described herein, in one embodiment, the present invention provides methods and compositions for immunizing subjects in need thereof with antigens for inducing an immune response against HSV-2. However, the present invention is not limited to the prevention or treatment of HSV2. Rather, the present invention may be used to treat or prevent other herpesviruses.

Protein Antigens

In one embodiment, the HSV antigen comprises a protein, peptide, or functional fragment or derivative thereof. In certain embodiments, the herpesvirus antigen is selected from gD, RR2, VP22, gB, VP16, VP13/14, VP11/12, UL25, and a combination thereof.

The invention should also be construed to include any form of a peptide having substantial homology to a gD, RR2, VP22, gB, VP16, VP13/14, VP11/12 or UL25 peptide disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of a gD, RR2, VP22, gB, VP16, VP13/14, VP11/12 or UL25 peptide disclosed herein.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the HSV antigen.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising an HSV antigen of the invention fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e. are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue. A targeting domain may target the peptide of the invention to a cellular component.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the HSV antigen or chimeric protein fused to the selected protein or marker protein as described herein. Examples of proteins which may be used to prepare fusion proteins include immunoglobulins, glutathione-S-transferase (GST), hemagglutinin (HA), and truncated myc.

A peptide of the invention may be synthesized by conventional techniques. For example, the peptides of the invention may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.).

A peptide of the invention may be prepared by standard chemical or biological means of peptide synthesis. Biological methods include, without limitation, expression of a nucleic acid encoding a peptide in a host cell or in an in vitro translation system.

Biological preparation of a peptide of the invention involves expression of a nucleic acid encoding a desired peptide. An expression cassette comprising such a coding sequence may be used to produce a desired peptide. For example, subclones of a nucleic acid sequence encoding a peptide of the invention can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (2012), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

In the context of an expression vector, the vector can be readily introduced into a host cell, e.g., mammalian, bacterial, yeast or insect cell by any method in the art. Coding sequences for a desired peptide of the invention may be codon optimized based on the codon usage of the intended host cell in order to improve expression efficiency as demonstrated herein. Codon usage patterns can be found in the literature (Nakamura et al., 2000, Nuc Acids Res. 28:292). Representative examples of appropriate hosts include bacterial cells, such as streptococci, staphylococci, *E. coli, Streptomyces* and *Bacillus subtilis* cells; fungal cells, such as yeast cells and Aspergillus cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The expression vector can be transferred into a host cell by physical, biological or chemical means, discussed in detail elsewhere herein.

To ensure that the peptide obtained from either chemical or biological synthetic techniques is the desired peptide, analysis of the peptide composition can be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acids.

Nucleic Acids and Vectors

In one embodiment, the composition of the invention comprises an isolated nucleic acid encoding one or more HSV antigen described herein. For example, in one embodiment, the composition comprises an isolated nucleic acid encoding at least one of gD, RR2, VP22, gB, VP16, VP13/14, VP11/12 and UL25. In one embodiment, the composition comprises an isolated nucleic acid encoding a HSV antigen, or functional fragment or derivative thereof. In one embodiment, the composition comprises an isolated nucleic acid encoding two or more HSV antigens, or functional fragment or derivative thereof.

In one embodiment, the composition comprises at least one isolated nucleic acid encoding at least one HSV antigen, where the HSV antigen is a nucleotide sequence having at least 75%, 80%, 85%, 90%, 95%, 96%, 97%, 98%, or 99% sequence homology to an HSV antigen described herein.

The isolated nucleic acid may comprise any type of nucleic acid, including, but not limited to DNA and RNA. For example, in one embodiment, the composition comprises an isolated DNA molecule, including for example, an isolated cDNA molecule, encoding one or more HSV antigen of the invention, or functional fragment thereof. In one embodiment, the composition comprises an isolated RNA molecule encoding one or more HSV antigen of the invention, or a functional fragment thereof. The isolated nucleic acids may be synthesized using any method known in the art.

The present invention also includes a vector in which the isolated nucleic acid of the present invention is inserted. The art is replete with suitable vectors that are useful in the present invention. Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; BioTechniques, 34: 167-171 (2003). A large variety of such vectors is known in the art and is generally available.

In brief summary, the expression of natural or synthetic nucleic acids encoding an RNA and/or peptide is typically achieved by operably linking a nucleic acid encoding the RNA and/or peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, N.Y.), and in other virology and molecular biology manuals. Viruses, which are useful as vectors include, but are not limited to, retroviruses, adenoviruses, adeno- associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

Pox viral vectors introduce the gene into the cells cytoplasm. Avipox virus vectors result in only a short-term expression of the nucleic acid. Adenovirus vectors, adeno-associated virus vectors and herpes simplex virus (HSV) vectors may be an indication for some invention embodiments. The adenovirus vector results in a shorter-term expression (e.g., less than about a month) than adeno-associated virus, in some embodiments, may exhibit much longer expression. The particular vector chosen will depend upon the target cell and the condition being treated.

In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The selection of appropriate promoters can readily be accomplished. In certain aspects, one would use a high expression promoter. One example of a suitable promoter is the immediate early cytomegalovirus (CMV) promoter sequence. This promoter sequence is a strong constitutive promoter sequence capable of driving high levels of expression of any polynucleotide sequence operatively linked thereto. The Rous sarcoma virus (RSV) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication.

Another example of a suitable promoter is Elongation Growth Factor—1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatinine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the nucleic acid and/or peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant nucleic acid sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In certain embodiments, the composition comprises an isolated cell genetically modified to express one or more isolated nucleic acids and/or peptides described herein. For example, the cell may be an isolated cell transfected or transformed with one or more vectors comprising an isolated nucleic acid sequence encoding one or more HSV antigen.

SAPN Viral Particles

In one embodiment, one or more HSV antigen is incorporated into a self-assembling peptide nanoparticle (SAPN) viral particle for use in a vaccine of the invention. SAPN particles and their use as vaccines or adjuvants are described in U.S. Pat. No. 8/546,337B2, which is hereby incorporated herein in its entirety. Self-assembling protein nanoparticles (SAPN) may be formed by the assembly of one or more polypeptide chains comprising at least one antigen and at least one protein oligomerization domain. The SAPN of the invention may self-assemble into a tetrahedron, a cube, an octahedron, a dodecahedron, or an icosahedron. The SAPN of the invention may be used as an efficient means for presenting one or more antigen.

In one embodiment, the SAPN of the invention comprises at least one of a gD, RR2, RR1, VP22, gB, VP16, VP13/14, VP11/12 and UL25 HSV antigen. In one embodiment, the SAPN of the invention comprises at least two of a gD, RR2, RR1, VP22, gB, VP16, VP13/14, VP11/12 and UL25 antigen. In one embodiment, the SAPN of the invention comprises VP16 and VP22. In one embodiment, the SAPN of the invention comprises RR1 and RR2.

In one embodiment, the SAPN of the invention includes at least one HSV-2 antigen and further comprises flagellin as an adjuvant molecule. SAPN comprising flagellin as an adjuvant are described in U.S. Pat. No. 10/245,318 B2, which is incorporated herein in its entirety.

Pharmaceutical Compositions

The present invention also provides pharmaceutical or immunological compositions comprising one or more of the compositions described herein. The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The immunological composition may further comprise a genetic facilitator agent as described in U.S. Serial No. 021,579 filed Apr. 1, 1994, which is fully incorporated by reference.

The immunological composition may comprise DNA at quantities of from about 1 nanogram to 100 milligrams; about 1 microgram to about 10 milligrams;

or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The immunological composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

The immunological composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The immunological composition can be administered prophylactically or therapeutically. In prophylactic administration, the composition can be administered in an amount sufficient to induce an immune response. In therapeutic applications, the composition is administered to a subject in need thereof in an amount sufficient to elicit a therapeutic effect. An amount adequate to accomplish this is defined as "therapeutically effective dose." Amounts effective for this use will depend on, e.g., the particular composition of the regimen administered, the manner of administration, the stage and severity of the disease, the general state of health of the patient, and the judgment of the prescribing physician.

The immunological composition can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunological composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunological composition can be delivered via a variety of routes. Typical delivery routes include parenteral administration, e.g., intradermal, intramuscular or subcutaneous delivery. Other routes include oral administration, intranasal, and intravaginal routes. The immunological composition can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunological composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunological composition. The formulations may conveniently be presented in unit dosage form, e.g. tablets and sustained release capsules, and may be prepared by any methods well known in the art of pharmacy.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension the composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Methods of Treatment

The present invention provides a method of treating or preventing herpesvirus-mediated infection. In one embodiment, the present invention is directed to methods of increasing an immune response in a subject by administration of an immunological composition comprising at least on HSV antigen, or nucleic acid molecule encoding the same. In one embodiment, the method comprises administering to a subject in need thereof, an effective amount of a composition comprising at least one HSV antigen, or functional fragment or derivative thereof. In one embodiment, the method comprises administering to a subject in need thereof, a composition comprising an isolated nucleic acid encoding at least one HSV antigen, or functional fragment or derivative thereof. In certain embodiments, the method comprises administering a composition described herein to a subject diagnosed with a herpesvirus infection, at risk for developing a herpesvirus infection, a subject with a latent herpesvirus infection, and the like.

In one embodiment, the method is used to treat or prevent a herpesvirus infection, including but not limited to herpes simplex type I (HSV1), herpes simplex virus 2 (HSV2), human herpesvirus-3 (HHV-3; varicella zoster virus (VZV), human herpesvirus-4 (HHV-4; Epstein-Barr virus (EBV)), human herpesvirus-5 (HHV-5; Cytomegalovirus (CMV)), human herpesvirus-6 (HHV-6; roseolovirus), human herpes virus-7 (HHV-7), and human herpesvirus-8 (HHV-8Karposi's sarcoma-associated herpesvirus (KSHV)).

The methods of the invention are also employed for treatment or prevention of diseases and disorders associated with herpesvirus infections, including, but not limited to, labial herpes, genital herpes, herpetic encephalitis, chickenpox, shingles, Bell's palsy, vestibular neuritis, and herpetic neuralgia.

The compositions can be administered in conjunction with (e.g., before, simultaneously or following) one or more therapies. For example, in certain embodiments, the method comprises administration of a composition of the invention in conjunction with an additional anti-herpetic therapy, including, but not limited to a TK inhibitor, a UL30 inhibitor, acyclovir, foscarnet, cidofovir, and derivatives thereof.

The subject to which the composition is administered can have an increased or boosted immune response as compared to a comparator control. In some embodiments, the administered composition can increase or boost the immune response in the subject by at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

The dose of the immunological composition can be between 1 µg to 10 mg active component/kg body weight/time, and can be 20 µg to 10 mg component/kg body weight/time. The number of doses for effective treatment can be 1, 2, 3, 4, 5, 6, 7, 8, 9, 10, or more than 10.

Dosage, toxicity and therapeutic efficacy of the present compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit high therapeutic indices are preferred. While compositions that exhibit toxic side effects may be used, care should be taken to design a delivery system that targets such compositions to the site of affected tissue in order to minimize potential damage to uninfected cells and, thereby, reduce side effects.

The data obtained from cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a composition (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The HSV antigen, or nucleic acid molecule encoding the same, can be delivered to a subject by methods known in the art. In one embodiment, the method comprises genetically modifying a cell to express one or more HSV antigen. For example, in one embodiment, the method comprises contacting a cell with an isolated nucleic acid encoding the HSV antigen.

In one embodiment, the cell is genetically modified in vivo in the subject in whom the therapy is intended. In certain aspects, for in vivo, delivery the nucleic acid is injected directly into the subject. For example, in one embodiment, the nucleic acid is delivered at the site where the composition is required. In vivo nucleic acid transfer techniques include, but is not limited to, transfection with viral vectors such as adenovirus, Herpes simplex I virus, adeno-associated virus), lipid-based systems (useful lipids for lipid-mediated transfer of the gene are DOTMA, DOPE and DC-Chol, for example), naked DNA, and transposon-based expression systems. Exemplary gene therapy protocols see Anderson et al., Science 256:808-813 (1992). See also WO 93/25673 and the references cited therein. In certain embodiments, the method comprises administering of RNA, for example mRNA, directly into the subject (see for example, Zangi et al., 2013 Nature Biotechnology, 31: 898-907).

For ex vivo treatment, an isolated cell is modified in an ex vivo or in vitro environment. In one embodiment, the cell is autologous to a subject to whom the therapy is intended. Alternatively, the cell can be allogeneic, syngeneic, or xenogeneic with respect to the subject. The modified cells may then be administered to the subject directly.

One skilled in the art recognizes that different methods of delivery may be utilized to administer an isolated nucleic acid into a cell. Examples include: (1) methods utilizing physical means, such as electroporation (electricity), a gene gun (physical force) or applying large volumes of a liquid (pressure); and (2) methods wherein the nucleic acid or vector is complexed to another entity, such as a liposome, aggregated protein or transporter molecule.

The amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Genetically modified cells may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

Prime/Pull Vaccine

In one embodiment, one or more HSV antigen of the invention is administered in the form of a prime/pull vaccine. The prime and pull vaccination regimen occurs in two phases. In one embodiment, the first phase (i.e., prime) is administration of a first vaccine composition to elicit a an immune response. In one embodiment, the second phase (i.e., pull) is the recruitment of immune cells to a desired anatomic location by means of a local (e.g., topical) chemokine administration, where such recruited immune cells establish a persistent residence and thereby mediate protective immunity.

In some embodiments, the established immune response directed against an immunogen in the subject, includes activated T cells. In one embodiment, the activated T cells are recruited to a desired anatomic location. In some embodiments, the recruited activated T cells are CD4+ T cells. In other embodiments, the recruited activated T cells are CD8+ T cells. In particular embodiments, the recruited activated T cells are both CD4+ T cells and CD8+ T cells.

In one embodiment, the recruited activated T cells differentiate into memory T cells. In some embodiments, the memory T cells persist in the subject for an extended period of time. In some embodiments, the memory T cells persist in the subject for an extended period of time in the anatomic location to which they were recruited. In some embodiments, the memory T cells persist in the anatomic location to which they were recruited for at least 2 weeks, at least 1 month, at least 2 months, at least 3 months, at least 4 months, at least 5 months, at least 6 months, at least 1 year, at least 2 years, at least 3 years, at least 4 years, or at least 5 years.

In one embodiment, a composition comprising at least one HSV antigen of the invention is administered as a prime vaccine as part of the prime/pull vaccine. In one embodiment, the prime vaccine comprises a composition comprising an SAPN comprising at least one of a gD, RR2, RR1, VP22, gB, VP16, VP13/14, VP11/12 and UL25 HSV antigen. In one embodiment, the SAPN of the invention comprises at least two of a gD, RR2, RR1, VP22, gB, VP16, VP13/14, VP11/12 and UL25 antigen. In one embodiment, the SAPN of the invention comprises VP16 and VP22. In one embodiment, the SAPN of the invention comprises RR1 and RR2. In one embodiment, the SAPN of the invention includes at least one HSV-2 antigen and further comprises flagellin as an adjuvant molecule.

In some embodiments, the T cells are recruited to the desired anatomic location by the local administration of a chemotactic cytokine (i.e., chemokine) at the desired anatomic location. In some embodiments, the chemokine is CXCL9. In other embodiments, the chemokine is CXCL10. In other embodiments, the chemokine is CXCL9. In particular embodiments, the chemokine is a combination of at least two of CXCL9, CXCL10 and CXCL11.

In some embodiments, the two phases of the prime and pull vaccination regimen occur concurrently. In other embodiments, the two phases of the primer and pull vaccination regimen occur in series. In some embodiments, the two phases of the prime and pull vaccination regimen are temporally separate. In other embodiments, the two phases of the prime and pull vaccination regimen temporally overlap.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Therapeutic Mucosal Vaccination of HSV-2 Infected Guinea Pigs with the Ribonucleotide Reductase 2 (RR2) Protein Boosts Antiviral Neutralizing Antibodies and Local Tissue-Resident CD4+ and CD8+ T Cells and Protects Against Recurrent Genital Herpes Genital herpetic disease caused by HSV-2 is one of the most common sexually transmitted diseases (STDs) with a global prevalence of infection predicted to be over 536 million worldwide for individuals between 15-49 years of age (Samandary et al., 2014, Hum Immunol, 75(8):715-29; Looker et al., 2008, Bull World Health Organ, 86(10):805-12; Prodhan et al., 2010, Pediatr Crit Care Med, 11(5):599-602). Besides, HSV-2, HSV-1 infection, that appears more prevalent than HSV-2 (Samandary et al., 2014, Hum Immunol. 2014;75(8):715-29), is also emerging as the cause of close to 50% of genital herpes in Western societies (Sundaram et al., 2009, Int J STD AIDS, 20(1):68; Wald, 2006, Sexually transmitted infections, 82(3):189-90; Mertz et al., 2003, Sex Transm Dis, 30(10):801-2). Moreover, HSV-2/HSV-1 recombinant strains have been recently reported as circulating worldwide (Koelle et al., 2017, Scientific reports, 7:44084). The morbidity, socioeconomic and economic burden associated with genital herpes caused by HSV-1 and HSV-2, the neonatal herpes infection, which results from mother-to-infant vertical transmission that can lead to permanent brain damage; growth defects and disseminated disease or death of newborn, and the alarming relationship between genital herpes and HIV acquisition, all underscore the need for developing a therapeutic genital herpes vaccine (Abu-Raddad et al., 2008, PloS one, 3(5): e2230; Kuo et al., 2014, Vaccine. 2014; 32(50):6733-45). Despite its toll, herpes has generally been seen as a "trivial" disease, and vaccine development has received little attention. A handful of pharmaceutical companies and academic institutions have invested in herpes vaccine research over the past few decades. But none of the efforts panned out, leading many to give up in developing a novel herpes vaccine (Dasgupta and BenMohamed, 2011, Vaccine, 29(35):5824-36; Belshe et al., 2012, The New England journal of medicine, 366:34-43; Stanberry et al., 2002, N Engl J Med, 347(21):1652-61; Van Wagoner et al., 2018, The Journal of infectious diseases, 218(12):1890-9; Bernstein et al., 2017, The Journal of infectious diseases, 215 (6):856-64; Flechtner et al., 2016, Vaccine, 34(44):5314-20). In this investigation, lessons learned from the failure of past clinical trials led to the hypothesis that a therapeutic vaccine encompassing asymptomatic HSV-2 Ags, other than gB and gD, that selectively induce coordinated CD4+ and CD8+ T cells from naturally "protected" asymptomatic women, who despite being infected never develop any recurrent herpetic disease, would halt or at least decrease the frequency and severity of recurrent herpetic disease.

Stress, following immunosuppression, exposure to a variety of physical or psychological/emotional stimulations, triggers HSV to reactivate from latency and recurrent herpetic diseases (Freeman et al., 2007, J Immunol, 179(1): 322-8; Horn et al, 2015, Ann Behav Med, 49(2):187-98; Shirtcliff et al., 2009, Proc Natl Acad Sci USA, 106(8):2963-7; Ortiz et al., 2003, Brain Behav Immun. 2003;17(5):329-38). Asymptomatic HSV-1 and HSV-2 infections are common, pointing to the ability of the immune system to control the symptoms, despite failure to clear the virus (Dasgupta and BenMohamed, 2011, Vaccine, 29(35):5824-36; Kuo et al., 2014, Vaccine, 32(50):6733-45; Dasgupta et al., 2009, Expert Rev Vaccines, 8(8):1023-35). Most genital herpetic disease in symptomatic individuals is due to viral reactivations from latency, rather than to primary acute infection (Dasgupta and BenMohamed, 2011, Vaccine, 29(35):5824-36; Kuo et al., 2014, Vaccine, 32(50):6733-45; Dasgupta et al., 2009, Expert Rev Vaccines, 8(8):1023-35). Over two-third of women (80%) who are seropositive for HSV-2 are asymptomatic (ASYMP), and unaware of their infection (Wald et al., 2006, Sexually transmitted diseases, 33(9):529-33; de Bruyn et al., 2006, Vaccine. 2006;24(7):914-20; Kriesel et al., 2005, The Journal of infectious diseases, 192(1):156-61). They shed and can transmit the reactivated virus, but have no history of recurrent herpetic disease (Zhang et al., 2012, J Immunol, 189(9):4496-509; Chentoufi et al., 2010, Journal of immunology, 184(5):2561-71; Corey et al., 1999, Jama, 282(4):331-40; Langenberg et al., 1999, N Engl J Med, 341(19):1432-8; Chentoufi et al., 2008, J Immunol, 180(1):426-37). In contrast, a small proportion of seropositive women are symptomatic (SYMP) (Tronstein et al., 2011, JAMA, 305(14):1441-9; Wald et al., 2000, N Engl J Med, 342(12):844-50). They have a history of frequent and lifelong episodes of recurrent herpetic disease, often requiring continuous antiviral therapy (Chentoufi et al., 2010, J Virol. 2008; 82(23):11792-802; Dasgupta and BenMohamed, 2011, Vaccine, 29(35):5824-36). It is becoming increasingly clear that naturally acquired herpes immunity in SYMP individuals is not sufficient for protection against virus reactivation from DRG and virus infection and/or disease at the genital tract (Rouse et al., 2006, Immunological reviews, 212:272-86; Cunningham et al., 2006, The Journal of infectious diseases, 194 Suppl 1:S11-8; MasCasullo et al., 2005, Viral Immunol, 18(4):595-606; Koelle and Ghiasi, 2005, Curr Eye Res, 30(11):929-42; Jones and Cunningham, 2004, Herpes, 11(1):12-7). This implies that a successful herpes vaccine must be able to either boost the natural immune responses, or initiate a protective immune mechanism that does not occur following natural exposure to the virus (Srivastava et al., 2015, Invest Ophthalmol Vis Sci, 56(6):4013-28; Khan et al., 2014, Hum Vaccin Immunother, 10(4):945-63; Dervillez et al., 2012, Future virology, 7(4):371-8; Chentoufi et al., 2012, Clin Dev Immunol, 2012:187585; Kuo et al., 2014, Vaccine, 32(50):6733-45; Dasgupta et al., 2009, Expert Rev Vaccines, 8(8):1023-35). Such protective immune responses might be directed against Ags/epitopes, similar to those seen in naturally acquired protective immunity in ASYMP individuals (Dasgupta et al., 2009, Expert Rev Vaccines, 8(8):1023-35). The correct response to the recent "failures" of clinical HSV vaccine trials using one or two HSV glycoproteins is to increase the understanding of the genital herpes mucosal immune system and to encourage testing of novel HSV-1 Ags and Ag-delivery approaches.

In the present study, gD, RR2, VP22, gB, VP16, VP13/14, VP11/12 protein Ags were selected, as being highly recognized by T cells from asymptomatic individuals. The safety, immunogenicity and protective efficacy of these Ags was compared in a pre-clinical therapeutic vaccine trial using the guinea pig model of recurrent genital herpes. Compared to the d15-29, a whole HSV-2 live vaccine that was recently tested in clinical trials (Diaz et al., 2018, Virology, 513:129-35), the experiments presented herein demonstrate that therapeutic immunization with gD, VP22 or RR2 protein produced significant protection against recurrent genital herpes. While RR2 has been previously reported as a major target of HSV-2-specific CD8+ T cells in humans (Long et al., 2014, Virology, 464-465:296-311), its B- CD4+ and CD8+ T-cells immunogenicity and therapeutic vaccine efficacy against recurrent genital herpes has never been tested. The present study demonstrates that the HSV-2 RR2 antigen: (i) boosts both neutralizing antibodies, that appear to cross-react with gB and gD, and CD4+ and CD8+ T cells in an infected host; and (ii) is a protective therapeutic antigen that induced CD4+ and CD8+ T cell dependent protective immunity that appears relied on an increase number of functional vaginal mucosa-resident IFN-γ-producing CRTAM+CFSE+ CD4+ and CRTAM+CFSE+CD8+ T cells. The HSV-2 RR2 antigen, therefore, constitute a viable B- and T-cell candidate antigen to be incorporated in a future genital herpes therapeutic mucosal vaccines. In a recent 1/2a phase clinical trial, a candidate therapeutic HSV-2 vaccine formulation designated GEN-003, made by a mixture of a fragment of infected cell protein 4 (ICP4.2), a deletion mutant of gD2 (gD2ATMR), and Matrix-M2 adjuvant appeared to: (1) boost the HSV-2-specific antibody and T cell responses, as measured in the peripheral blood; and (2) improve viral shedding and lesion rates (Van Wagoner et al., 2018, The Journal of infectious diseases, 218(12):1890-9; Bernstein et al., 2017, The Journal of infectious diseases, 215(6):856-64; Flechtner et al., 2016, Vaccine, 34(44):5314-20). The same level of protective immunity has yet to be reproduced in a larger phase III clinical trial.

The HSV-2 ribonucleotide reductase (RR) consists of two heterologous protein subunits. The small subunit (RR2) is a 38-kDa protein encoded by the UL40 gene and the large subunit (RR1), designated ICP10, is a 140-kDa protein encoded by the UL39 gene (Smith et al., 1998, J Virol, 72(11):9131-41). The RR2 is a major target of HSV-2-specific CD8+ T cells in humans (Long et al., Virology, 464-465:296-311). Hensel et al., recently reported that a preventive prophylactic vaccine based on a combination of UL40 and the extracellular portion of the gD (gDt) protected non-infected guinea pig model from an intravaginal HSV2 challenge (Hansel et al., 2017, J Virol, 91(9)). Unclear whether the observed prophylactic protection was due to UL40 or to gD, since immunization with single Ag that formed that combination was not compared in that study. The present study, extend those studies by demonstrating that a therapeutic vaccination of HSV-2 infected guinea pigs with RR2 protein alone, boosted gB- and gD-cross-reactive neutralizing antibodies and enhanced the numbers of functional IFN-γ$^+$CRTAM$^+$CFSE$^+$CD4$^+$ and IFN-γ$^+$CRTAM$^+$CFSE$^+$CD8$^+$T cells within the VM tissues. These robust local B- and T-cell responses were associated with a significant reduction in both virus shedding and in the severity and frequency of recurrent genital herpes lesions. These pre-clinical findings suggest the HSV-2 RR2 protein as a viable candidate to be incorporated in the next genital herpes therapeutic mucosal vaccine to be tested in the clinic. Compared to the intramuscular route, the intravaginal route proved to be far better in boosting tissue-resident HSV-specific CD4+ and CD8+ T cells detected at the genital epithelium. The mechanisms that lead to superiority of intravaginal and intranasal routes remain to be elucidated. Nevertheless, it is surprising that the protective efficacy of RR2 protein-based subunit vaccine delivered intravaginally in HSV-2 infected guinea pigs was comparable to that induced with the d15-29, a whole HSV-2 live vaccine that was recently tested in a phase I clinical trial (Diaz et al., 2018, Virology, 513:129-35). The d15-29 live vaccine completes only part of the herpes lytic cycle, without spreading to other cells, while expressing many HSV-2 Ags (Diaz et al., 2018, Virology, 513:129-35).

Acyclovir reduces/suppresses recurrent symptomatic disease, asymptomatic shedding, and lateral transmission to some extent, however does not clear the infection or stop recurrent disease (Kuo et al., 2014, Vaccine, 32(50):6733-45; Dasgupta et al., 2009, Expert Rev Vaccines, 8(8):1023-35). This emphasizes the need for a therapeutic vaccine (more than a prophylactic vaccine), which can boost the immune system to decrease virus shedding and reduce or eliminate herpes pathology. At present, no FDA-approved therapeutic vaccines are available. Historically, developing therapeutic vaccines has been more difficult than developing prophylactic vaccines. Prophylactic herpes vaccines have focused primarily on eliciting antibody responses (Dasgupta et al., 2009, Expert Rev Vaccines, 8(8):1023-35). In contrast, therapeutic vaccines require induction of both antibodies and potent local CD4+ and CD8+ T cell responses at the sites of infections (i.e. vaginal muco-cutaneous tissue and DRG). Developing a T cell-based therapeutic vaccines is often confronted with multiple immune evasion mechanisms developed by the virus to adapt to its host (Kuo et al., 2014, Vaccine, 32(50):6733-45). Among the immune evasion mechanisms is the exhaustion of antiviral memory and effector CD4+ and CD8+ T cells (Chentoufi et al., 2011, J Virol. 2011; 85(17):9127-38; Allen et al., 2011, J Virol, 85(9):4184-97; Mott et al., 2009, J Virol. 2009; 83(5):2246-54). Total or partial loss of T cell function (dysfunction) occurs following repetitive HSV latent/reactivation cycles (Frank et al., 2010, J Immunol, 184(1):277-86; Allen et al., 2010, J Virol, 84(23):12315-24; Chentoufi et al., 2012, Viral Immunol, 25(3):204-15). When T cell dysfunction develops under conditions of repetitive exposure to antigens it is called exhaustion (reviewed in Wherry, 2011, Nat Immunol. 2011; 12(6):492-9) and is usually linked with expression of T cell co-inhibitory receptors: PD-1, TIM-3, LAG3 (CD223), TIGIT, PSGL-1, 2B4 (CD244), GITR, CTLA-4 (CD152), CD160, and BTLA (CD272) (reviewed in Day et al., 2006, Nature, 443(7109):350-4; Anderson et al., 2016, Immunity. 2016; 44(5):989-1004). In humans, tissue-resident CD8+ T cells express PD-1 and appear to be dysfunctional (van Velzen et al., 2009, J Immunol, 183(4):2456-61). Similar to humans, most tissue-resident effector CD8+ T cells simultaneously express high levels of 2 to 3 immune checkpoint receptors (e.g., PD-1, TIM-3 and LAG-3). This report demonstrates that differential expression of exhaustion markers PD-1 and TIM-3 on guinea pigs memory CD4+ and CD8+ T cells is associated with a lack of protective immunity against recurrent genital herpes. The mechanisms that lead to an increased expression of PD-1 and TIM-3 on vaginal mucosa-resident CD4+ and CD8+ T cells remains to be elucidated. It is likely that repetitive/sporadic virus reactivations in non-protected animals led to persistent antigenic stimulations of T cells at the vaginal mucosa and this caused the observed phenotypic and functional exhaustion of tissue-resident antiviral CD4+ and CD8+ T cells. Nevertheless, these results suggest a single or combined immune checkpoint blockade using anti-PD-1 and/or anti-TIM-3 mAbs would reverse the exhaustion of antiviral tissue-resident CD4+ and CD8+ T cells at the vaginal mucosa, and hence restore their protective function. The prospect of a novel RR1 and RR2-based therapeutic herpes vaccine combined with the immune checkpoints blockade would likely increase the efficacy and longevity of protection against recurrent herpes. Therapeutic subunit vaccination, using three of the moderately protective Ags tested in this study (i.e. VP16, VP11/12 and VP13/14) combined with immune checkpoints blockade (i.e. PD-1 and/or TIM-3) are currently being tested using the guinea pig model of recurrent genital herpes.

A reliable small animal model is the ultimate key factor for pre-clinical testing of the therapeutic efficacy of the growing numbers of herpes vaccine candidates against spontaneous herpes reactivation and recurrent disease, yet its relevance has been often overlooked. The use of mouse models of HSV-2 infection is limited by the lack of spontaneous reactivation of the virus from latently infected dorsal root ganglion (DRG) and hence absence of recurrent genital herpes. In contrast, spontaneous reactivation occurs in HSV-2 infected guinea pigs which develop clinical and pathological features of recurrent genital herpes that are similar to those seen in human infections. The appearance and evolution of genital lesions, histologic changes in the genital epithelium and nerve tissues, and establishment of latent virus infection in the DRG with the potential for reactivation, all mimic the human disease. Since, analyses of human blood-derived T cells may not always reflect tissue-resident T cells, the guinea pig represents the gold standard model to determine the contribution of the vaginal mucosa-tissues-resident CD4+ and CD8+ cells versus blood-derived CD8+ T cells in protection against recurrent genital herpes (White et al., 2001, The Journal of infectious diseases, 183(6):977-83). The guinea pig model allowed to speed up testing whether therapeutic vaccine candidates, encompassing asymptomatic protein Ags (e.g., RR2 and UL49) decrease level of latency in DRG, spontaneous reactivation from sensory neurons of DRG, virus shedding in genital tract and recurrent genital herpetic disease. It is worth emphasizing that, similar to d15-29 vaccine, the RR2 subunit vaccine significantly boosted the numbers of functional IFN-γ +CRTAM+CFSE+CD4+ and IFN-γ+CRTAM+CFSE+CD8+ T cells that were localized to healed sites of the vaginal mucocutaneous tissues and this was associated with a significant decrease in virus shedding and a reduction in the severity and frequency of recurrent genital herpes lesions.

Considering the wealth of data addressing the antibody responses to herpes infections/immunizations in the guinea pig model, it is surprising how few reports exist characterizing the phenotype, function and exhaustion of CD4+ and CD8+ T cells in this model. One limitation is the unavailability of monoclonal antibodies (mAbs) specific to guinea pigs immune cell surface CD, cytokines, chemokines and receptors. Compared to mice, relatively few immunological reagents are available to characterize CD4+ and CD8+ T cells in guinea pigs. Herein, new immunological reagents and novel approaches are described that quantitatively and qualitatively help characterize the phenotype, function and exhaustion of CD4+ and CD8+ T cell responses both systemically and as they occur in the female reproductive tract of the infected and vaccinated guinea pigs. IFN-γ-ELISpot, CFSE-based proliferation, surface markers of T cell activation (CRTAM) and T cell exhaustion (PD-1 and TIM-3), intracellular cytokines. Moreover, a quantitative PCR (qPCR) techniques to detect and quantify recurrent HSV-2 shedding have been optimized in the guinea pig model. These immunological reagents and novel approaches are useful to study infection, immunity and immune-pathogenesis of many infectious and allergic diseases in the guinea pig model (Wodal et al., 2015, PloS one. 2015; 10(2): e0113963; Swanson et al., 2015, Vaccine. 2015; 33(32): 4013-8; Gillis et al., 2014, Vaccine. 2014; 32(31):3963-70), besides genital herpes infection and disease.

In summary, this study represents the first in-depth evidence that intravaginal immunization of HSV-2 infected guinea pigs with a recombinantly expressed HSV-2 RR2 protein in CpG and Alum adjuvant safely boosted a coordinated and broad-spectrum of B- and T-cells responses, including gB and gD-cross reactive neutralizing antibodies and tissue-resident IFN-γ-producing CD4+ and CD8+ T cells that localized to healed sites of the vaginal mucocutaneous tissues. The strong B- and T-cell immunogenicity of RR2-based therapeutic vaccine was associated to a significant protection against recurrent genital herpes. In the context of limited success of recent herpes clinical vaccines delivered parenterally, this is a rather interesting finding since antiviral local CD4+ and CD8+ T cell responses within the infected vaginal mucocutaneous tissue might be sub-optimal due to the unique vaginal immune environment (Mestecky et al., 1999, The Journal of infectious diseases, 179 Suppl 3:S470-4). The present findings are encouraging as they offer relatively low-cost mucosal routes to provide a T-cell based vaccine for clinical trials. The T cell epitopes from the RR2 that are protective in clinical trials remain to be determined. Nevertheless, the findings support the Ag selection strategy and suggest that vaccination with "asymptomatic" protein Ags will likely boost the number and function of CD4+ and CD8+ T cells that would prevent (or at least reduce) virus reactivation and, hence, protect against recurrent genital herpes. The findings lay the ground for an accessible mucosal subunit therapeutic vaccine approach to decrease virus shedding and reduce or eliminate genital herpes pathology, and presumably other sexually transmitted infectious diseases.

The methods are now described.

Human Study Population

During the last fifteen years (i.e. January 2003 to October 2018), 925 individuals were screened for HSV-1 and HSV-2 seropositivity. Five hundred eighty-seven were White, 338 were non-White (African, Asian, Hispanic and other), 467 were female, and 458 were male. Among this sample, a cohort of 308 immuno-competent individuals, ranging from 21-69 years old (median 45), were seropositive for HSV-2. All patients were negative for HIV and HBV, with no history of immunodeficiency. Two hundred and seventy-eight patients were healthy and defined as asymptomatic (ASYMP). These patients never had any herpes disease (genital, oro-facial, dermal or ocular) based on self-reporting and clinical examination. Even a single episode of any herpetic disease would exclude the individual from this group. The remaining 30 patients were defined as HSV-seropositive symptomatic (SYMP) individuals who suffered from frequent and severe recurrent genital lesions. Patients were also excluded if they: (1) had an active genital (or elsewhere) herpetic lesion, or had one within the past 30 days; (2) pregnant or breastfeeding; or (3) were on Acyclovir and other related anti-viral drugs or any other immunosuppressive drugs at the time of blood draw. SYMP and ASYMP groups were matched for age, gender, serological status and race. Among this large cohort, 20 SYMP and 20 ASYMP women were enrolled in the current study (Table 1). Ten age- and gender-matched healthy controls were enrolled that were seronegative for both HSV-1 and HSV-2 and who had no history of herpes diseases.

TABLE 1

Cohorts of HLA-A*02:01 positive, HSV seropositive Symptomatic and Asymptomatic individuals enrolled in this study

| Subject-level Characteristic | All Subjects (n = 50) |
|---|---|
| Gender [no.(%)]: | |
| Female | 26 (52%) |
| Male | 24 (48%) |
| Race [no.(%)]: | |
| Caucasian | 21 (42%) |
| Non Caucasian | 29 (58%) |
| Age [median (range) yr.]: | 23 (22-66 yr.) |
| HSV status [no. (%)]: | |
| HSV-1-seropositive | 40 (80%) |
| HSV-2-seropositive | 00 (0%) |
| HSV-1- & 2-seropositive | 00 (0%) |
| HSV-seronegative | 10 (20%) |
| HLA [no.(%)] | |
| HLA-A*02:01-positive | 50 (100%) |
| HLA-A*02:01-negative | 00 (0%) |
| Herpes Disease Status [no.(%)] | |
| Asymptomatic (ASYMP) | 20 (40%) |
| Symptomatic (SYMP) | 20 (40%) |

HSV Specific Serotyping

The sera collected from random donors were tested for anti-HSV antibodies. ELISA was performed on sterile 96-well flat-bottom microplates coated with the HSV-2 antigen in coating buffer overnight at 4° C. The next day, plates were washed with PBS-1% Tween 20 (PBS) five times, and nonspecific binding was blocked by incubating with a 5% solution of skimmed milk in PBS (200 μl/well) at 4° C. for 1 hour at room temperature (RT). The microplates were washed three times with PBS-Tween and incubated with various sera at 37° C. for two hours. Following five washes, biotinylated rabbit anti-human IgG, diluted 1:20,000 with PBST, was incubated at 37° C. for two hours. After five washes, streptavidin-peroxidase was added at a 1:5,000 dilution and incubated for 30 minutes at RT. After five additional washes, the color was developed by adding 100 μl of TMB substrate. The mixture was incubated for 5-15 minutes at RT in the dark. The reaction was terminated by adding 1 M $H_2SO_4$. The absorbance was measured at 450 nm.

Peripheral Blood Mononuclear Cells Isolation

Individuals (negative for HIV, HBV, and with or without any HSV infection history) were recruited at the UC Irvine Institute for Clinical and Translational Science (ICTS). 100 mL of blood was drawn into yellow-top Vacutainer® Tubes (Becton Dickinson). The serum was isolated and stored at −80° C. for the detection of anti-HSV-1 and anti-HSV-2 antibodies, as previously described (Chentoufi et al., 2008, J Virol, 82(23):11792-802). Peripheral blood mononuclear cells (PBMC) were isolated by gradient centrifugation using leukocyte separation medium (Life Sciences, Tewksbury, Mass.). The cells were then washed in PBS and suspended in complete culture medium consisting of RPMI1640, 10% FBS (Bio-Products, Woodland, Calif.) supplemented with 1× penicillin/streptomycin/L-glutamine, 1× sodium pyruvate, 1× non-essential amino acids, and 50 μM of 2-mercaptoethanol (Life Technologies, Rockville, Md.).

Flow Cytometry Assays

Peripheral blood mononuclear cells were analyzed by flow cytometry after staining with fluorochrome-conjugated human-specific mAbs. The following anti-human antibodies were used for the flow cytometry assays: CD3 (clone SK7) PE-Cy7, CD4 (clone DE54), CD8 (clone SK1), CD45RA FITC, CD62L allophycocyanin, IFN-g Alexa Fluor 647, Granzyme B (clone GB11) A647, CD107a (clone H4A3) FITC, CD107b (clone H4B4) FITC (BioLegend, San Diego, Calif.), and Granzyme K (clone G3H69). Surface-staining mAbs against various cell markers were added to a total of 1×10$^6$ PBMCs in PBS containing 1% FBS and 0.1% sodium azide (FACS buffer) for 45 minutes at 4° C. After the cells were washed with FACS buffer, they were subsequently permeabilized for 20 minutes on ice using a Cytofix/Cytoperm kit (BD Biosciences) and then washed twice with Perm/Wash buffer (BD Biosciences). Intracellular cytokine-staining mAbs were added to the cells, and the mixture was incubated for 45 minutes on ice in the dark. The cells were washed with Perm/Wash buffer and FACS buffer and subsequently fixed in PBS containing 2% paraformaldehyde (Sigma-Aldrich, St. Louis, Mo.). For each sample, 100,000 total events were acquired on the BD LSRII. Ab capture beads (BD Biosciences) were used as individual compensation tubes for each fluorophore in the experiment. To define positive and negative populations, isotype control mAbs were used for each fluorophore and further optimized gating by examining known negative cell populations for background expression levels. The gating strategy was similar to that used previously (Chentoufi et al., 2008, J Immunol, 180(1):426-37). Briefly, the gating was for single cells, viable cells (Aqua Blue), lymphocytes, CD3$^+$CD4$^+$ cells and CD3$^+$CD8$^+$ cells. Data analysis was performed using the FlowJo software (Version 10.4.2, TreeStar, Ashland, Oreg.). Statistical analyses were done using the GraphPad Prism (Version 5, La Jolla, Calif.).

Animals

Female guinea pigs (Hartley strain, Charles River Laboratories, San Diego, Calif.) weighing 275-350 g (5-6 weeks old) were housed at the University of California, Irvine vivarium. The number of animals required per group for each experiment was calculated based on experiments using animal models in spontaneous and induced recurrent herpes infection and disease. A group size of 10 had 90% power to detect a difference of two-fold or higher between experimental group means with a significance level of 0.05.

Vaccine Candidates

Eight recombinantly expressed protein antigens were used from HSV-2: gD, RR2, VP22, gB, VP16, VP13/14, VP11/12 and UL25, selected as highly recognized by T cells from naturally "protected" asymptomatic individuals (Table 1). The replication defective HSV-2 dl5-29 mutant virus (i.e. DL5-29 vaccine) was used as a positive control.

Infection and Immunization of Guinea Pigs

Throughout this study, the MS strain of HSV-2 was used. Guinea pigs (n=11) were infected intravaginally with $5\times10^5$ pfu of HSV-2 (strain MS). Once acute infection was resolved, latently infected animals were then vaccinated intramuscularly twice, in the right hind calf muscle on day 15 and on day 25 post-infection. Animals were immunized on day 15 with 20 µg and on day 25 with 10 µg of various HSV-2 proteins (gD, RR1, RR2, VP22, gB, VP16, VP13/14, VP11/12 and UL25) mixed with 100 µg CpG/guinea pig and 150 µg alum. Animals were mock-immunized with the CpG oligonucleotide (5'-TCGTCGTTGTCGTTTTGTCGTT-3') (SEQ ID NO:1) (Trilink Inc., Santa Fe Springs, Calif.) using 100 µg CpG/guinea pig and 150 µg alum (Alhydrogel, Accurate Chemical and Scientific Corp., Westbury, N.Y.)

Monitoring of Primary or Recurrent HSV-2 Disease in Guinea Pigs

Guinea pigs were examined for vaginal lesions and were recorded for each individual animal on a daily basis starting right after second immunization on a scale of 0 to 4, where 0 reflects no disease, 1 reflects redness, 2 reflects a single lesion, 3 reflects coalesced lesions, and 4 reflects ulcerated lesions.

Quantification of Infectious Virus

Vaginal swabs were collected daily using a Dacron swab (type 1; Spectrum Laboratories, Los Angeles, Calif.) starting from day 35 until day 65 post-challenge. Individual swabs were transferred to a 2 mL sterile cryogenic vial containing 1 ml culture medium and stored at −80° C. until use. The HSV-2 DNA copy numbers in the individual samples were determined by quantitative PCR.

Real-time qPCR on Guinea Pig Vaginal Swabs DNA was isolated from 300 µl of guinea pig vaginal swab material using DNeasy blood and tissue kits (Qiagen). HSV-2 DNA copy number was determined using purified HSV-2 DNA (Advanced Biotechnologies, Columbia, Md.) and based on a standard curve that was generated with 50,000, 5,000, 500, 50, and 5 copies of DNA and run in triplicates. Each guinea pig sample was analyzed in duplicate. Samples with <150 copies/ml by 40 cycles or only positive in one of two wells were reported as negative. Primer and probe sequences for HSV-2 Us9 were: primer forward, 5'-GGCAGAAGCCTAC-TACTCGGAAA-3'(SEQ ID NO:2), and reverse 5'-CCATGCGCACGAGGAAGT-3' (SEQ ID NO:3), and probe with reporter dye 5'-FAM-CGAGGCCGCCAAC-minor groove binder 3' non-fluorescent quencher (MGBNFQ)-3' (SEQ ID NO:4) (FAM, 6-carboxyfluorescein). All reactions were performed using TaqMan gene expression master mix (Applied Biosystems) and data was collected and analyzed on StepOnePlus real time PCR system.

ELISA and Neutralizing Antibodies

Blood (5 mL) was drawn from each guinea pig into yellow-top Vacutainer® Tubes (Becton Dickinson, USA). Sera were isolated by centrifugation for 10 minutes at 800×g. For measuring antigen-specific antibody titer in the serum of immunized guinea pigs, ELISA plates were coated with 50 ng of individual HSV-2 proteins, incubated with guinea pig serum at a 1:1000 dilution, followed by HRP-conjugated anti-guinea pig IgG. For measuring the binding affinity of antigen-specific antibodies to the HSV-2 MS strain, ELISA plates were coated overnight at 4° C. with $1\times10^4$ PFU/well of heat inactivated MS strain and incubated with respective guinea pig serum at a 1:1000 dilution, followed by HRP-conjugated anti-guinea pig IgG. For competitive inhibition assays, antigen specific sera, diluted 1:100, were incubated overnight at 4° C. with test inhibitory peptides at concentrations ranging from $10^{-1}$ to $10^{-5}$ ng/ml. These samples were then processed as standard ELSA assays, using 1 mg of respective antigen coated plates. Results for each peptide tested at different concentrations were expressed as percentage of inhibition, calculated as follows: % inhibition=($OD_{450}$ (immune serum incubated with test peptide at test concentration)−$OD_{450}$ (background, serum dilution buffer)/($OD_{450}$ (immune serum incubated in the absence of peptide)−$OD_{450}$ (background, serum dilution buffer))×100. Neutralizing antibody titers were determined by incubating 100 PFU of HSV-2 strain MS with serial dilutions of serum starting at 1:40 for 1 hour at 37° C. The endpoint neutralization titer was determined by the plaque assay on RS cells and was calculated as the serum dilution that reduced the number of plaques by 50% compared with PBS controls.

Splenocytes Isolation

Spleens were harvested from guinea pigs at 80 days post infection. Spleens were placed in 10 ml of cold PBS with 10% fetal bovine serum (FBS) and 2× antibiotic-antimycotic (Life Technologies, Carlsbad, Calif.). Spleens were minced finely and sequentially passed through a 100 µm mesh and a 70 µm mesh (BD Biosciences, San Jose, Calif.). Cells were then pelleted via centrifugation at 400×g for 10 minutes at 4° C. Red blood cells were lysed using a lysis buffer (ammonium chloride) and washed again. Isolated splenocytes were diluted to $1\times10^6$ viable cells per ml in RPMI media with 10% (v/v) FBS and 2×antibiotic-antimycotic. Viability was determined by trypan blue staining.

Isolation of Lymphocytes from Guinea pig's Vaginal Mucosa

Vaginal mucosa was removed from the guinea pigs. The genital tract was minced into fine pieces and then the tissue pieces were then transferred into a new tube with fresh RPMI-10 containing collagenase and digested at 37° C. for 2 hours on a rocker set to vigorously stir the tissue. The digested tissue suspension was then passed through a 100 µm cell strainer on ice, followed by centrifugation. Lymphocytes in the cell pellets were separated using Percoll gradients by centrifugation at 900×g, at room temperature, for 20 minutes with the brake off The lymphocytes at the interface layer between 40% and 70% Percoll layers were harvested, washed with RPMI 1:3 and spun down at 740×g.

Flow Cytometry Analysis

Vaginal mucosa cells and splenocytes were analyzed by flow cytometry. The following antibodies were used: Mouse anti-guinea pig CD8 (clone MCA752F, Bio-Rad Laboratories, Hercules, Calif.), mouse anti-guinea pig CD4 (clone MCA749PE, Bio-Rad Laboratories), anti-mouse CRTAM (clone 11-5, Biolegend), hamster anti-mouse PD-1 clone J43, BD Biosciences, San Jose, Calif.), and human Tim-3 (clone F38-2E2, BD Biosciences, San Jose, Calif.). For surface staining, mAbs against various cell markers were added to a total of $1\times10^6$ cells in phosphate-buffered saline containing 1% FBS and 0.1% sodium azide (fluorescence-activated cell sorter [FACS] buffer) and left for 45 minutes at 4° C. At the end of the incubation period, the cells were washed twice with FACS buffer. A total of 100,000 events were acquired by the LSRII (Becton Dickinson, Mountain View, Calif.) followed by analysis using FlowJo software (TreeStar, Ashland, Oreg.).

T Cell Proliferation Assay

CD8+ T cell proliferation was measured using a CFSE assay. Briefly, splenocytes were labeled with CFSE (2.5 μM; Molecular Probes) in 1× PBS at room temperature. Cold FCS was added, and cells were washed extensively with RPMI 1640 plus 10% FCS. CFSE-labeled cells were either incubated or not with various individual HSV-2 proteins (10 μg/ml) for 6 days. Cells were then washed and stained with PE-conjugated mAbs specific to guinea pig CD8 molecules. The numbers of dividing CD8+ T cells per 300,000 total cells were analyzed by FACS.

ELISpot Assay

All reagents used were filtered through a 0.22 μm filter. Wells of 96-well Multiscreen HTS Plates (Millipore, Billerica, Mass.) were pre-wet with 70% methanol and then coated with 100 μl primary anti-IFN-g antibody solution (10 μg/ml in PBS, pH 7.4, V-E4) OVN at 4° C. (Schultheis et al., 2017, Vaccine, 35(1):61-70). After washing, nonspecific binding was blocked with 200 μl of RPMI media with 10% (v/v) FBS for 2 hours at room temperature. Following the blockade, 5×10$^5$ vaginal mucosa cells and splenocytes in 100 μl of RPMI were mixed with 50 μl stimulant (no stimulation or with individual HSV-2 proteins at a final concentration of 10 μg/ml) in duplicate. After incubation in humidified 5% $CO_2$ at 37° C. for 48 hours, cells were removed by washing (using PBS and PBS-Tween 0.02% solution) and 100 μl of biotinylated secondary anti-IFN-g antibody (2 μg/ml, N-G3) in blocking buffer (PBS 0.5% BSA) was added to each well. Following a 2-hour incubation and washing, alkaline phosphatase-conjugated streptavidin (SEL002, R&D Systems Inc., Minneapolis, Minn.) was diluted 1:100 and wells were incubated with 100 μl for 1 hour at room temperature. Following washing, wells were incubated for 1 hour at room temperature with 100 μl of BCIP/NBT detection reagent (SEL002, R&D Systems, Inc.) and spots counted with an automated ELISpot Reader System (ImmunoSpot reader, Cellular Technology).

Statistical Analyses

Data for each assay were compared by analysis of variance (ANOVA) and Student's t test using GraphPad Prism version 5 (La Jolla, Calif.). Differences between the groups were identified by ANOVA and multiple comparison procedures, as described (Srivastava et al., 2018, J Immunol, 200(8):2915-2926; Srivastava et al., 2018, J Immunol. 2018; 200(8):2915-26; Srivastava et al.,2018, J Immunol, 201(8): 2315-30; Lopes et al., 2018, J Virol, 92(8); Khan et al., 2018, J Virol, 92(16)). Data are expressed as the mean±SD. Results were considered statistically significant at $P<0.05$.

The results of the experiments are now described.

Probing the Whole HSV-2 ORFome by T Cells from Seropositive Asymptomatic vs. Symptomatic Individuals Identifies Eight Immunodominant "Asymptomatic" Protein Antigens The characteristics of the HSV-2-seropositive symptomatic (SYMP) and HSV-2-seropositive asymptomatic (ASYMP) population used in the present study, with respect to gender, age, HSV-1/HSV-2 seropositivity and status of genital herpetic disease are presented in Table 1. The HSV-2-seropositive individuals were divided into two age-and gender-matched groups: (i) 10 ASYMP individuals who, despite being infected, never had any clinically detectable herpes disease; and (ii) 10 SYMP individuals with a history of numerous episodes of clinically documented recurrent genital herpes. Ten age- and gender-matched HSV-1 and HSV-2 seronegative healthy subjects (NEG) were enrolled as controls.

A near complete collection of the 84+ open reading frames (ORFs) of HSV-2 has been cloned and corresponding proteins expressed individually, as reported (Dasgupta et al., 2012, J Virol, 86(8):4358-69; Kalantari-Dehaghi et al., 2012, J Virol. 2012; 86(8):4328-39). A genome-wide scan of this HSV-2 ORFome was performed using peripheral blood derived CD4+ and CD8+ T cells from the above clinically defined SYMP and ASYMP individuals. This resulted in identification of several "asymptomatic" regions that were specifically recognized by CD4+ and CD8+ T cells from ASYMP individuals (FIG. 1). To rank the "symptomatic" and "asymptomatic" protein antigens, both the frequency and the intensity of CD4+ and CD8+ T cell responses specific to the antigens of HSV-2 ORFome were determined. An antigen is designated "asymptomatic" Ag when it is frequently recognized by CD4+ and CD8+ T cells from seropositive ASYMP individuals with high-to-medium intensity. Inversely, an antigen is designated "symptomatic" Ag when it is frequently recognized by CD4+ and CD8+ T cells from seropositive SYMP individuals with high-to-medium intensity.

Figure 1B:
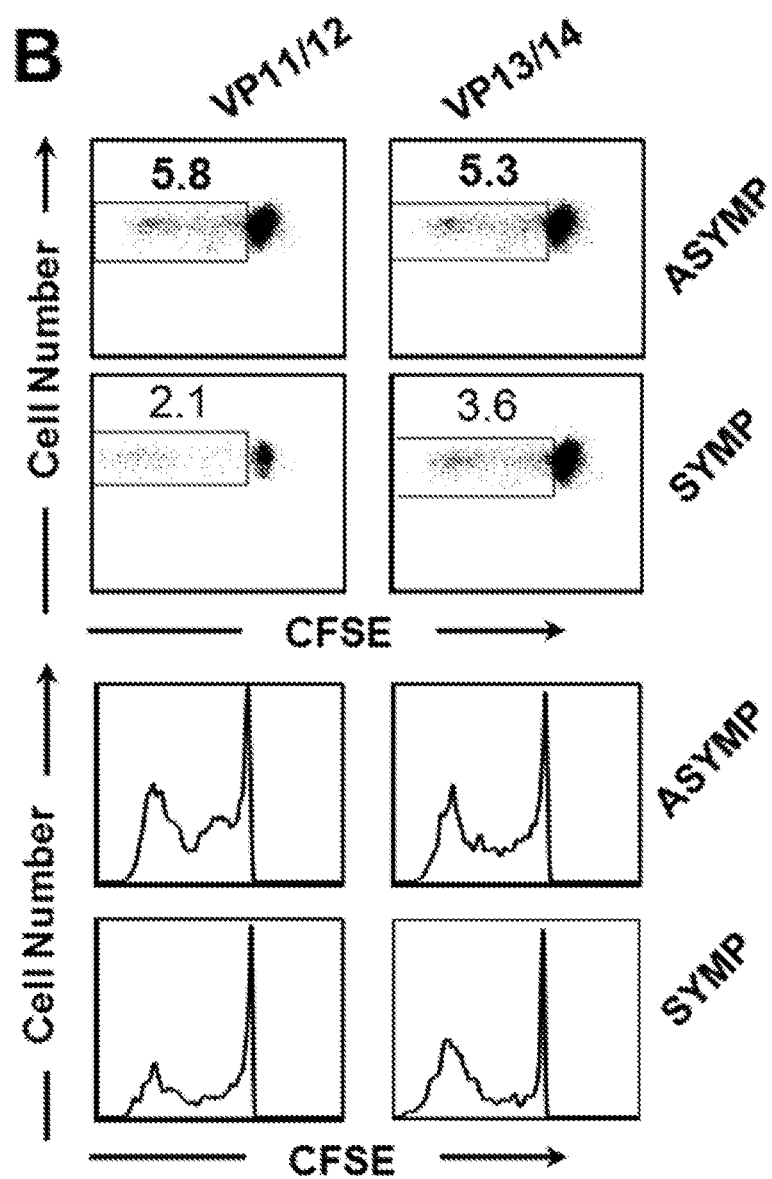
Figure 1C:
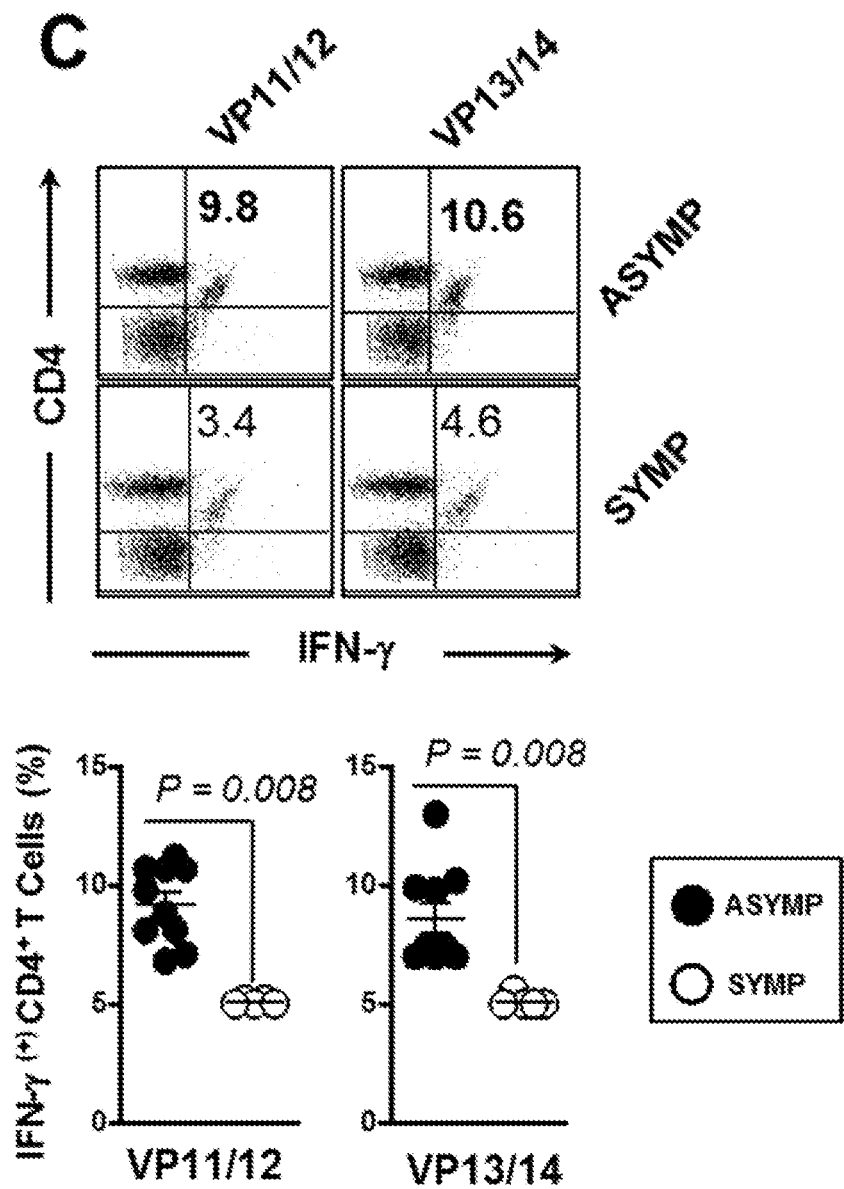
Figure 1D:
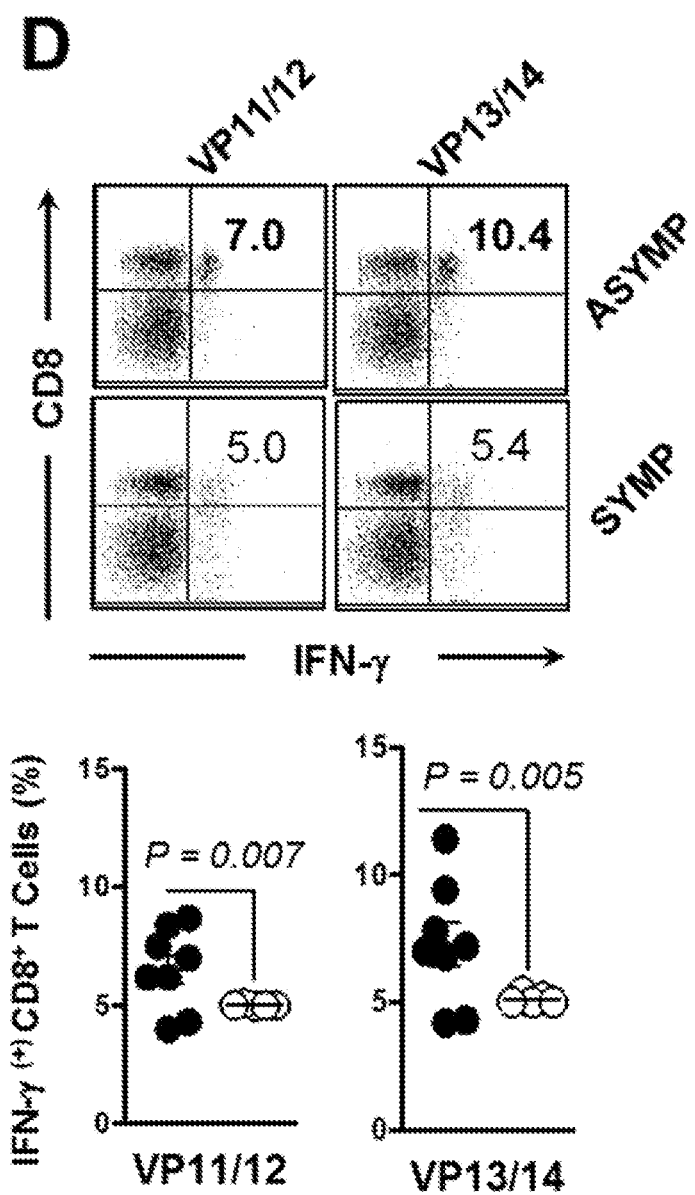

As shown in FIG. 1A, eight HSV-2 "asymptomatic" protein antigen Ag (gD, RR1, RR2, VP22, gB, VP16, VP13/14, VP11/12) were frequently recognized by CD4+ and CD8+ T cells from 10 out of 10 ASYMP patients, but not by CD4+ and CD8+ T cells from 10 SYMP patients ($P<0.001$; ANOVA post-test). The highest magnitude of recognition of CD4+ and CD8+ T cell responses from HSV-2 seropositive asymptomatic individuals were directed against gD, RR2, VP22, gB, and VP13/14, VP11/12 "asymptomatic" Ags (FIG. 1A). Elevated proliferative IFN-g-producing CD4+ and CD8+ T cells were detected in ASYMP compared to SYMP individuals. An example of VP13/14 and VP11/12 is shown in FIGS. 1B, 1C and 1D. Similar results were obtained with gD, RR2, VP22 and gB antigens. In contrast, CD4+ and CD8+ T cells from SYMP patients preferentially recognized UL25 antigen ($P<0.001$, FIG. 1A). Altogether, these results indicate that although CD4+ and CD8+ T cells from HSV-seropositive individuals recognize most of the 84 HSV protein Ags, a set of eight HSV-2 Ags recognized mostly by CD4+ and CD8+ T cells from ASYMP individuals while the UL25 Ag was recognized mostly by CD4+ and CD8+ T cells from SYMP individuals. For the remainder of this study, therefore, the gD, RR2, VP22, gB, VP16, VP13/14, VP11/12 are evaluated as "asymptomatic" protein Ags and the UL25 is evaluated as a "symptomatic" protein Ag for therapeutic vaccine pre-clinical testing in the guinea pig model of recurrent genital herpes.

Figure 2A:
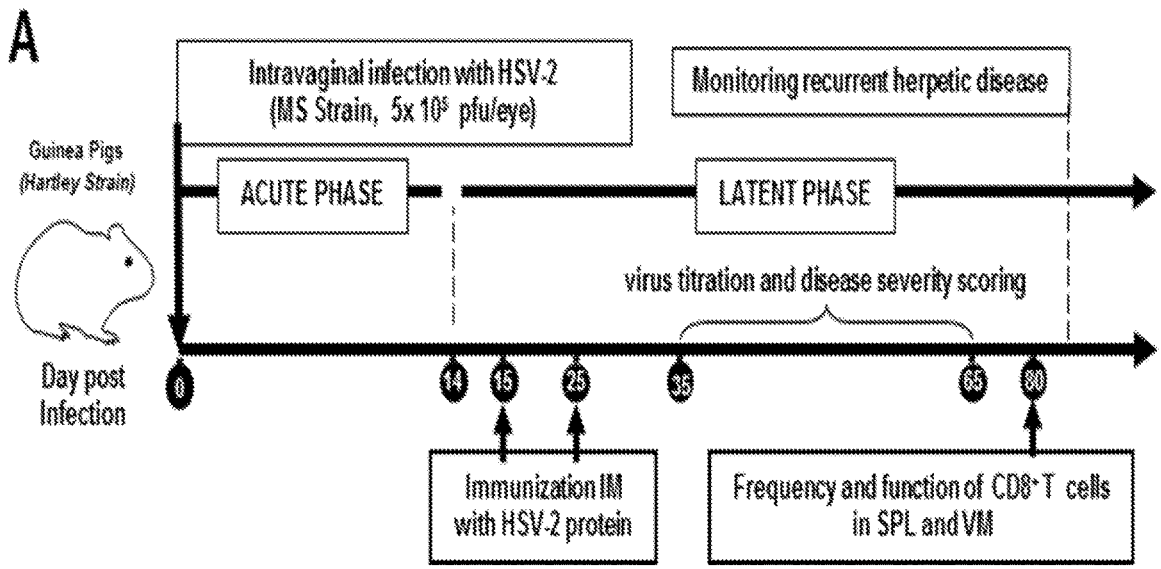
FIG. 2A through FIG. 2E, depicts the results of example experiments demonstrating protection against recurrent genital herpes infection and disease in HSV-2 infected guinea pigs following therapeutic immunization with eight protein-based subunit vaccine candidates.

Therapeutic Immunization of HSV-2 Infected Guinea Pigs with Three Out of Eight "Asymptomatic" HSV-2 Protein-Based Subunit Vaccines Produced Protection Against Recurrent Genital Herpes Infection and Disease Eight HSV-2 symptomatic and asymptomatic proteins selected above (gD, RR2, VP22, gB, VP16, VP13/14, VP11/12 and UL25) were recombinantly expressed. As shown in FIG. 2A, guinea pigs (n=90) were infected intravaginally on day 0 with 5×10$^5$ pfu of HSV-2 (strain MS). Once acute infection was resolved, the remaining latently infected animals were randomly divided into 8 groups (n=11) and then vaccinated twice intramuscularly on day 15 and on day 25 post-infection, with 10 μg of the indicated HSV-2 protein-based subunit vaccine emulsified in Alum+CpG adjuvants.

The replication defective HSV-2 d15-29 mutant vaccine was used as a positive control (d15-29). Mock-vaccinated guinea pigs, which received Alum +CpG adjuvants alone, were used as negative controls (Mock).

Figure 2B:
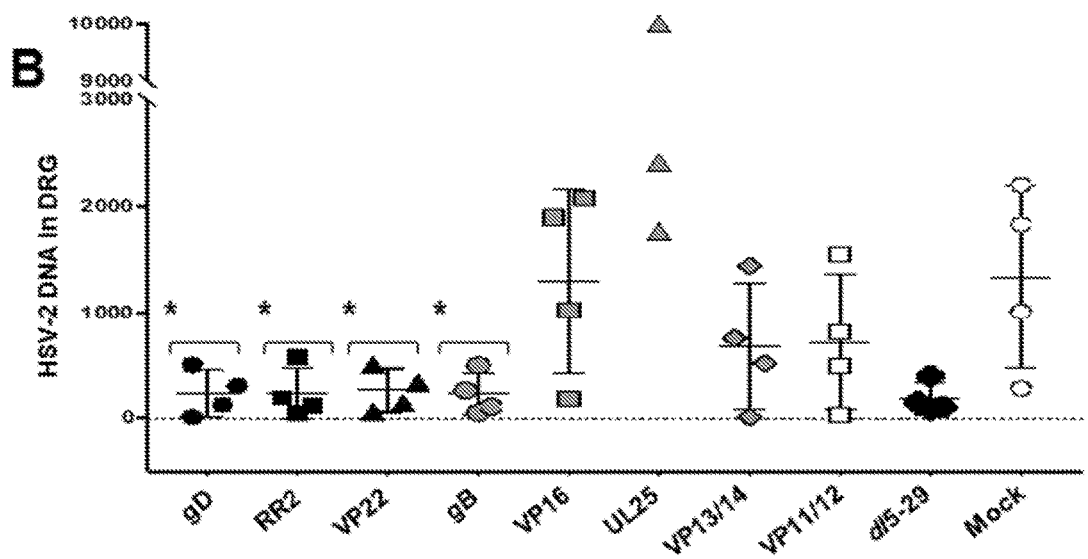
Figure 2C:
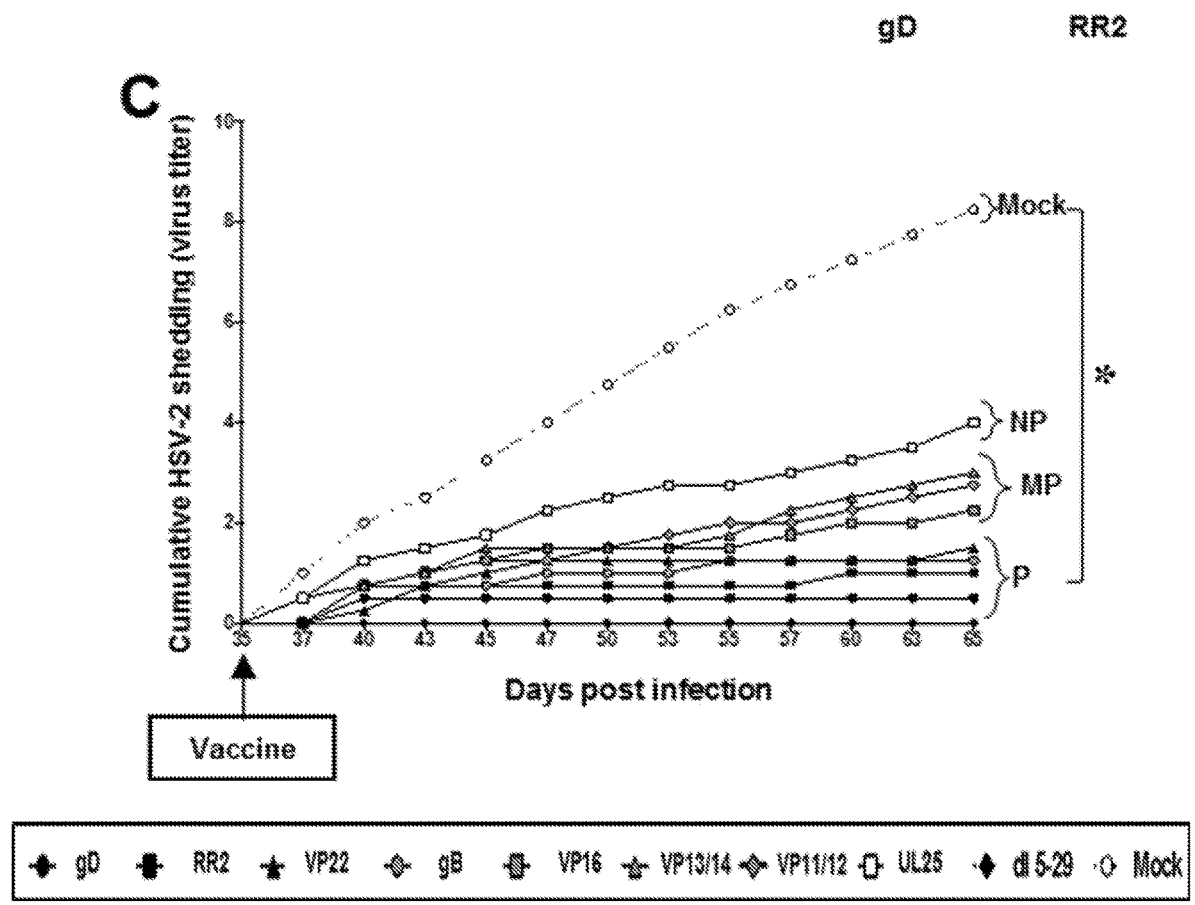
Figure 2D:
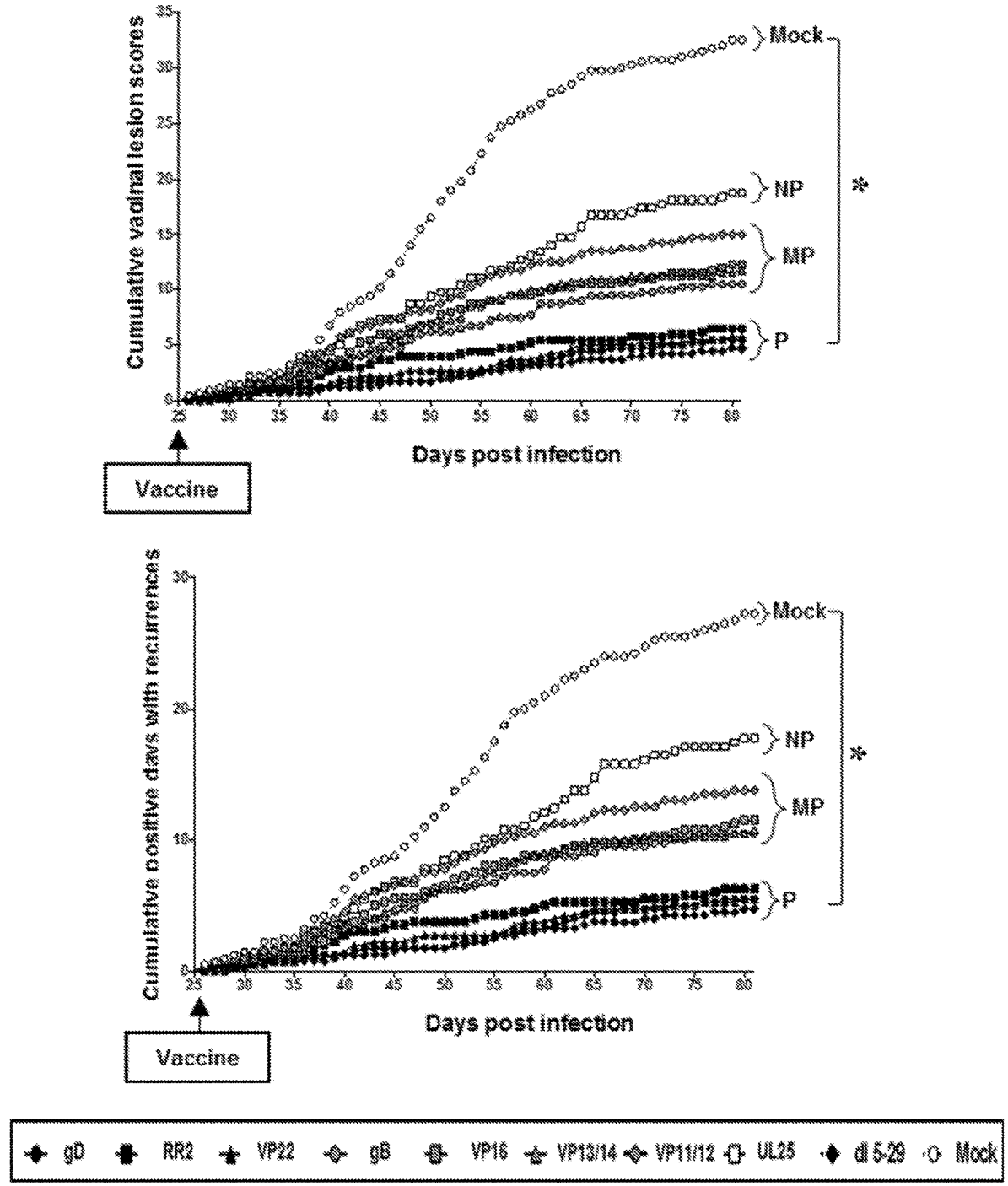
Figure 2E:
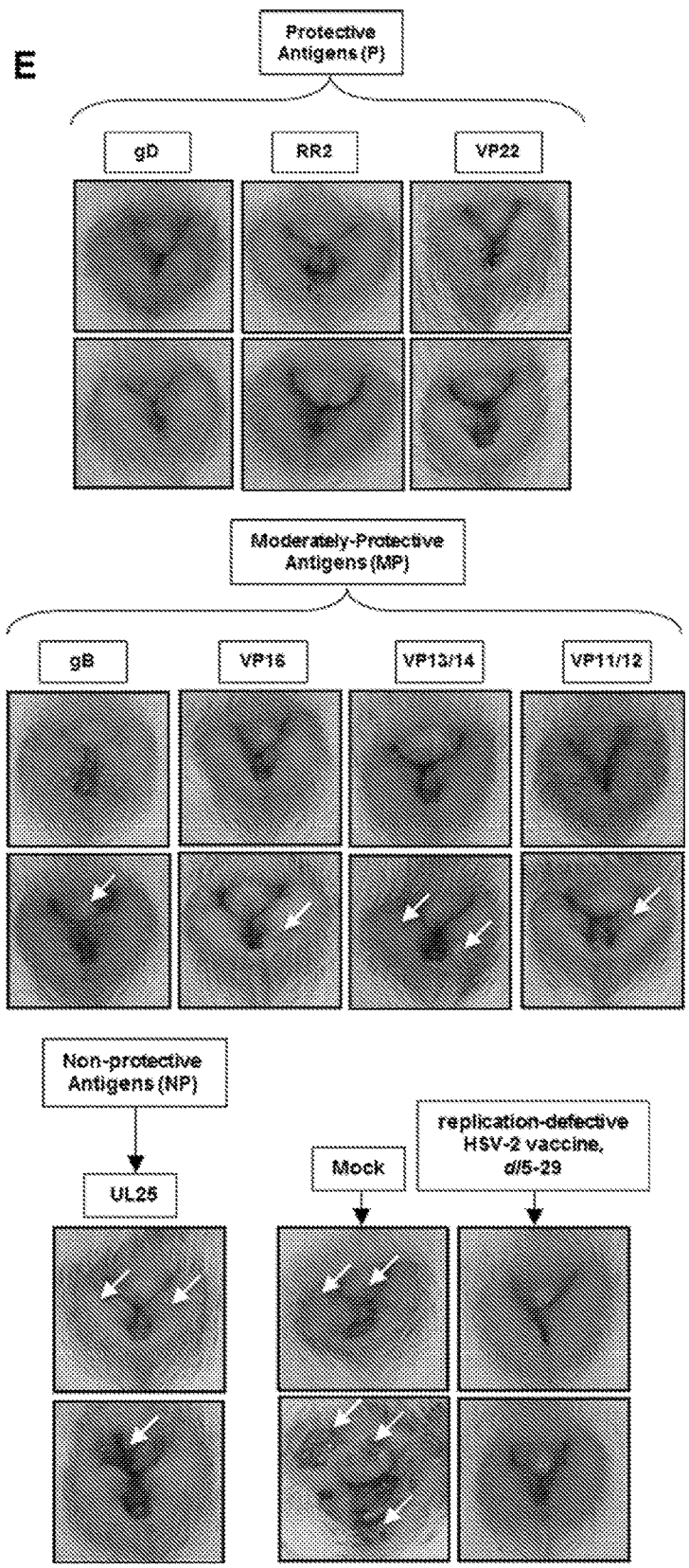

On day 80 post-infection (i.e., 55-days post second and final immunization), those guinea pigs that were vaccinated with gD, RR2 and VP22 proteins had the lowest HSV-2 DNA copy numbers detected in the DRG compared to guinea pigs that were vaccinated with gB, VP16, VP13/14, VP11/12 and UL25 proteins and to mock-vaccinated controls (FIG. 2B). As expected, the d15-29 positive vaccinated control had the lowest DNA copy numbers detected in the DRG. The reduction in HSV-2 DNA copy numbers detected in the DRG of gD, RR2 and VP22-vaccinated guinea pigs was accompanied with a significant reduction in cumulative virus vaginal shedding compared to the gB, VP16, VP13/14, VP11/12 and UL25-vaccinated animals and to mock-vaccinated controls ($P<0.05$, FIG. 2C). Moreover, as shown in FIG. 2D, the gD, RR2 and VP22-vaccinated guinea pigs exhibited significantly lower cumulative vaginal lesion and a reduced number of days with recurrent genital lesions. The severity of genital herpetic lesions, scored on a scale of 0 to 4, also confirmed the cure of recurrent disease in gD, RR2 and VP22-vaccinated guinea pigs (FIG. 2E). This protection was statistically significant and similar to the protection provided by vaccination with live attenuated d15-29 positive control. However, gB, VP16, VP13/14, and VP11/12 showed modest, but statistically significant protection against recurrent genital herpes. From the representative images, the lowest genital lesions were evidenced in guinea pigs vaccinated with gD, RR2 and VP22proteins; while gB, VP16, VP13/14, and VP11/12 were observed to be moderately-protective antigens against genital lesion. In contrast, vaccination with UL25 protein produced no protection against recurrent genital herpes infection and disease, similar to mock-vaccinated control ($P>0.05$, FIGS. 2B to 2E). UL25 was also found to be inefficient in preventing the establishment of latency.

Altogether these results therefore indicate that therapeutic immunization with gD, RR2 and VP22 antigens, selected for being highly recognized by the immune system from HSV-2 seropositive, but naturally "protected" ASYMP females (above), also protected HSV-2 seropositive guinea pigs against recurrent genital herpes infection and disease.

Figure 3A:
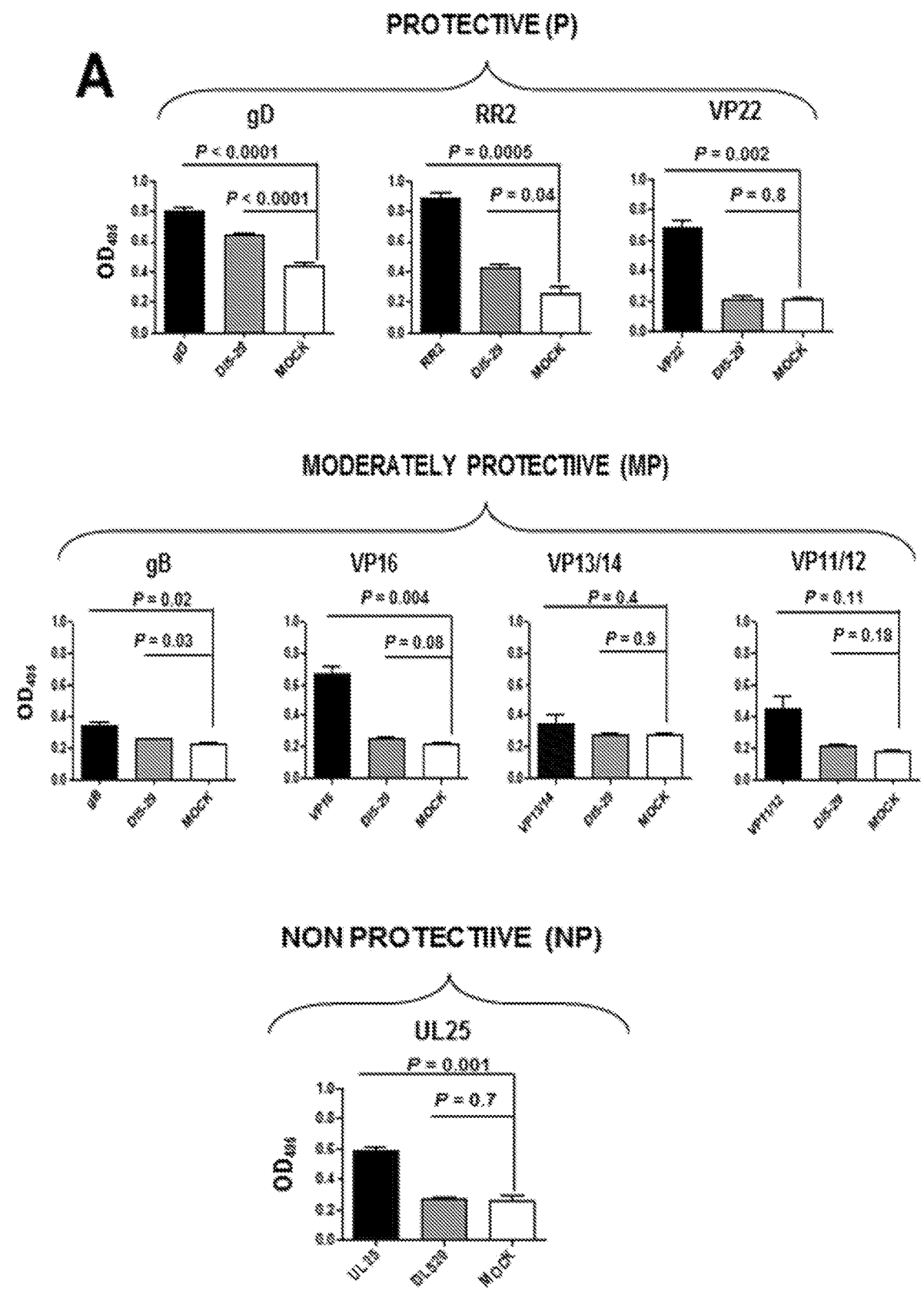
FIG. 3A through FIG. 3D, depicts the results of example experiments demonstrating the production of neutralizing antibodies in HSV-2 infected guinea pigs following therapeutic vaccination with gD, RR2, VP22, gB, VP16, VP13/14, VP11/12 and UL25 proteins.
Figure 3B:
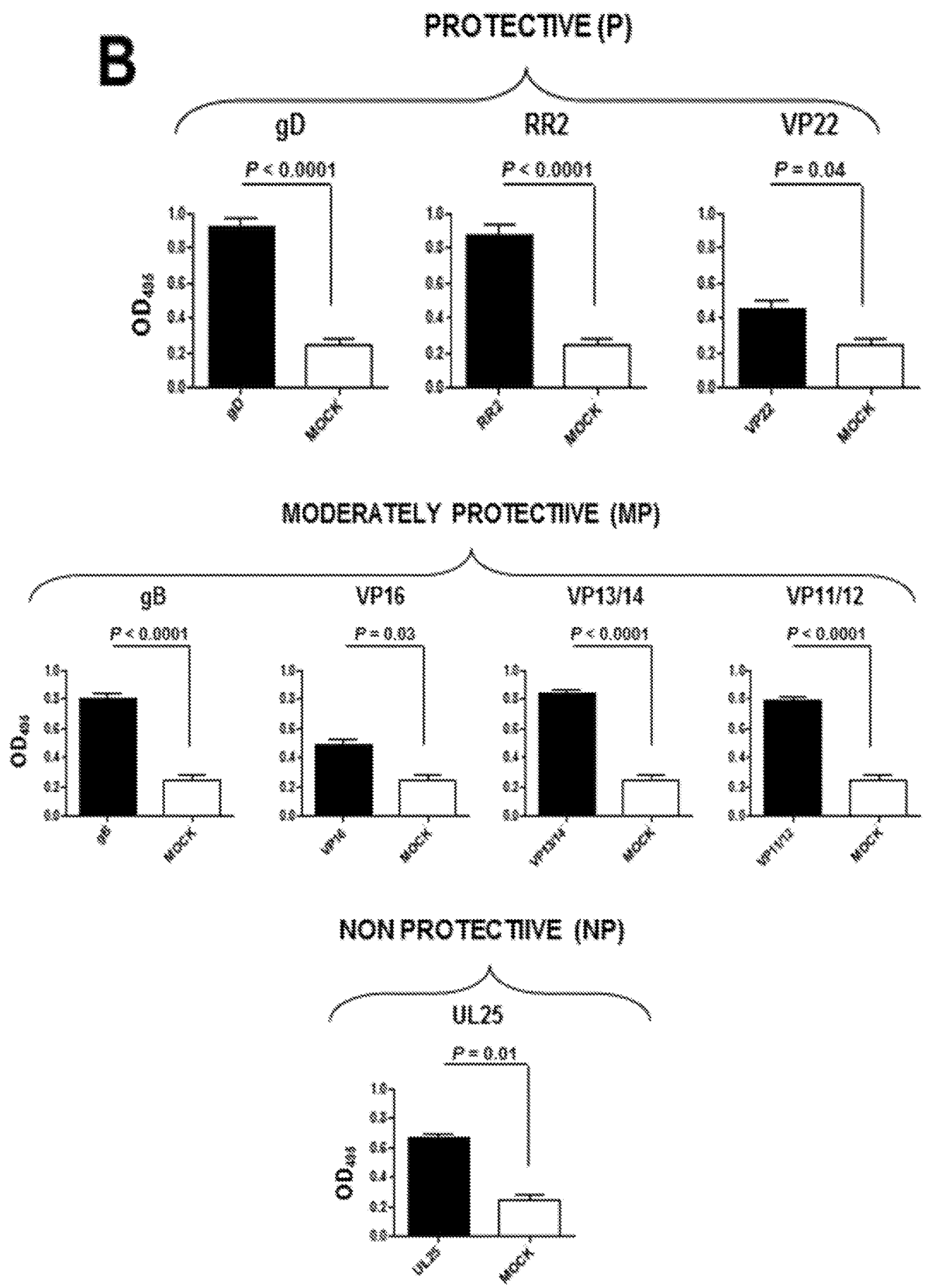
Figure 3C:
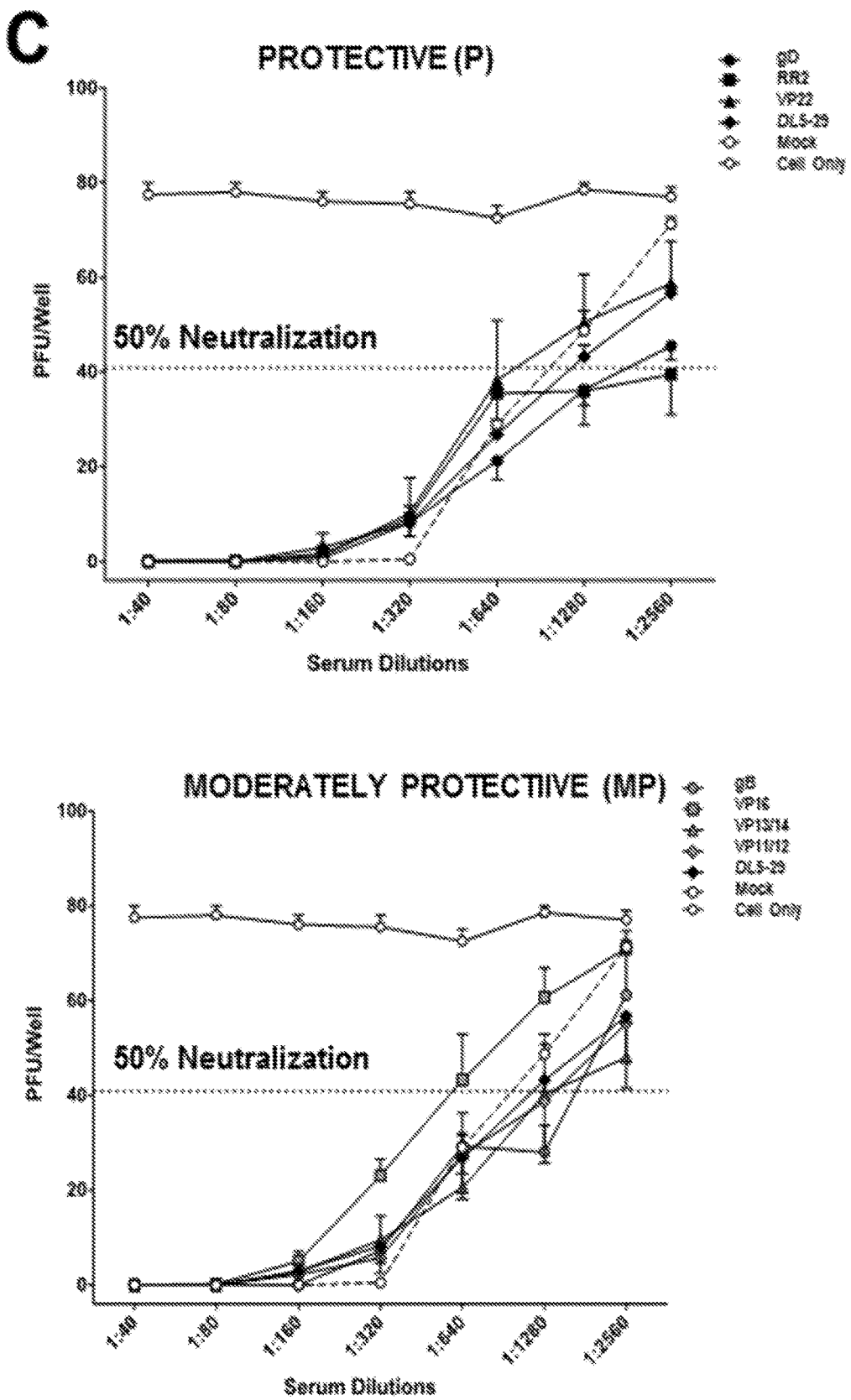
Figure 3C:
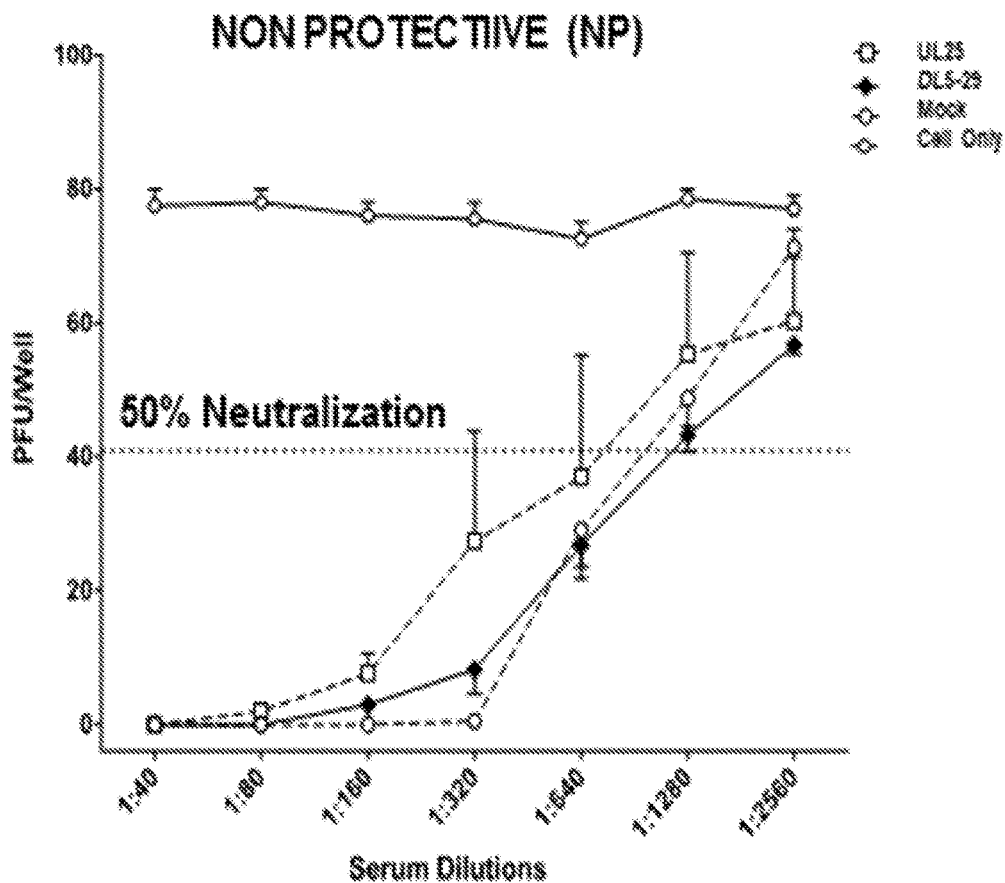

Therapeutic Vaccination of HSV-2 Infected Guinea Pigs with the RR2 Protein-Based Subunit Vaccine Produced High Neutralizing Antibody Titers that Cross-React with the Glycoproteins gB and gD Guinea pigs were infected intravaginally with $5\times10^5$ pfu of HSV-2 (strain MS). Groups of HSV-2 infected animals (n=11) were vaccinated twice, on day 15 and on day 25 post-infection with the indicated HSV-2 protein (FIG. 2). Fifty-five days after the second and final immunization, immune sera were collected and tested for Ag- and HSV-specific IgG by ELISA and neutralization assays. Significantly higher levels of Ag-specific IgG were detected by ELISA in sera from the guinea pigs that were vaccinated with gD, RR2, VP22, VP16, VP11/12 and UL25 proteins as compared to the mock-vaccinated group (Mock) (FIG. 3A). Sera from DL5-29 vaccinated animals evaluated at 1:1000 dilution also recognized gD and RR2 as coating Ags. Immune sera from guinea pigs that were vaccinated with gD, RR2, gB, VP13/14, VP11/12 and UL25, but not sera from the mock-vaccinated group (Mock), had IgG that bound with high affinity to native viral epitopes, as detected by ELISA using plates coated with whole heat-inactivated HSV-2 (FIG. 3B). Neutralizing antibody titers (without complement) were evaluated in immune sera obtained at terminal bleed of guinea pigs that were vaccinated with gD, RR2, VP22, gB, VP16, VP13/14, VP11/12 and UL25. Immune sera from gD and RR2 proteins had the highest neutralizing antibody titers (FIG. 3C, left panel). The 50% neutralization titer in serum of mock-immunized animals was around 1:640, while immune serum of gD and RR2-immunized animals had a neutralization titer >1:1280 and >1:2560, respectively (FIG. 3C, left panel). As expected, sera from animals that were vaccinated with DL5-29 that delivered all the envelope glycoproteins produced high neutralizing antibody titers.

Figure 3D:
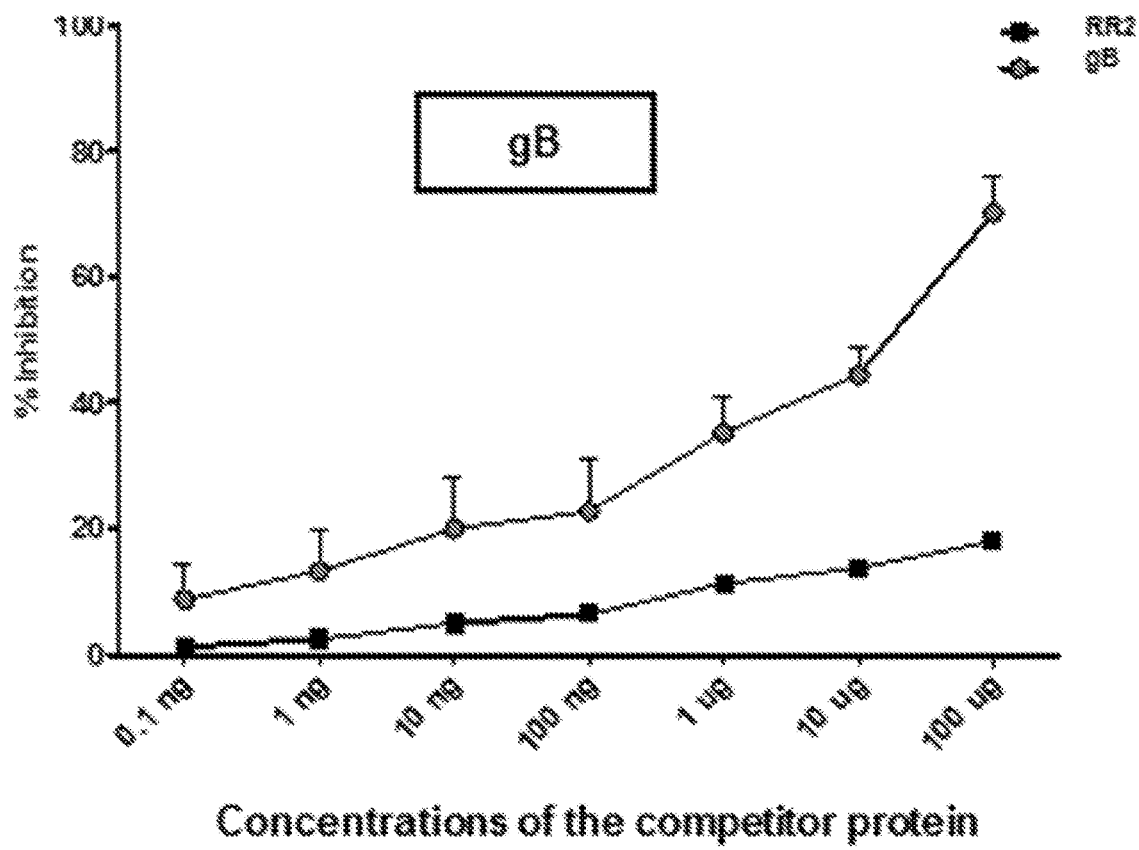

Since immune sera from RR2, a non-surface envelope protein, produced the highest neutralizing antibody titers, it was next examined whether the RR2-induced antibodies cross-reacted with envelope proteins, such as gB and gD. As shown in FIG. 3D, competitive-ELISA experiments were used, in which plates were first coated with 1 μg of RR2 protein (left panel), 1 μg of gD protein (Middle panel), or 1 μg of gB protein (right panel). ELISA plates were then incubated with immune sera from RR2, gD or gB immunized guinea pigs, that were pre-incubated with different concentrations of the competitor protein (i.e. RR2, gB or gD). The percentage of inhibition at each tested concentration of the competitor protein was calculated with respect to the optical density (OD495nm) value of the respective immune serum alone, incubated in the absence of the competitor protein. When RR2 protein was used as coated Ag, there was a significant inhibition of IgG binding not only of immune sera pre-incubated with RR2 protein (control), but also of immune serum pre-incubated with gD protein (FIG. 3D, left panel). Inversely, when gD protein was used as coated Ag, there was a significant inhibition of IgG binding not only of immune sera pre-incubated with gD protein (control), but also of immune sera pre-incubated with RR2 protein, suggesting cross-reactivity B-cell epitopes between RR2 and gD (FIG. 3D, middle panel). Moreover, when gB protein was used as coated Ag, there was also a significant inhibition of IgG binding of immune serum pre-incubated with RR2 protein, also suggesting cross-reactive epitopes between RR2 and gB (FIG. 3D, right panel). These results indicate that therapeutic vaccination of HSV-2 infected guinea pigs with the RR2 protein-based subunit vaccine produced high neutralizing antibody titers that appear to cross-react with both gB and gD.

Therapeutic Vaccination of HSV-2 Infected Guinea Pigs with RR2 Protein Induced Frequent Vaginal Mucocutaneous Tissue-Resident $CD4^+$ and $CD8^+$ T Cells that Localized to Healed Sites of the Vaginal Mucocutaneous Tissues Guinea pigs were infected (n=60) intravaginally with $5\times10^5$ pfu of HSV-2 (strain MS). Once acute infection was resolved, latently infected animals were randomly divided into 8 groups (n=4) and then vaccinated intramuscularly twice, on day 15 and on day 25 post-infection, with individual gD, RR2, VP22, gB, VP16, VP13/14, VP11/12 or UL25 antigens emulsified in Alum+CpG adjuvants. The replication defective dl5-29 vaccine was used as a positive control (dl5-29). Mock-vaccinated guinea pigs, which received adjuvant alone, were used as negative control (Mock). On day 55 after the second and final immunization, guinea pigs were euthanized and the frequency of vaginal mucosal (VM) tissue-resident $CD4^+$ and $CD8^+$ T cells were detected by FACS.

Figure 4A:
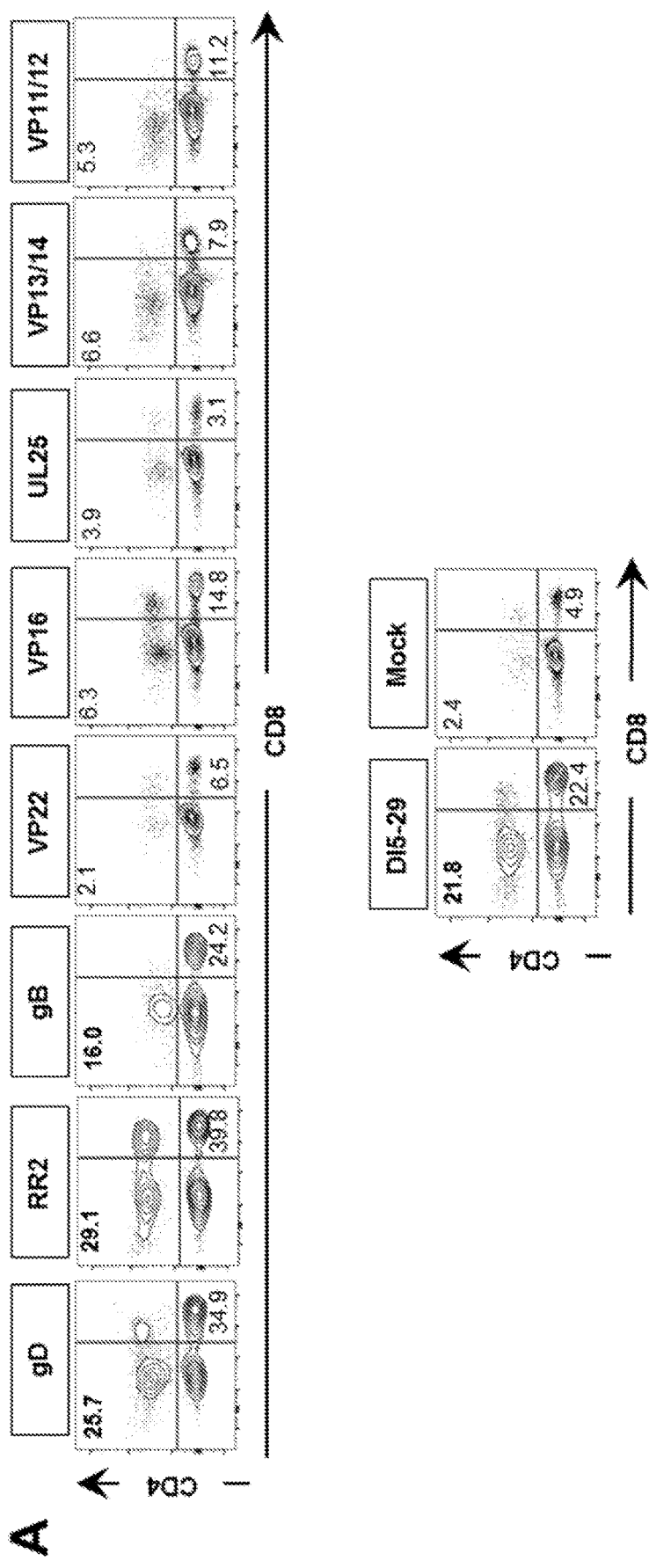
FIG. 4A through FIG. 4C, depicts the results of example experiments demonstrating the frequency of CD4+ and CD8+ T cells in the vaginal-mucosa of HSV-2 infected in guinea pigs following therapeutic vaccination with gD, RR2, VP22, gB, VP16, VP13/14, VP11/12 and UL25 proteins.
Figure 4B:
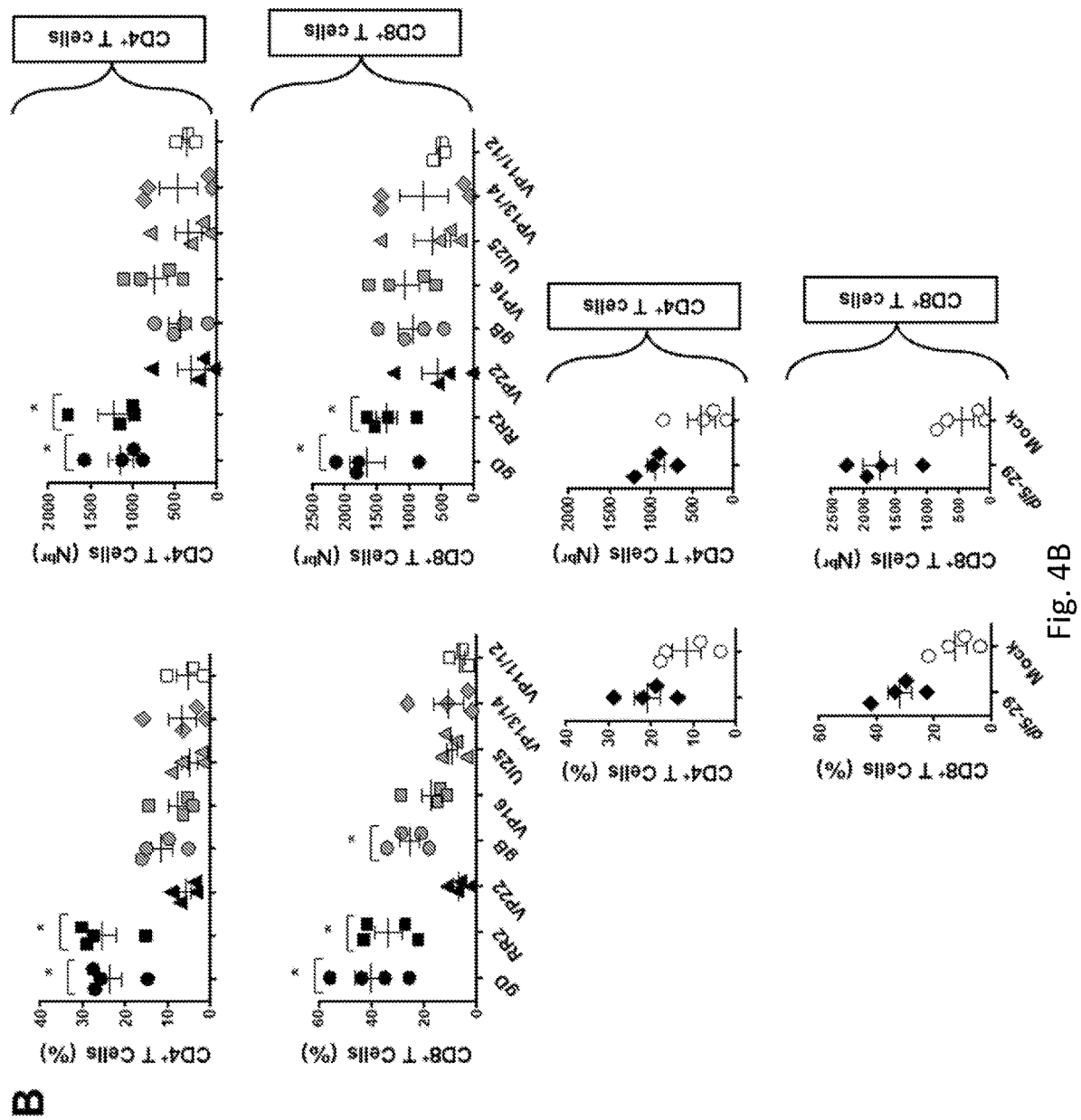
Figure 4C:
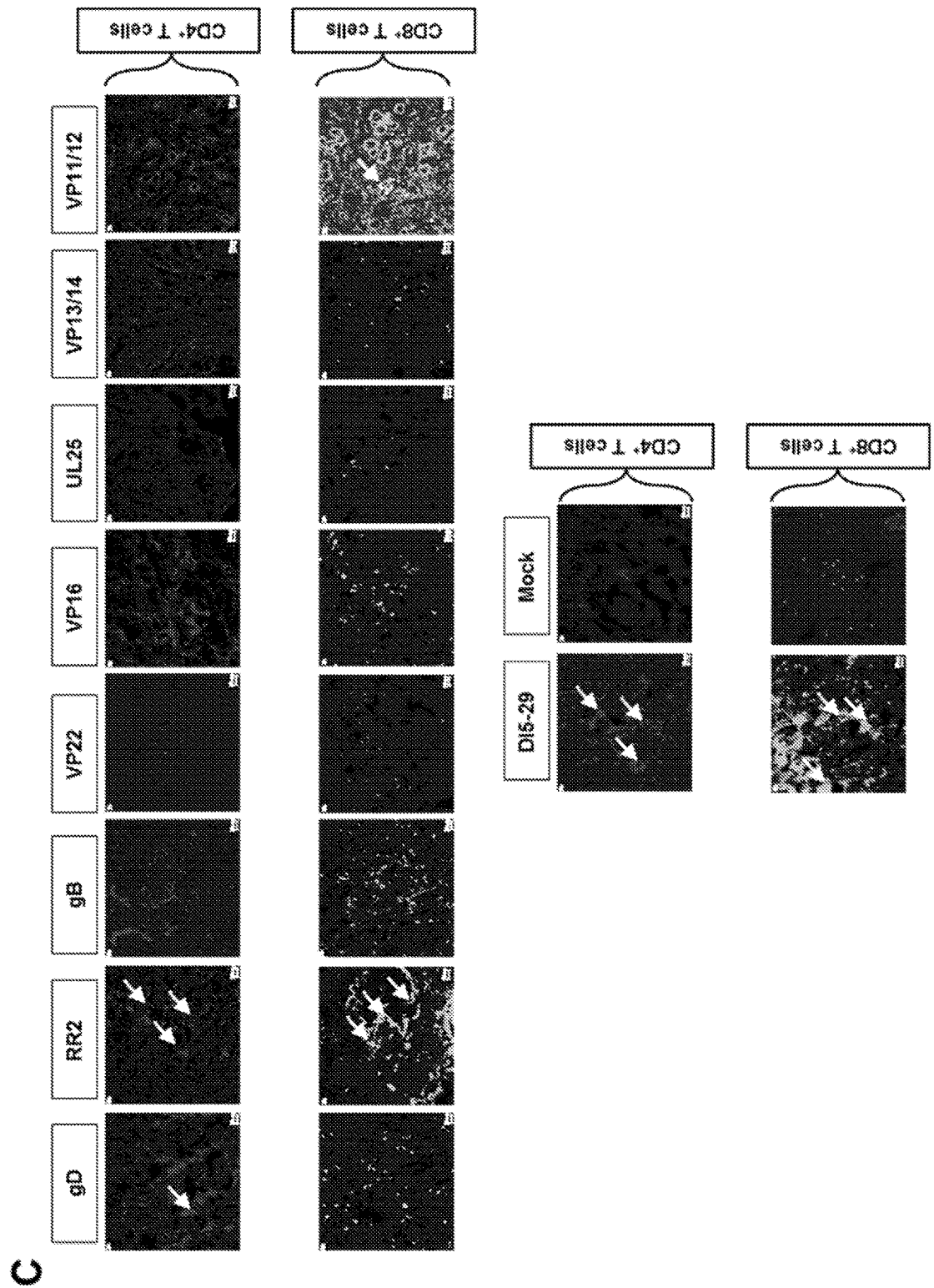

Overall high frequencies of $CD4^+$ and $CD8^+$ T cells were induced by gD, RR2, VP22, gB, VP16, VP13/14, VP11/12 and UL25-based vaccines compared to mock-vaccine (i.e. adjuvant alone) (FIGS. 4A and 4B). The highest frequencies of both $CD4^+$ and $CD8^+$ T cells were detected in the VM of guinea pigs that were vaccinated with gD and RR2 protein-based vaccines (FIGS. 4A and 4B, left two panels). These frequencies were even slightly higher than those detected by FACS in the VM of guinea pigs that were immunized with the whole replication defective of dl5-29 virus (FIGS. 4A and 4B, right two panels). Using fluorescence microscopy, more $CD4^+$ and $CD8^+$ T cell infiltrates were visualized that localized to healed sites of the vaginal mucocutaneous tissues of protected guinea pigs that were immunized with gD and RR2 Ags, but not to the vaginal mucocutaneous tissues of non-protected guinea pigs that were immunized with the remaining HSV-2 antigens (FIG. 4C, left two panels).

Figures 5A, 5B:
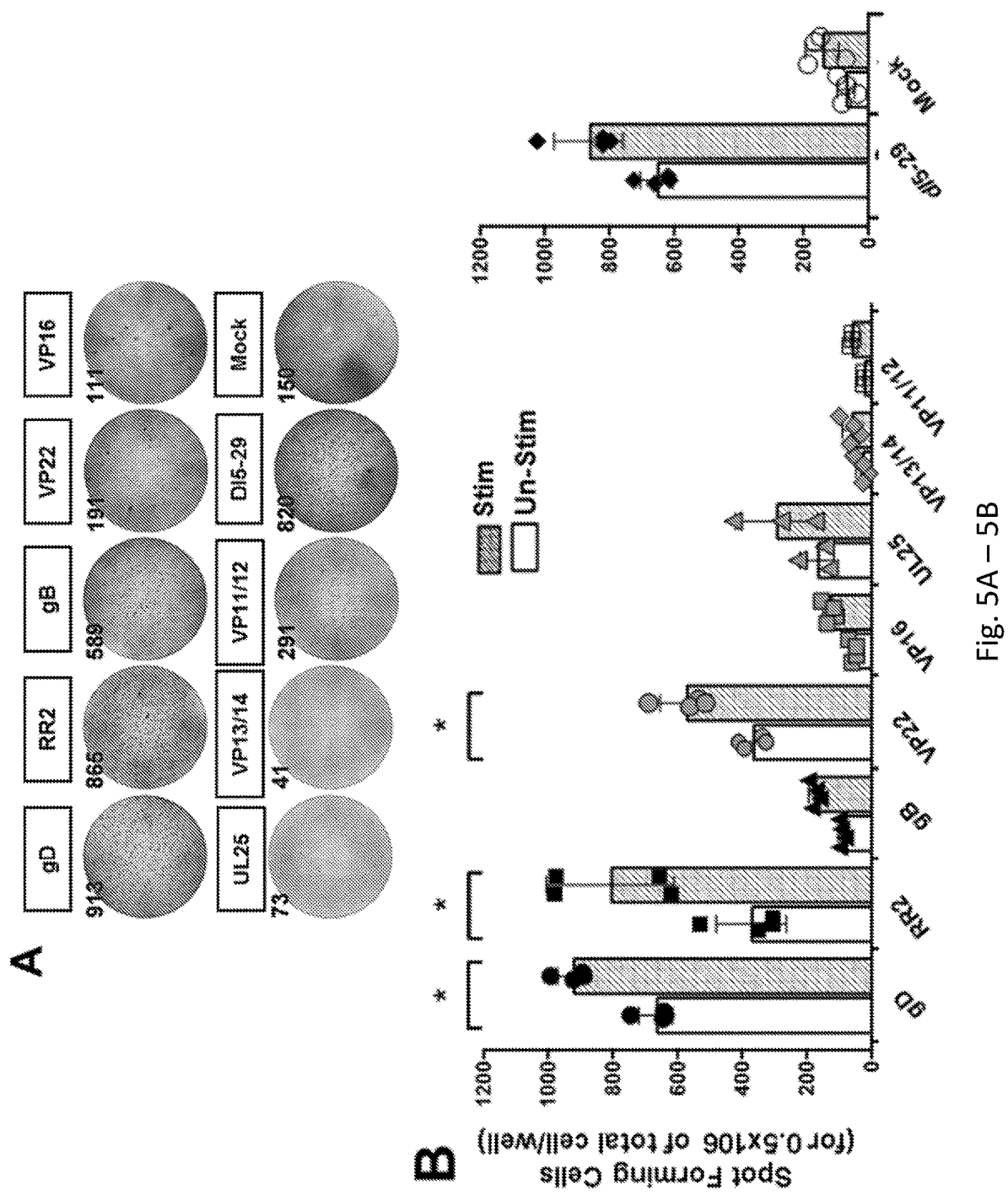
FIG. 5A through FIG. 5D, depicts the results of example experiments demonstrating the function of vaginal-mucosa-resident CD4+ and CD8+ T cells from HSV-2 infected guinea pigs following therapeutic vaccination with gD, RR2, VP22, gB, VP16, VP13/14, VP11/12 and UL25 proteins.
Figure 5C:
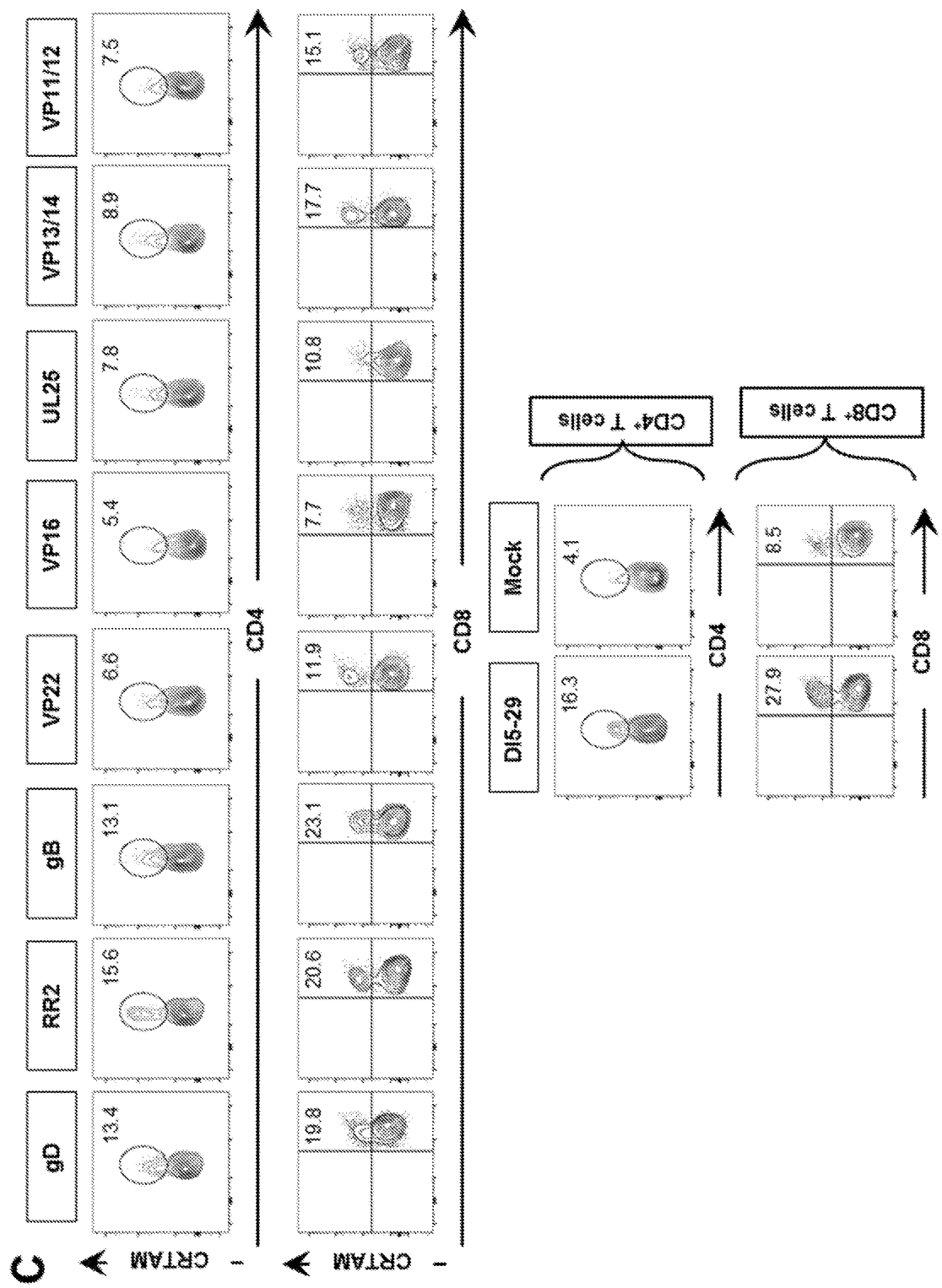
Figure 5D:
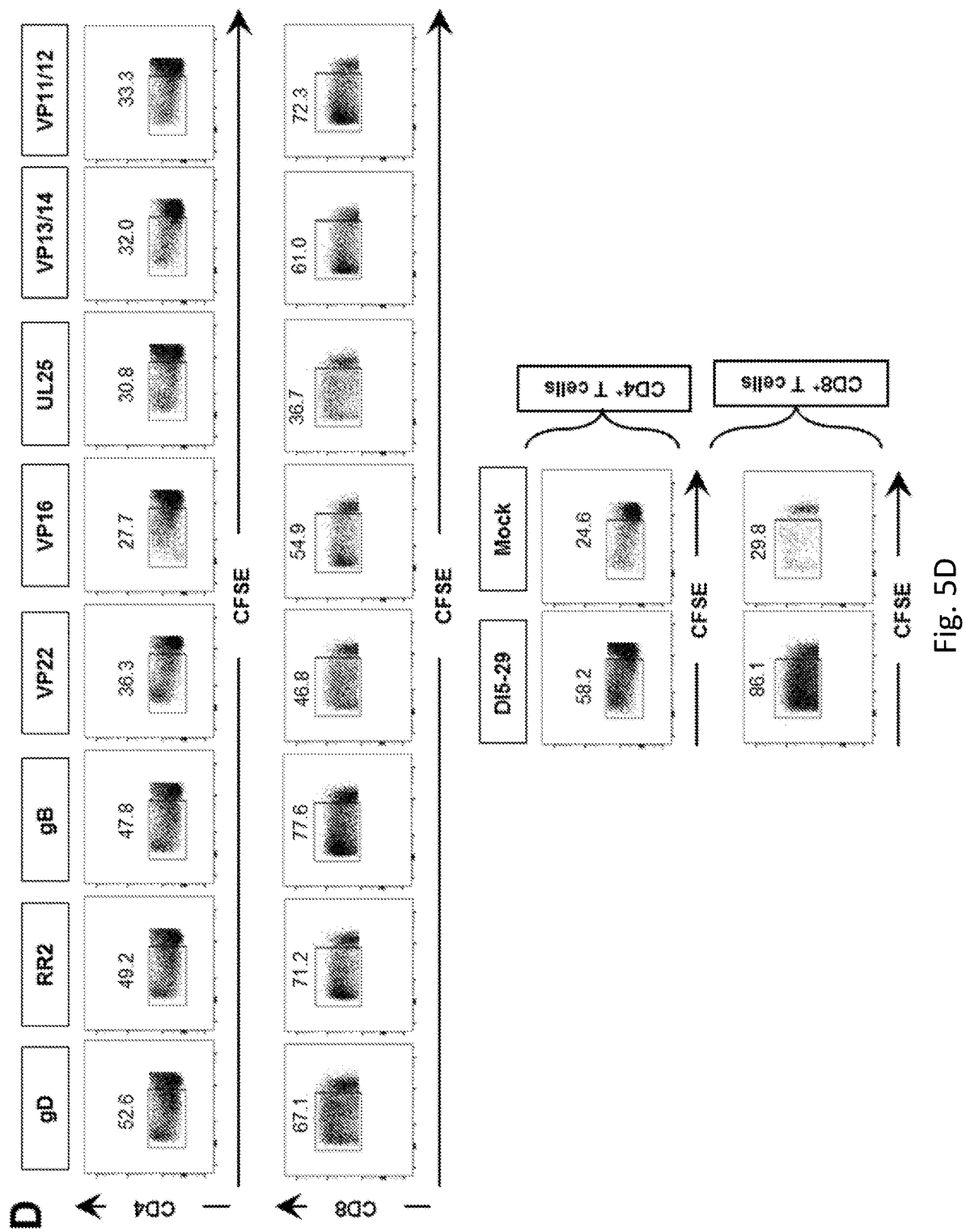

Protection Induced Following Therapeutic Vaccination with RR2, gD and gB Proteins is Associated with More Functional Vaginal-Mucosa-Resident $IFN-g^+CRTAM^+CD4^+$ and $IFN-g^+CRTAM^+CD8^+$ T cells The function and exhaustion of $CD4^+$ and $CD8^+$ T cells was compared in the vaginal mucosal (VM) of HSV-2 infected guinea pigs following therapeutic vaccination with gD, RR2, VP22, gB, VP16, VP13/14, VP11/12 and UL25 proteins. On day 55 after the second and final therapeutic immunization guinea pigs were euthanized, single cell suspension from the VM tissue were obtained and the function/dysfunction of VM-resident $CD4^+$ and $CD8^+$ T cells were analyzed using both IFN-g ELISPOT and FACS. Significantly high numbers of IFN-g-producing $CD4^+$ and $CD8^+$ T cells, enumerated by ex vivo ELISPOT assay in the VM of HSV-2 infected guinea pigs following vaccination with gD, RR2, and gB proteins were observed compared to vaccination with VP22, VP16, VP13/14, VP11/12 and UL25 proteins ($P<0.05$, FIGS. 5A and 5B). The number of IFN-g-producing $CD4^+$ and $CD8^+$ T cells detected in the VM of gD and RR2 vaccinated groups equaled the number of IFN-g-producing $CD4^+$ and $CD8^+$ T cells detected in the VM DL5-29 vaccinated group (positive control). Following a 48h stimulation with 10 μg of immunizing HSV-2 proteins (Stim) there was a boost in the number of IFN-g-producing $CD4^+$ and $CD8^+$ T cells in the VM cells compared to ex vivo non-stimulated VM cells (Un-Stim) from gD, RR2, and VP22 groups but not from the remaining five groups, gB, VP16, VP13/14, VP11/12 and UL25 ($P<0.05$) (FIG. 5B). Similarly, as shown in FIG. 5C, significantly higher frequencies of functional $CRTAM^+$ $CD8^+$ T cells (top row) and of $CRTAM^+CD4^+$ T cells (bottom row) were detected in VM of HSV-2 infected guinea pigs following vaccination with gD, RR2, and gB proteins compared to VP22, VP16, VP13/14, VP11/12 and UL25 proteins ($P<0.05$). As shown in FIG. 5D, significantly high proliferative responses of $CFSE^+CD4^+$ T cells (top panels) and $CFSE^+CD8^+$ T cells (bottom panels) were detected in the VM of gD, RR2, and VP22 compared to VP16, gB, VP13/14, VP11/12 and UL25 group, confirming more functional VM-resident $CD4^+$ and $CD8^+$ T cells are associated with protection ($P<0.05$). As expected, high numbers of functional $CD4^+$ and $CD8^+$ T cells were detected in the VM of the DL5-29 vaccinated group (positive control) (FIGS. 5A to 5D). Altogether, these results indicate that therapeutic vaccination of HSV-2 infected guinea pigs with gD, RR2, and VP22 proteins induced more $IFN-g+CRTAM+CFSE^+CD4^+$ and $IFN-g+CRTAM^+CFSE^+CD8^+$ T cells within the vaginal mucocutaneous tissue associated with significant protection against recurrent genital herpes.

The Reduction in Virus Shedding and Severity and Frequency of Recurrent Genital Herpes Lesions in RR2-Vaccinated Guinea Pigs is Associated with Increased Numbers of Functional VM Tissue-Resident $CD4^+$ and $CD8^+$ T Cells To identify potential correlates of protective local T cell immunity following RR2 protein therapeutic vaccination of HSV-2 infected guinea pigs, it was next sought to determine the association of various parameters of protection (i.e. virus shedding and severity and frequency of recurrent genital herpes lesions) with the number, the function and exhaustion of $CD4^+$ and $CD8^+$ T cells that reside at the mucosal surface.

Figure 6A:
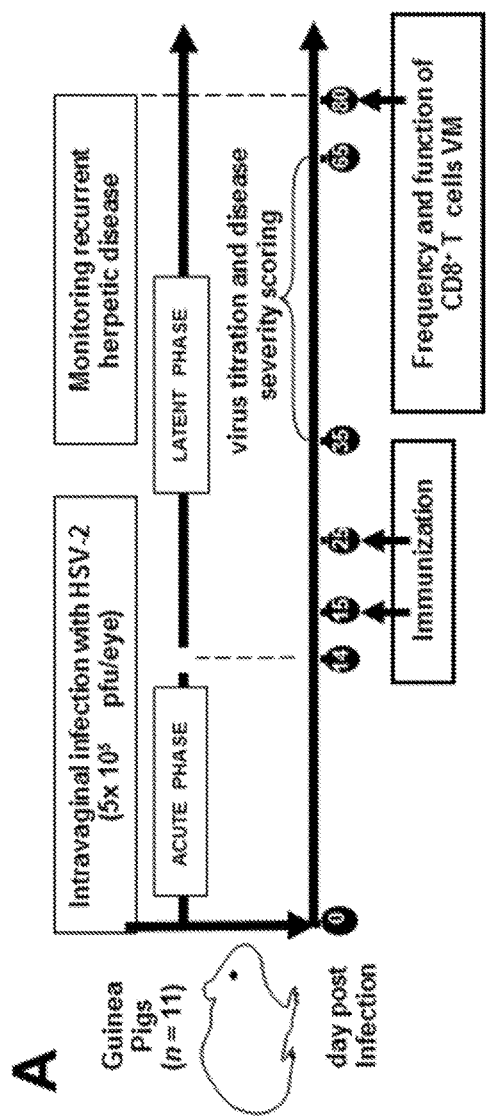
FIG. 6A through FIG. 6G, depicts the results of example experiments demonstrating correlates of protection with function and exhaustion of local vaginal mucosal-resident CD8+ T cells following RR2 protein therapeutic vaccination of HSV-2 infected guinea pigs.
Figure 6B:
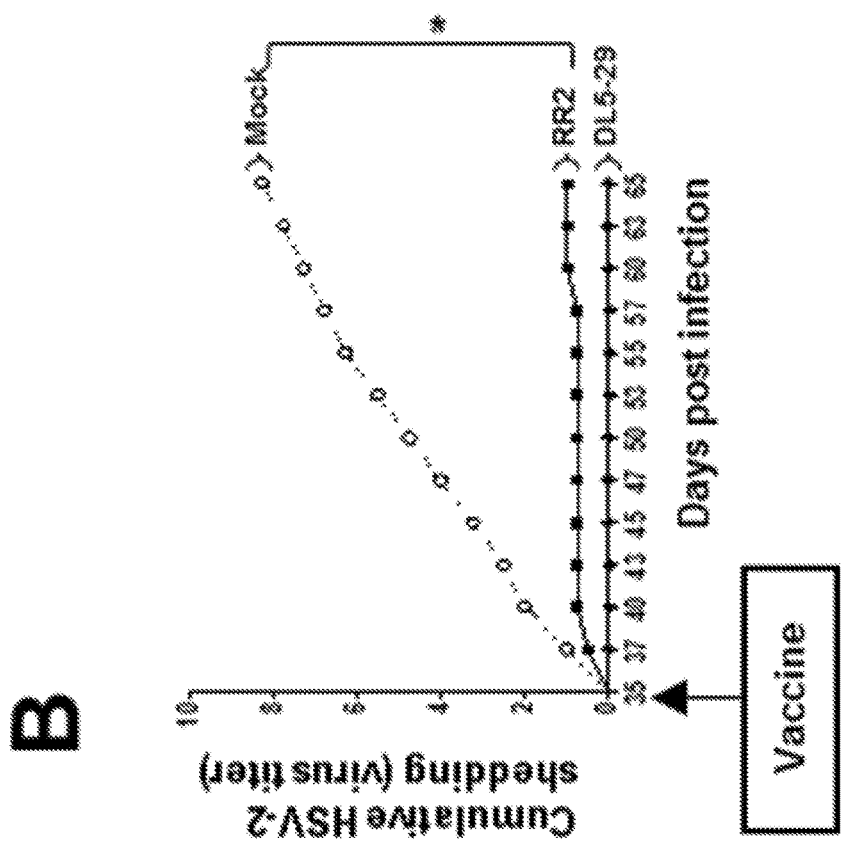
Figure 6C:
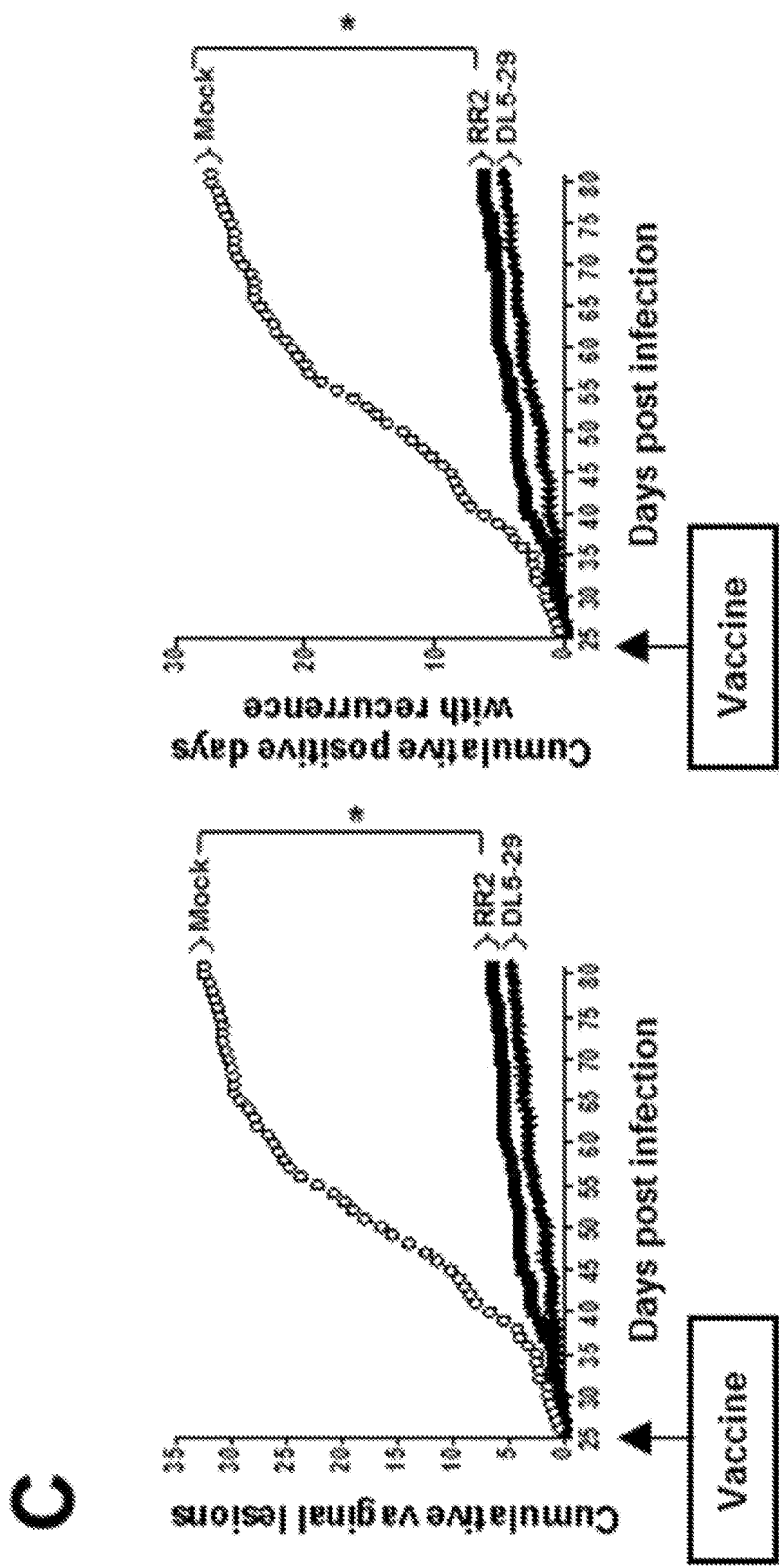
Figures 6D, 6E:
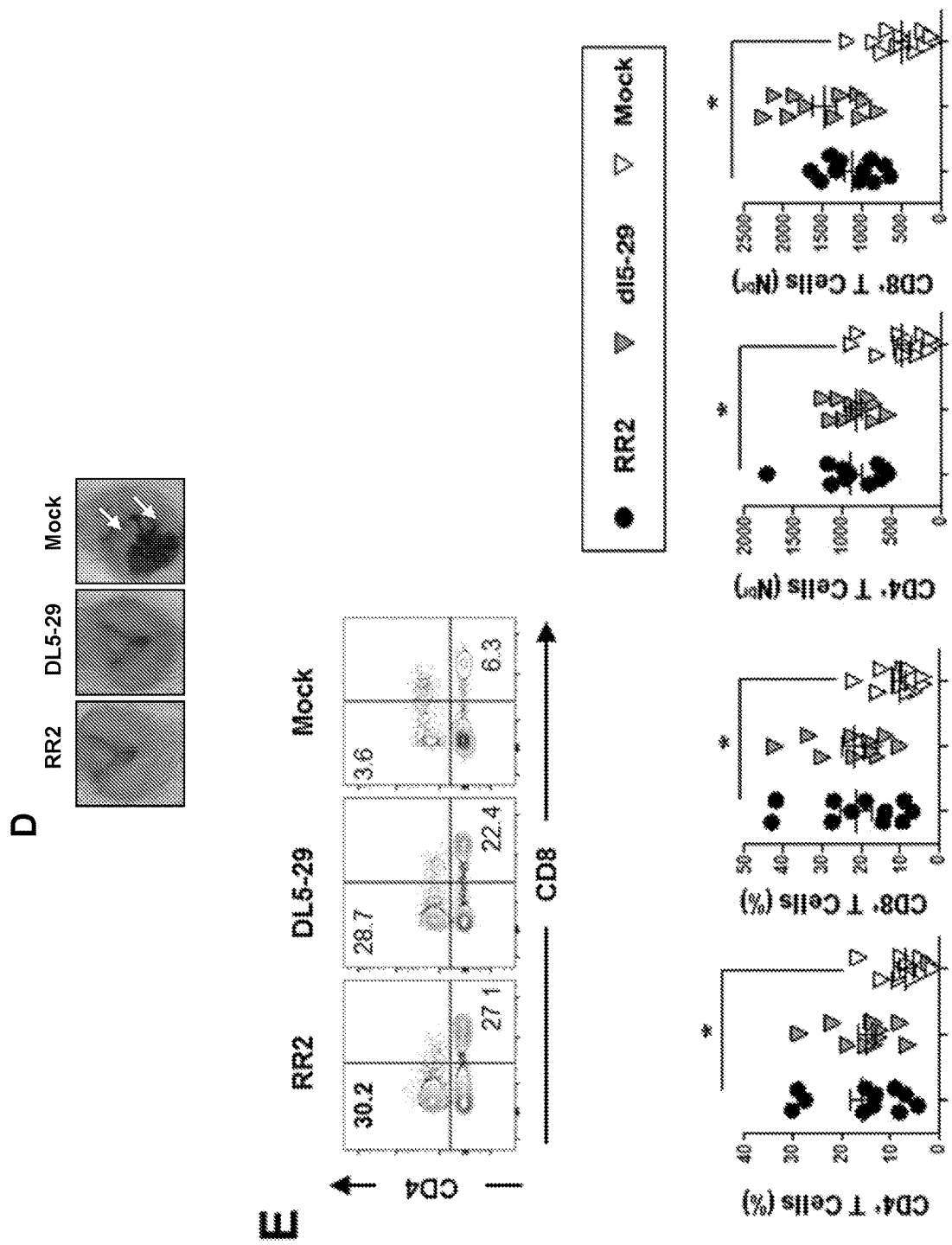

Guinea pigs (n=40) were infected intravaginally with $5 \times 10^5$ pfu of HSV-2 (strain MS). Once acute infection was resolved, latently infected animals were randomly divided into 3 groups (n=11) and then vaccinated intramuscularly twice, on day 15 and on day 25 post-infection, with either RR2 protein emulsified in Alum+CpG adjuvants (group 1) or with the replication defective dl5-29 vaccine (positive control, group 2) (FIG. 6A). Mock-vaccinated guinea pigs, which received adjuvant alone, were used as negative controls (Mock, group 3). A significant reduction in cumulative virus shedding was detected in the vaginal swabs in RR2-vaccinated animals compared to mock-vaccinated controls ($P<0.05$, FIG. 6B). This was accompanied with a significant reduction in cumulative virus vaginal shedding, a lower cumulative vaginal lesion (left panel), and a reduced number of days with recurrent genital lesions (left panel) ($P<0.05$ FIG. 6C). The level of protection induced with RR2 was similar to the level in dl5-29 positive control group (FIG. 6C). As expected, mock-vaccinated animals developed no protection against recurrent genital herpes infection and disease, and had little to no apparent inflammation/disease ($P>0.05$, FIG. 6C). Histologically, neither the dl5-29 nor the RR2 vaccinated animals had any apparent inflammation/disease or genital herpetic lesions, compared to various degrees of severe ulcerative vaginitis detected in all mock-vaccinated animals (FIG. 6D).

On day 55 after the second and final immunization, guinea pigs were euthanized and the frequency, function and exhaustion of the vaginal mucosal (VM) tissue-resident $CD4^+$ and $CD8^+$ T cells were determined. Significantly higher percentages of both $CD4^+$ and $CD8^+$ T cells were detected by FACS in the VM tissue of RR2 vaccinated compared to mock-vaccinated animals ($P<0.05$, FIG. 6E, left and right panels). These frequencies were even slightly higher than those detected in the VM of guinea pigs that were immunized with the whole replication defective of dl5-29 virus (FIG. 6E, left two panels).

Figure 6F:
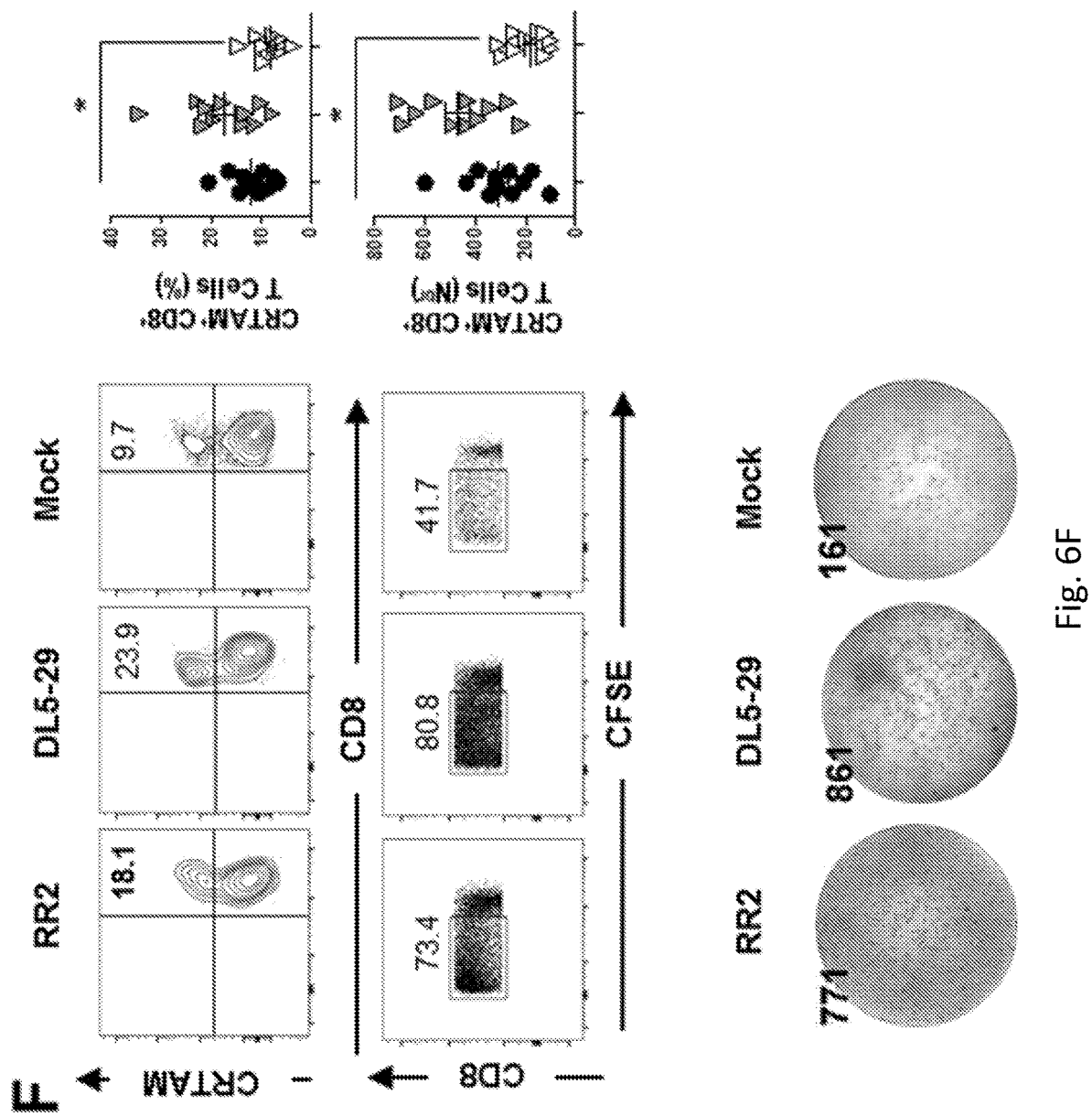
Figure 6G:
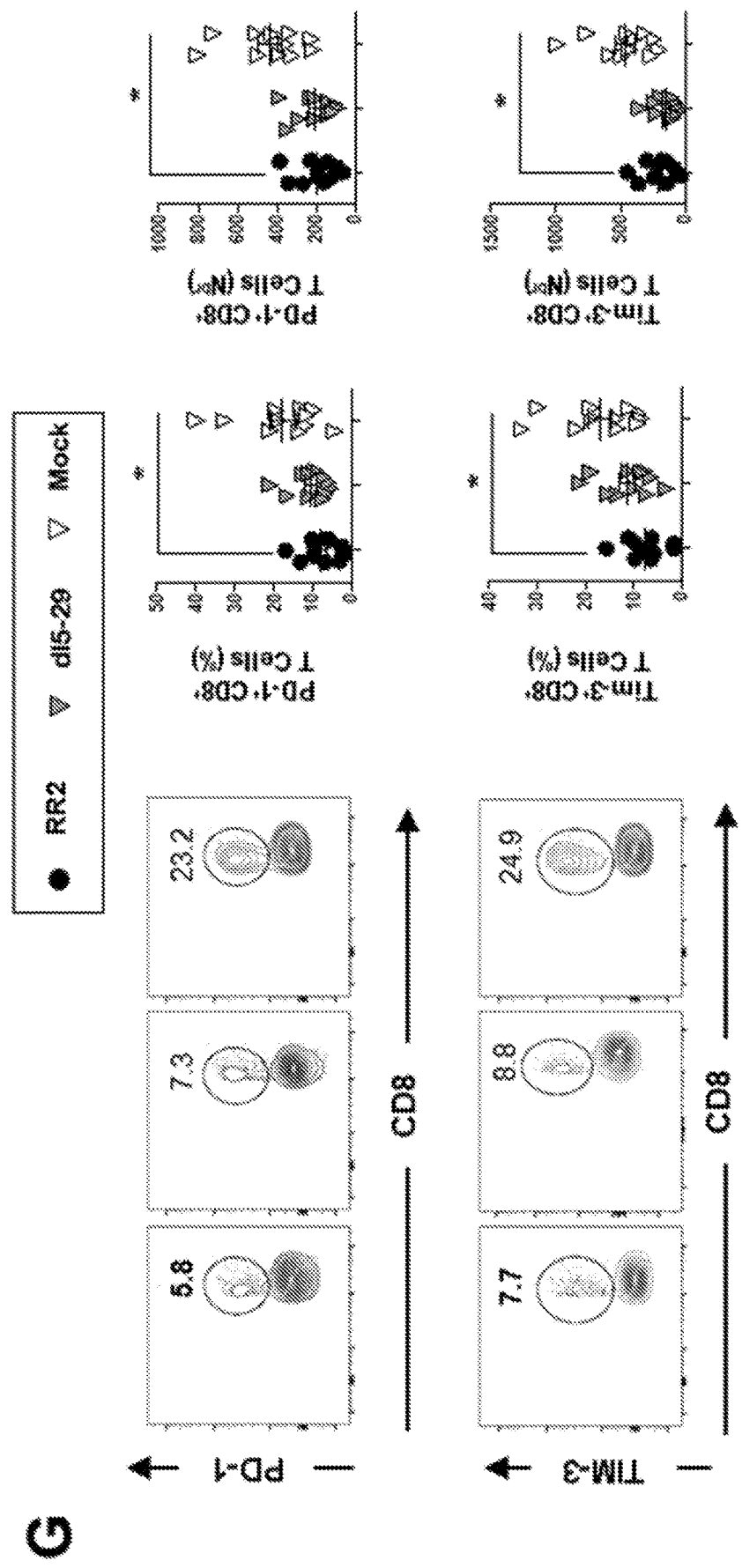

Significantly higher frequencies of functional $CRTAM^+$ $CD8^+$ T cells (top row) and of $CFSE^+CD8^+$ T cells (bottom row) were detected in the VM of RR2 protein-vaccinated animals compared to mock vaccinated animals ($P<0.05$) (FIG. 6F). Significantly higher numbers of IFN-g-producing cells were enumerated ex vivo by the ELISpot assay in the VM of RR2-vaccinated animals compared to mock-vaccinated animals (FIG. 6F, bottom panel). In contrast, lower frequencies of exhausted $PD-1^+CD8^+$ T cells (top panels) and $TIM-3^+CD8^+$ T cells (bottom panels) were detected in the VM of RR2 group compared to mock-vaccinated group, confirming less exhausted and more functional VM-resident T cells following vaccination with the RR2 protein ($P<0.05$). As expected, high numbers of functional $CD4^+$ and $CD8^+$ T cells were detected in the VM of the dl5-29 vaccinated group (positive control) while high numbers of dysfunctional $CD4^+$ and $CD8^+$ T cells were detected in the mock-vaccinated group (negative control) (FIGS. 6F to 6G). Altogether, these results confirmed that therapeutic vaccination of HSV-2 infected guinea pigs with RR2 proteins induced more functional and less exhausted vaginal-mucosa-resident CD4+ and CD8+ T cells associated with a significant reduction of virus shedding and less severe and frequent recurrent genital herpes lesions.

Figures 7A, 7B:
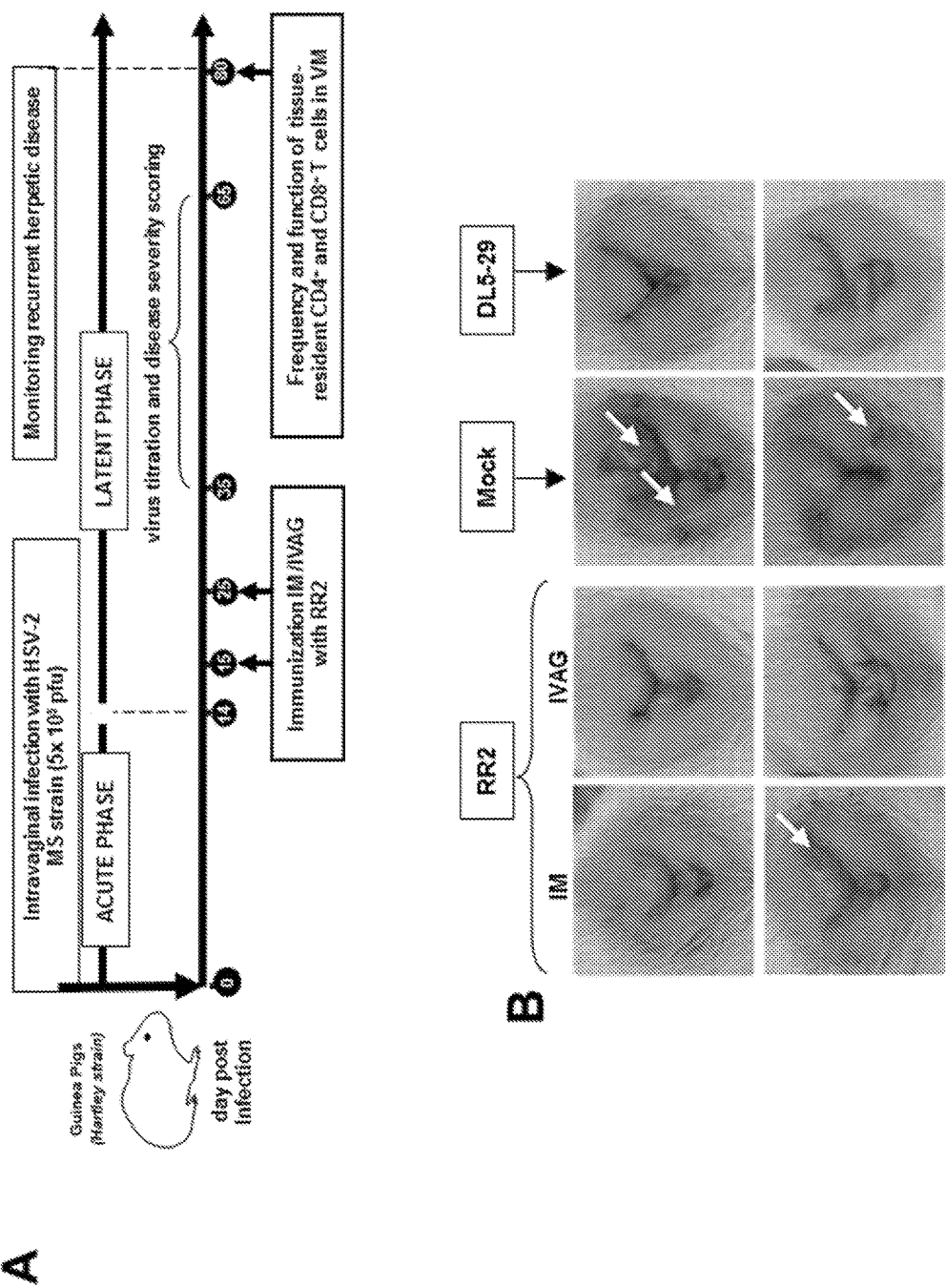
FIG. 7A through FIG. 7F, depicts the results of example experiments demonstrating ntravaginal versus intramuscular immunization of HSV-2 infected guinea pigs with RR2 protein.
Figure 7C:
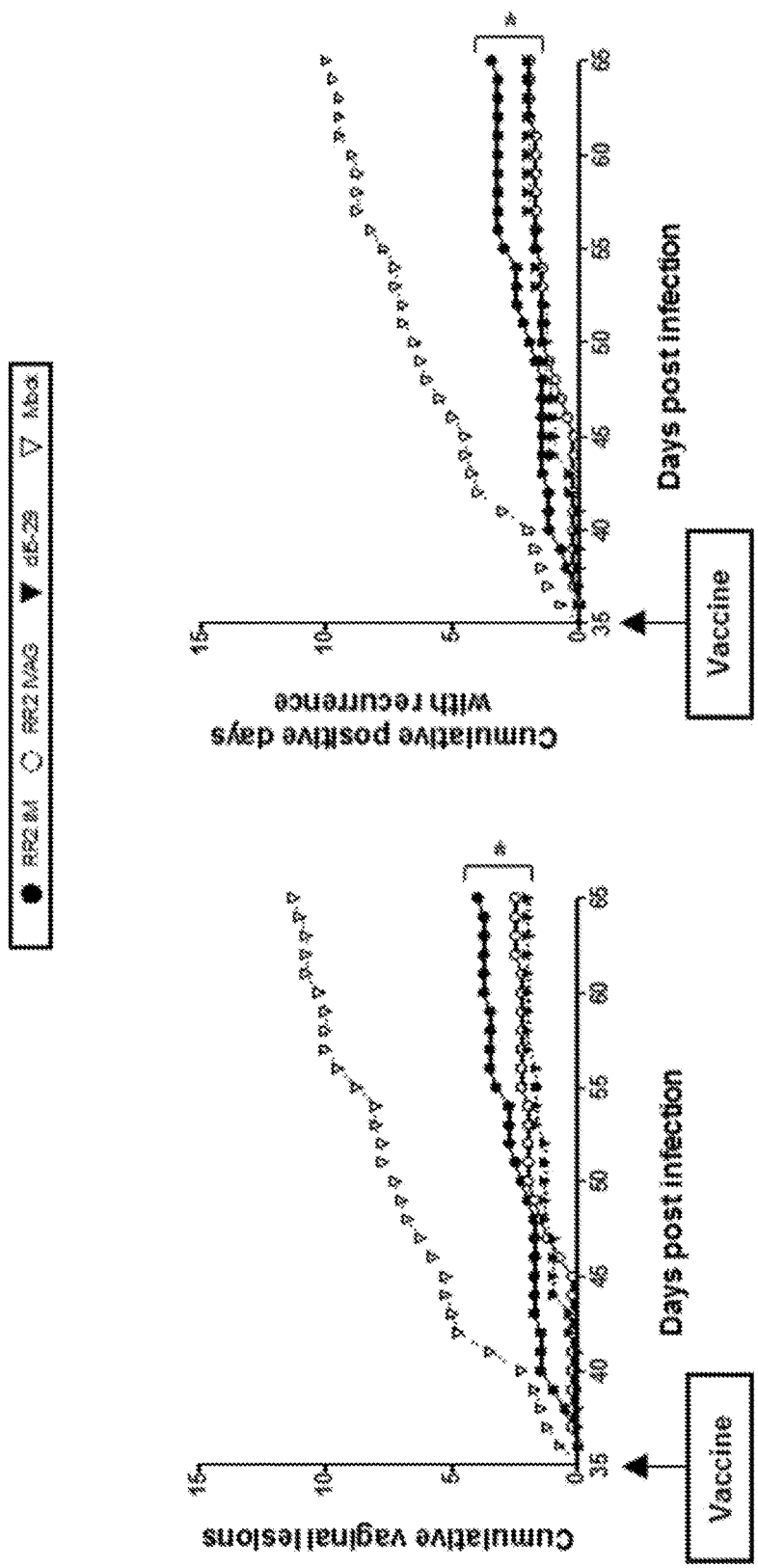
Figure 7D:
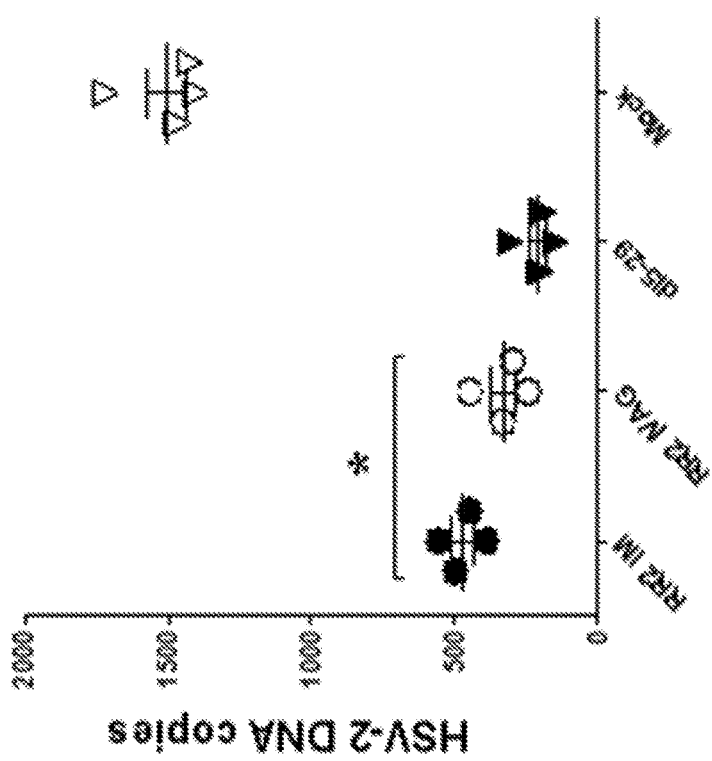
Figure 7E:
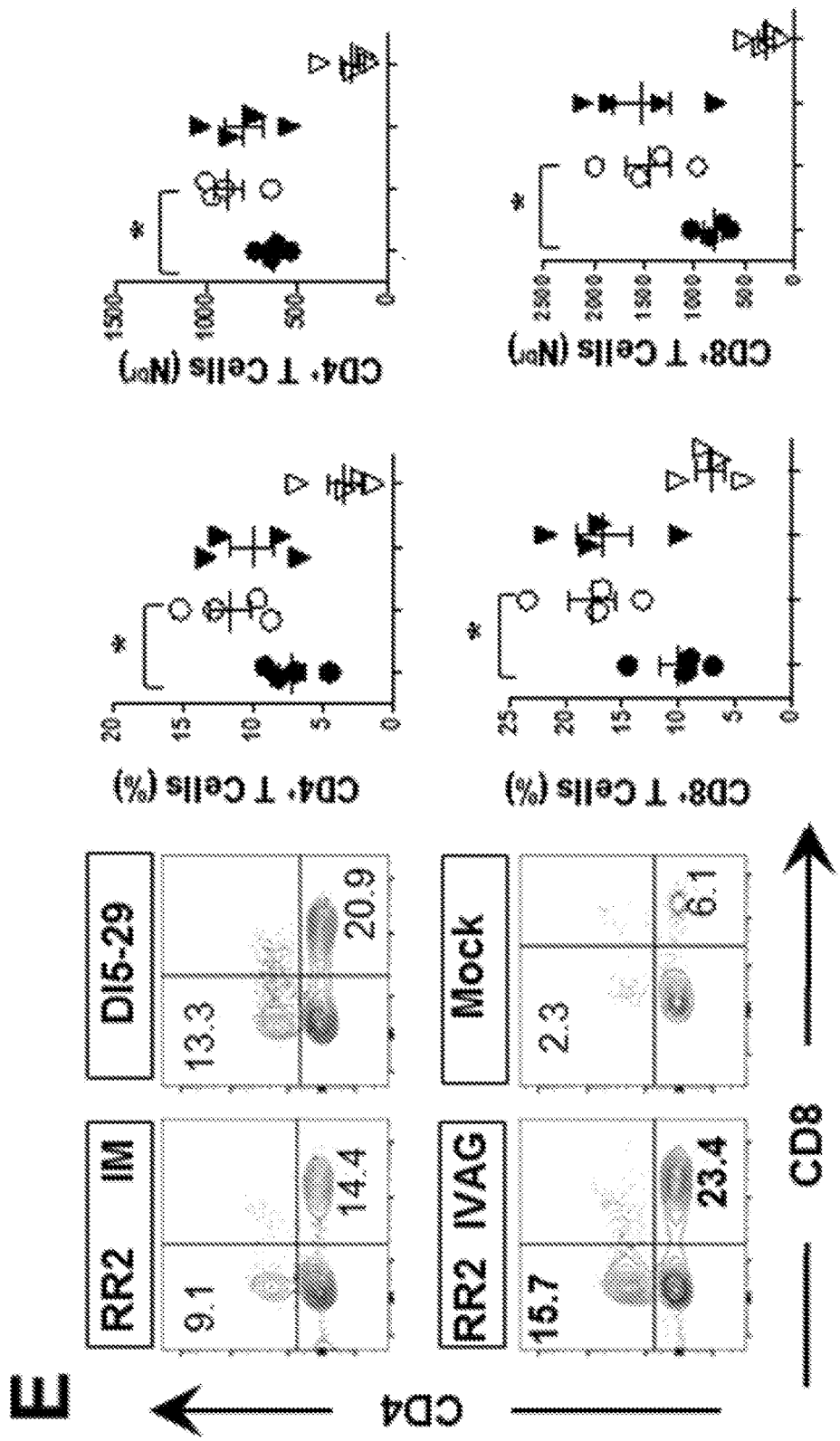
Figure 7F:
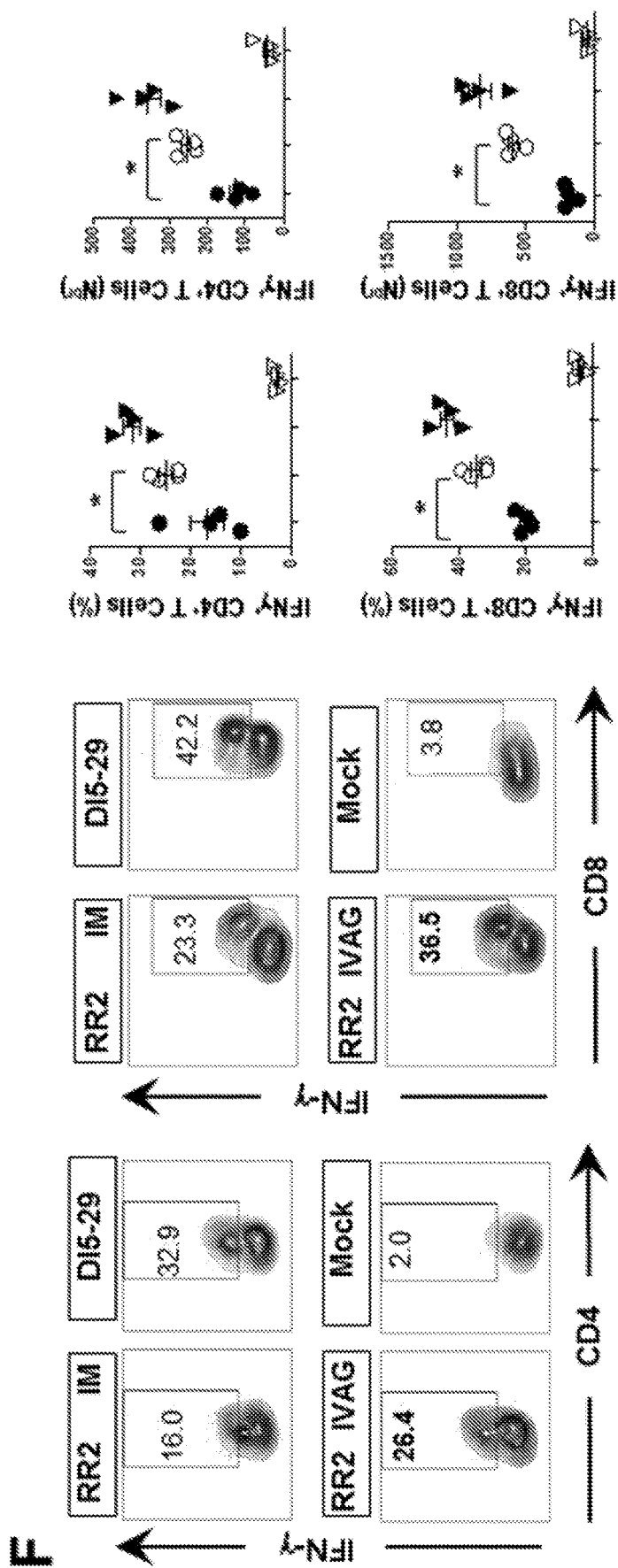

Mucosal Immunization of HSV-2 Infected Guinea Pigs with (RR2) Protein is Superior to Intramuscular Immunization Genital herpes infections and lesions are initiated at mucocutaneous surfaces, yet intramuscular vaccination is often used and usually provide only minimal protection at vaginal sites of infection owing to suboptimal activation of local tissue-resident CD4+ and CD8+ T cells. To optimize the number and function of local CD4+ and CD8+ T cells that would localize to healed sites of the vaginal mucocutaneous tissues, the intravaginal and intramuscular routes of vaccination were compared in HSV-2 infected guinea pigs using the RR2 vaccinogen formulated in CpG and Alum adjuvants. It was found that protection induced following immunization through the intramuscular route was significantly lower than the intravaginal route (FIGS. 7B to 7D). Moreover, significantly increased numbers of vaginal mucosa-resident IFN-g-producing CD4+ and CD8+ T cells were induced following intravaginal immunization compared to intramuscular immunization (FIGS. 7E and 7F). These results indicate that intravaginal immunization may serve as a beneficial gatekeeper for the development of new intravaginal herpes vaccines.

Figures 8A, 8B:
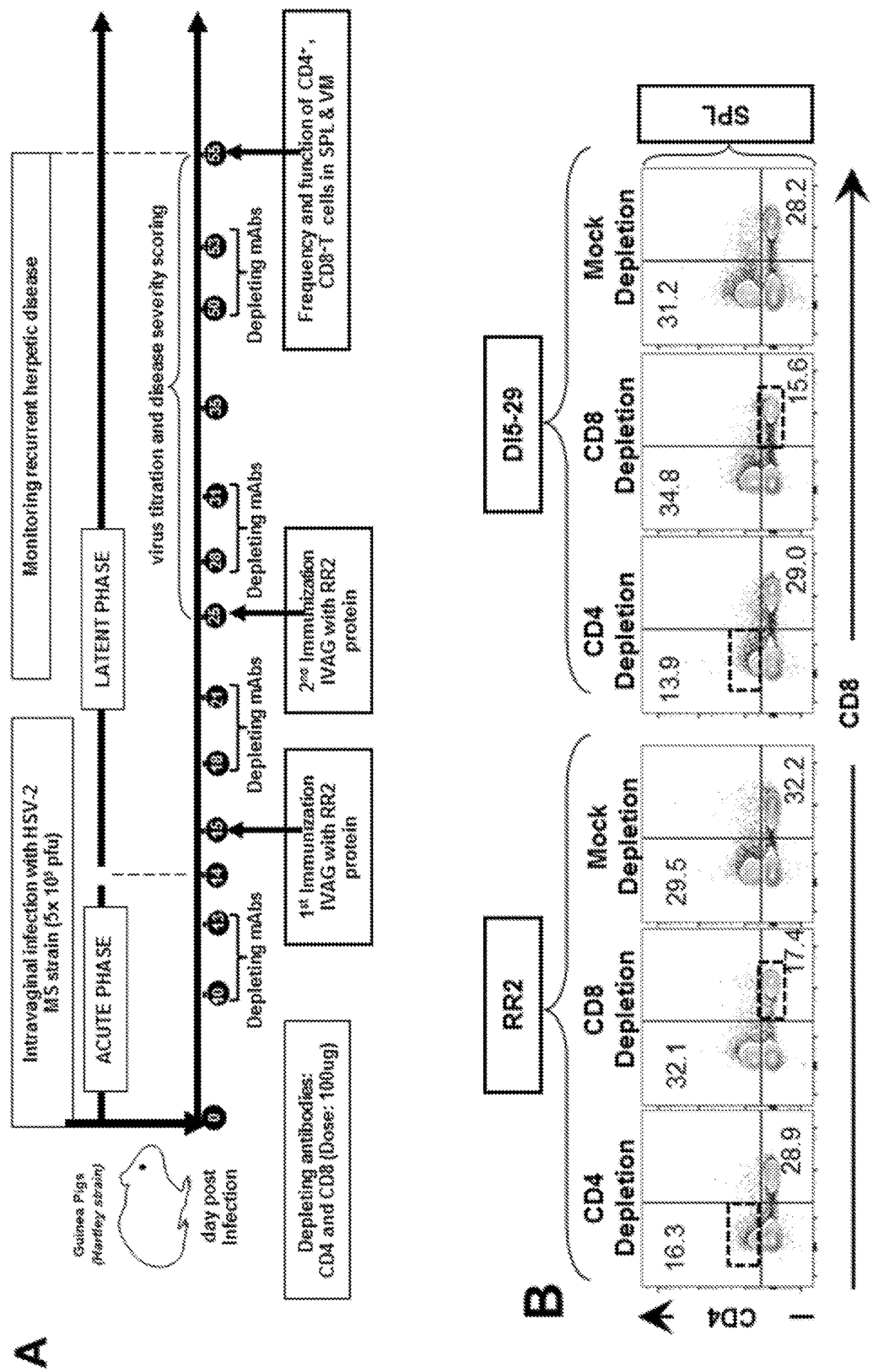
FIG. 8A through FIG. 8G, depicts the results of example experiments demonstrating the effect of CD4 and CD8 depletion on RR2 induced protection against recurrent genital disease.
Figure 8C:
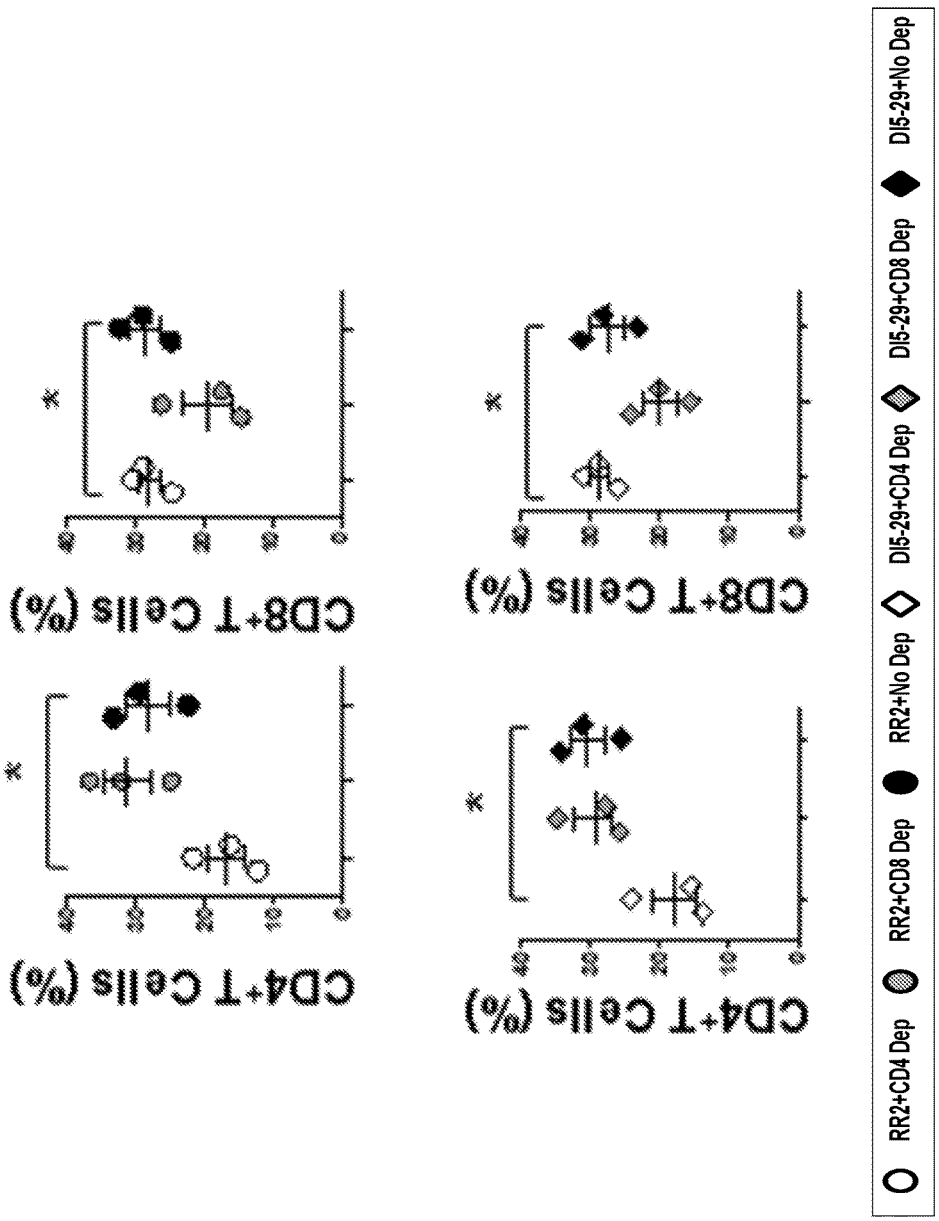
Figure 8D:
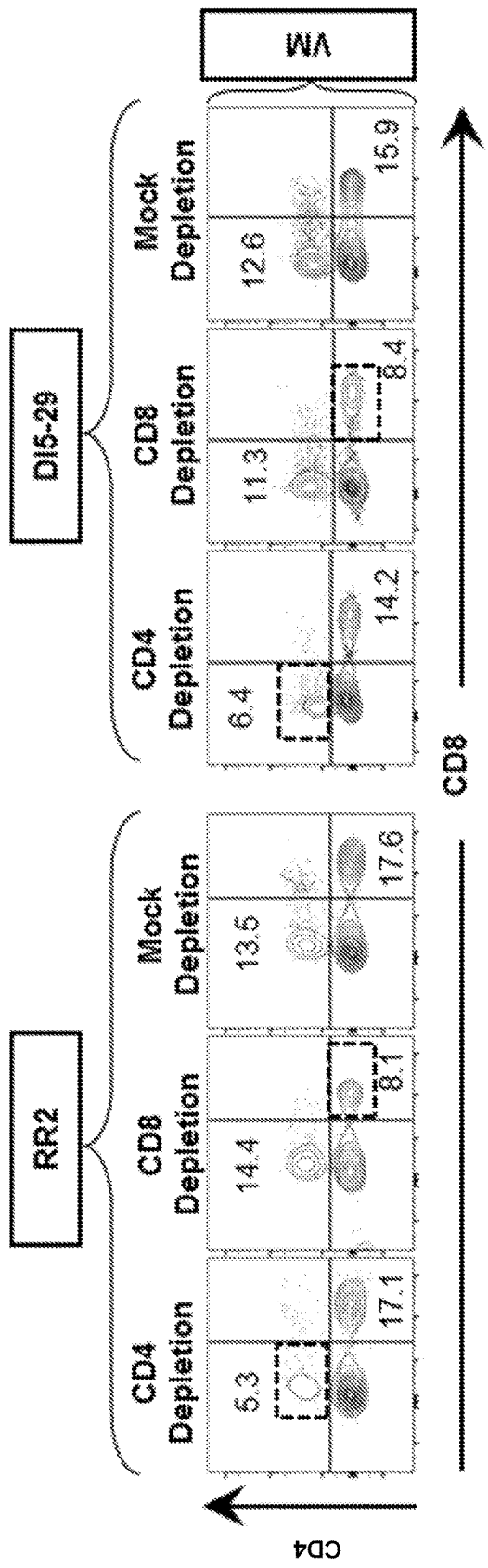
Figure 8E:
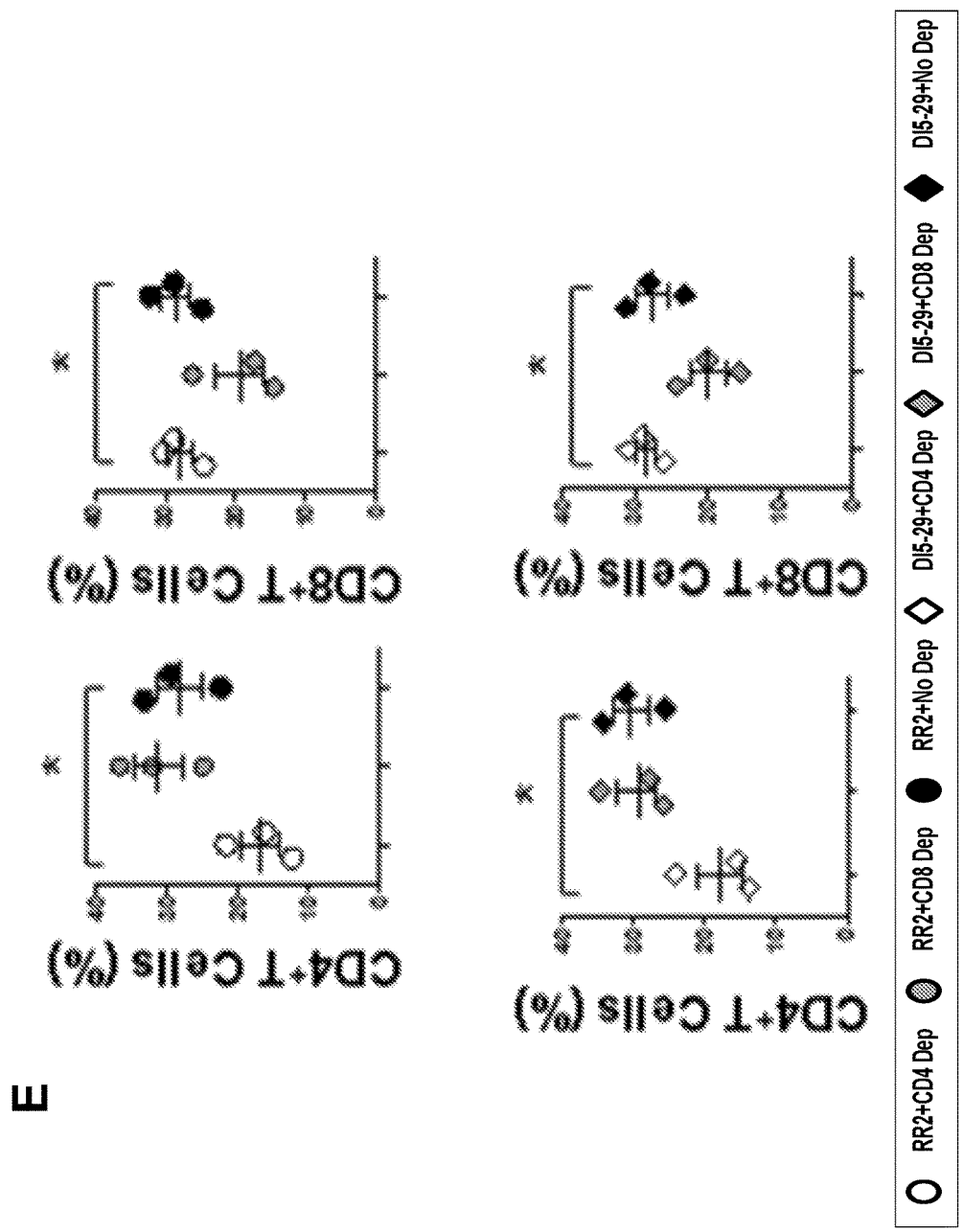
Figure 8F:
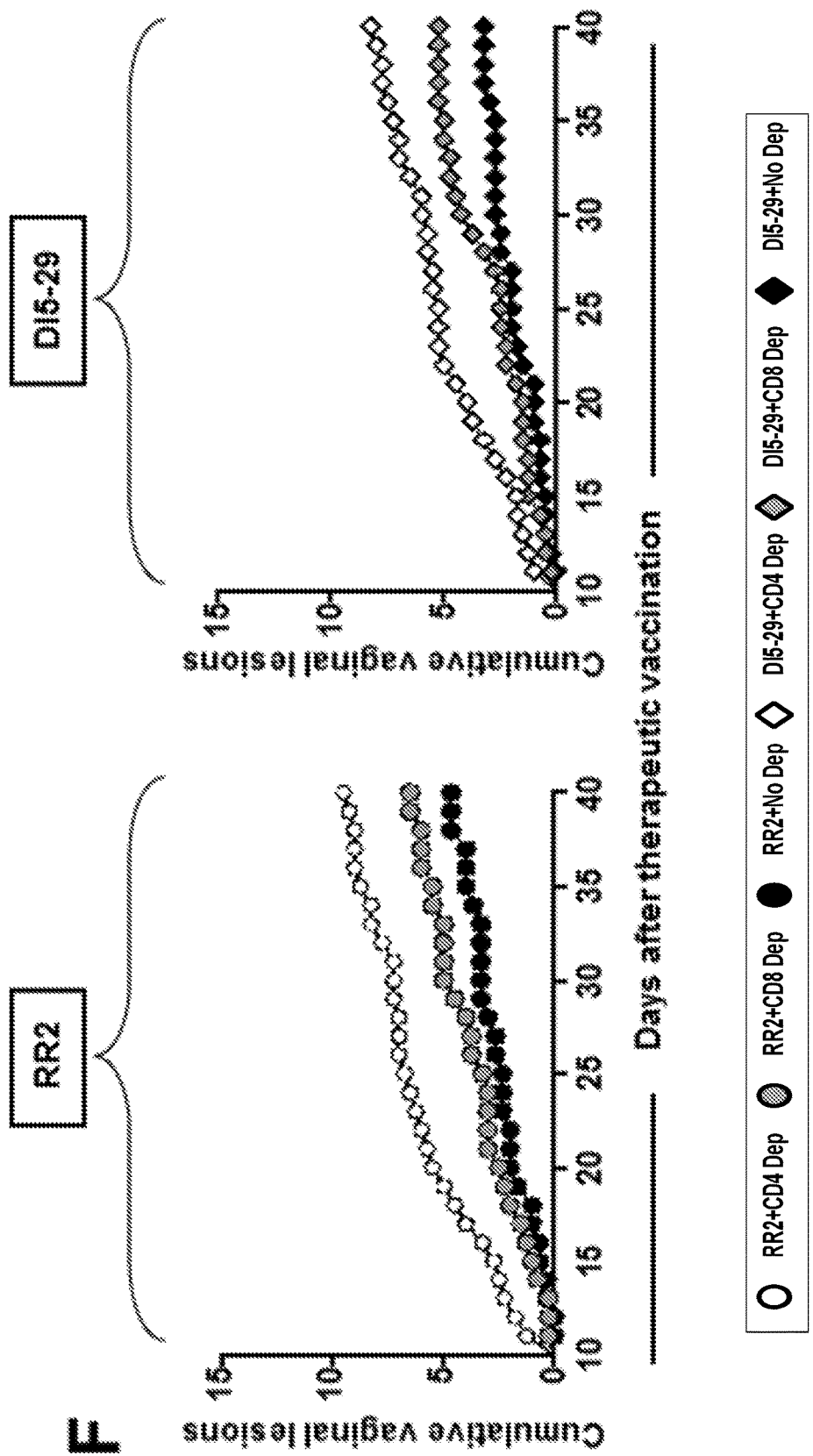
Figure 8G:
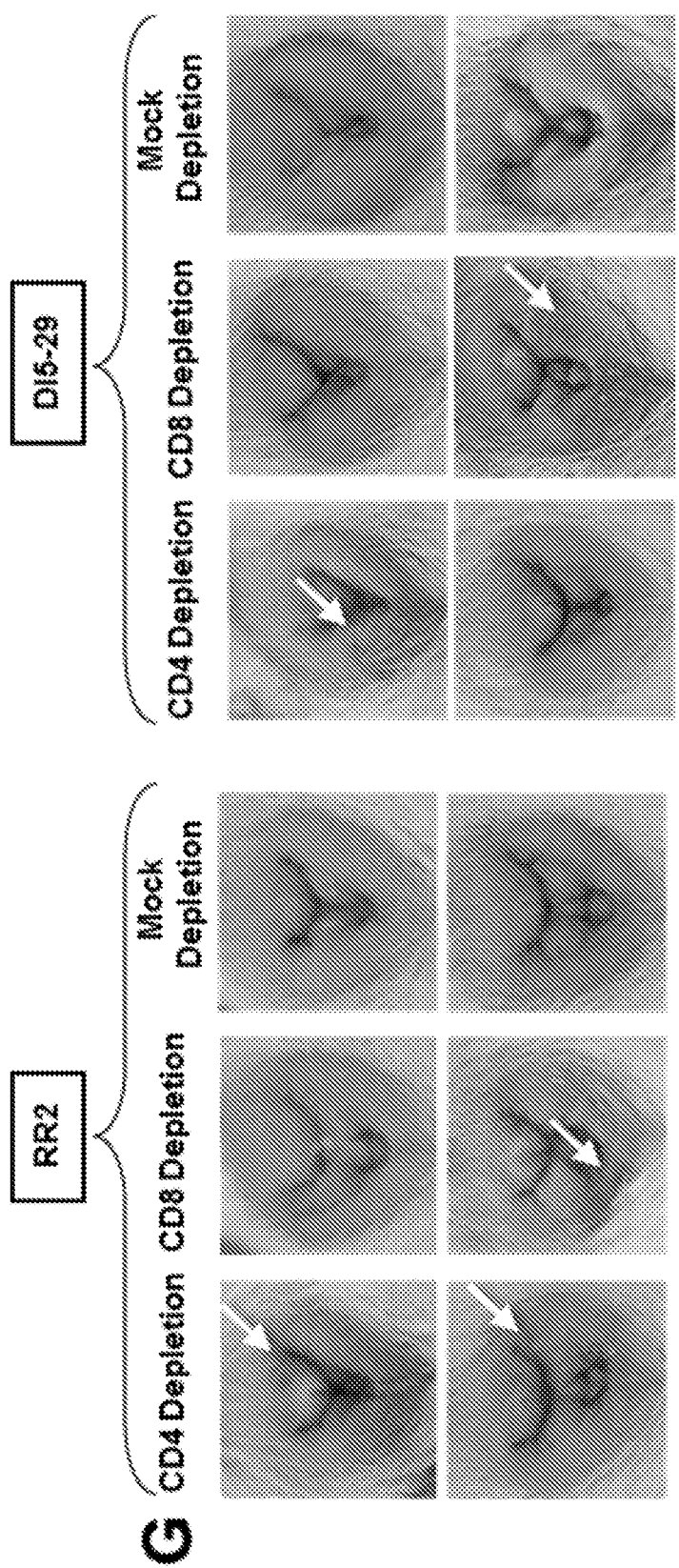

The Protective Immunity Against Recurrent Genital Herpes Infection and Disease Induced Following Therapeutic Immunization with RR2 protein is CD4+ and CD8+ T cell dependent To assess the involvement of CD4+ and CD8+ T cell subsets in the protection induced by IVAG immunization with the RR2 protein, in vivo depletion of either CD4+ or CD8+ T cells was performed in infected guinea pigs before and after each immunization (FIG. 8A). Depletion of CD4+ or CD8+ T cells reduced the number of respective cells in both the spleen (FIGS. 8B and 8C) and vaginal mucosal tissues (FIGS. 8D and 8E), resulting in a significant abrogation in the protection induced by immunization with the RR2 protein or DL5-29 (P<0.05, FIGS. 8F and 8G). This suggest that in this system, both CD4+ and CD8+ T cells are required for protection against genital herpes. Altogether, these results indicate that IVAG therapeutic immunization with the RR2 protein or DL5-29 decreased overt signs of recurrent genital herpes disease. The results also suggest that both the CD4+ and CD8+ T cell mediated immunity were involved in the observed protection.

Figure 9:
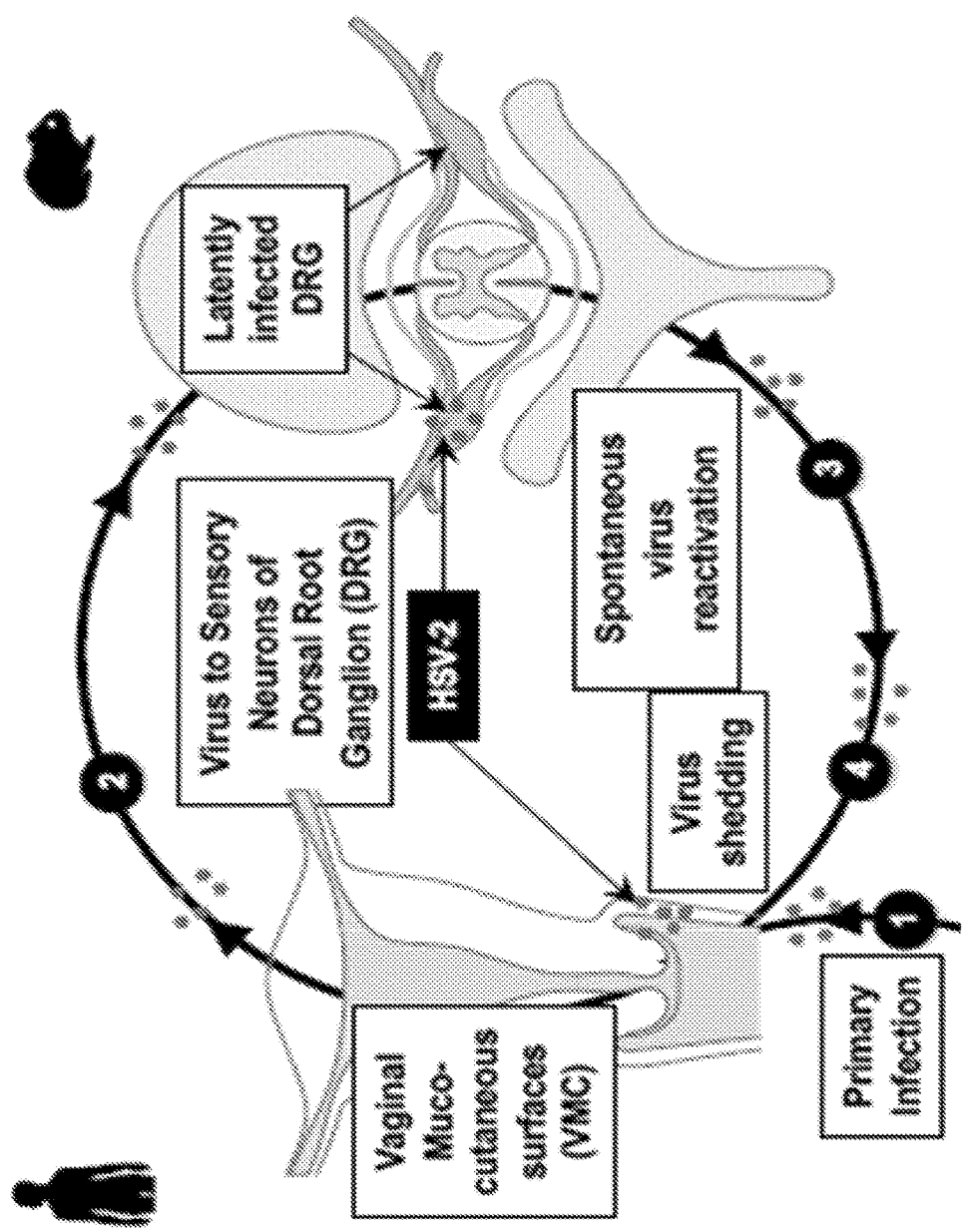
FIG. 9 depicts a diagram showing that the HSV-2 life cycle is similar in humans and the guinea pig model. 1—Primary infection. 2—Virus to latency in DRG. 3—Virus reactivation from DRG. 4—Re-infection of, and virus shedding from VMC.
Figure 10:
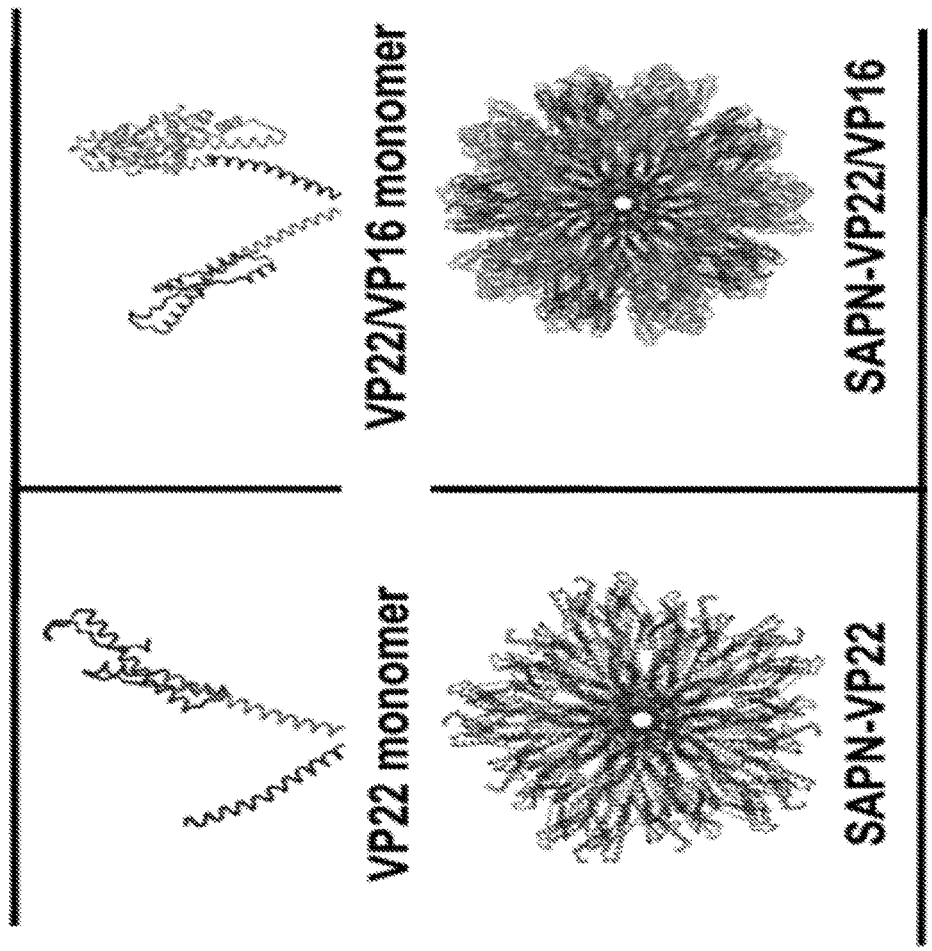
FIG. 10 depicts examples of SAPN-VP22 protein and SAPN-VP22/VP16 combination of two different proteins. Monomers are on top and particles at the bottom.
Figure 11:
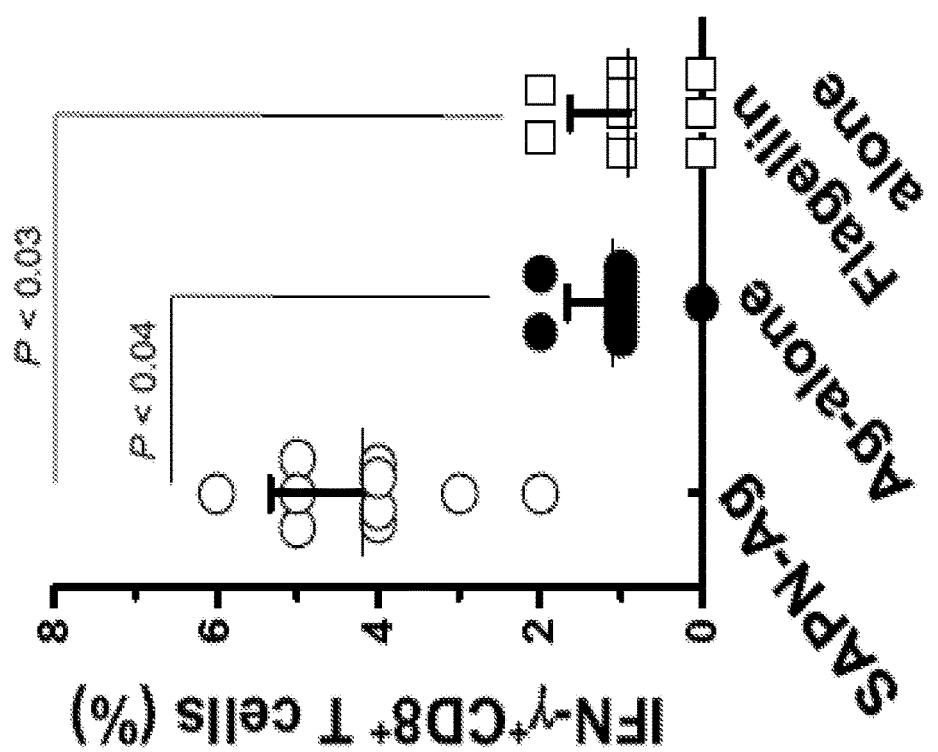
FIG. 11 depicts exemplary experimental results of subcutaneous injection of SAPN-Ag based vaccine induced antiviral IFNγ+CD8+ T cells.

Example 2: A Novel Prime/Pull Therapeutic Vaccine to Prevent Recurrent Genital Herpes Despite several efforts, a safe and efficient genital herpes vaccine is still not available. Virus shedding and re-infection of the VMC may be either (1) Asymptomatic (ASYMP), with mild and unrecognized disease (Koutsky et al., 1992, N Engl J Med, 326:1533-9); or (2) Symptomatic (SYMP), with severe and painful mucocutaneous genital lesions leading to complications including urinary retention and a substantial psychological illness (Reeves et al., 1981, N Engl J Med, 305: 315-9; Corey et al., 1978, N Engl J Med, 299:237-9). Lifecycle of genital HSV-2 infection is shown in FIG. 9. Despite widely used methodologies to control genital herpes, including antiviral drugs (Acyclovir and derivatives), education, and the use of condoms, the spread of genital herpes infection remains an epidemic in some populations (Fleming et al, 1997, N Engl J Med, 337:1105-11; Stanberry et al, 1999, Antiviral Res, 42:1-14; Stanberry et al., 2000, Clin Infect Dis, 30: 549-66). A body of evidence suggests that only the widespread use of an effective vaccine can prevent or reduce symptomatic disease and eliminate or at least limit asymptomatic viral shedding, which may in turn help control the herpes simplex epidemic (Stanberry et al, 1999, Antiviral Res, 42:1-14; Stanberry et al., 2000, Clin Infect Dis, 30: 549-66; Cunningham et al., 2012, J Clin Virol, 53:6-11; Stanberry et al., 2002, N Engl J Med, 347:1652-61).

The goal of this translational project was to develop a prime/pull therapeutic genital herpes vaccine, using new antigen delivery systems, to boost the number and function of antiviral tissue-resident memory CD4+ and CD8+ T cells. The insights gained from this translational vaccine informed the design of a prime/pull therapeutic genital herpes vaccine for clinical use.

The results of the experiments are now described.

Figures 15A, 15B:
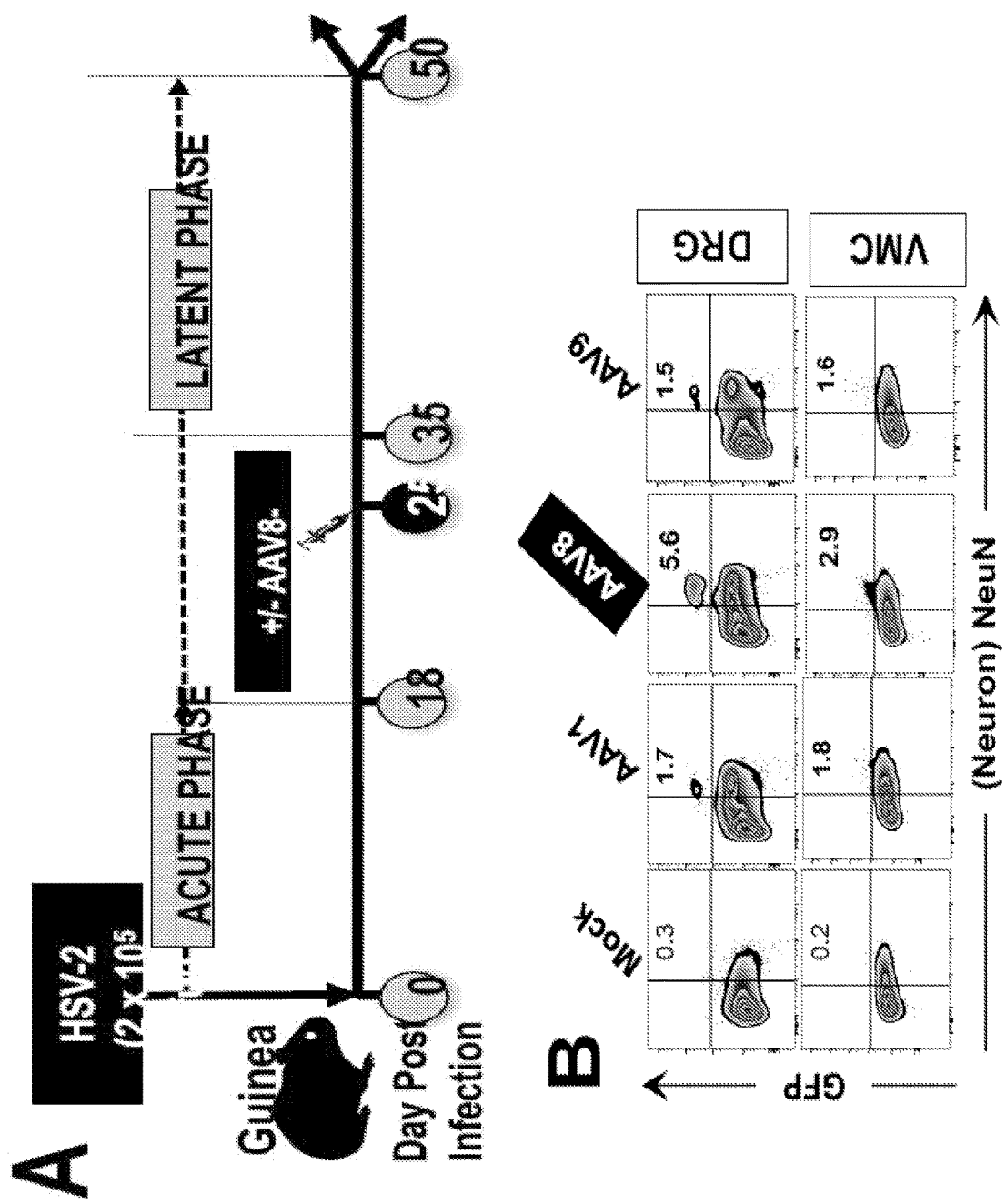
FIG. 15A through FIG. 15C depicts data demonstrating successful delivery and expression of GFP in the DRG and VMC of HSV-2 infected guinea pigs after footpad injection of AAV8 vector, compared to AAV1 and AAV9 vectors.
Figure 15C:
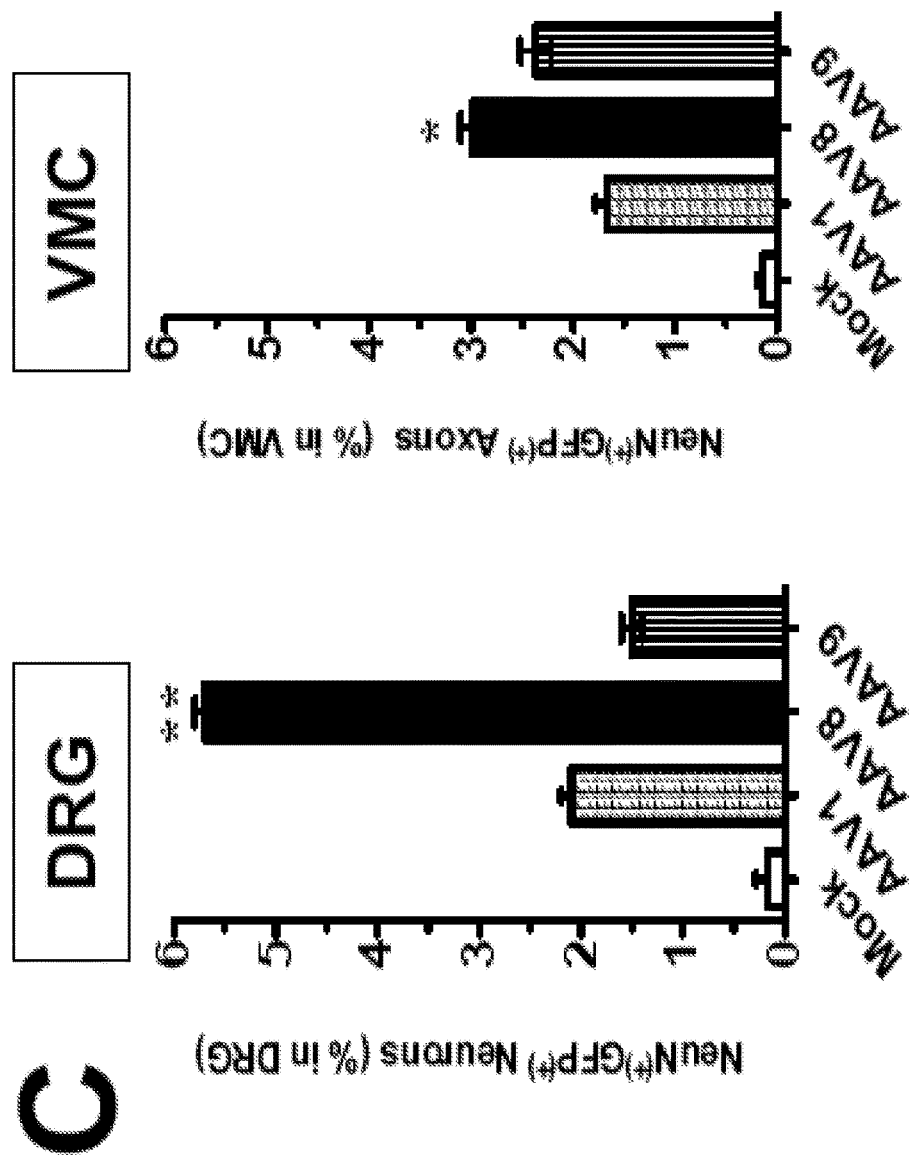
Figure 16:
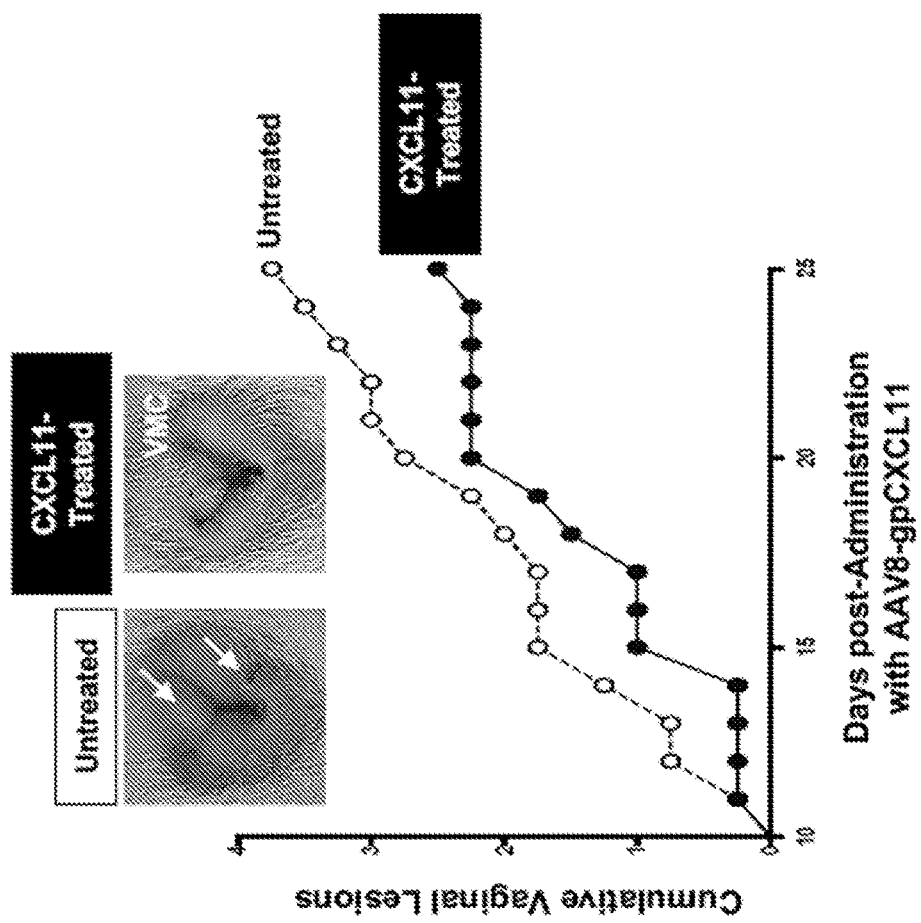
FIG. 16 depicts data demonstrating that treatment of HSV-2 infected guinea pigs with CXCL11 reduced recurrent genital herpes disease. Arrows=Herpes lesions.
Figure 17:
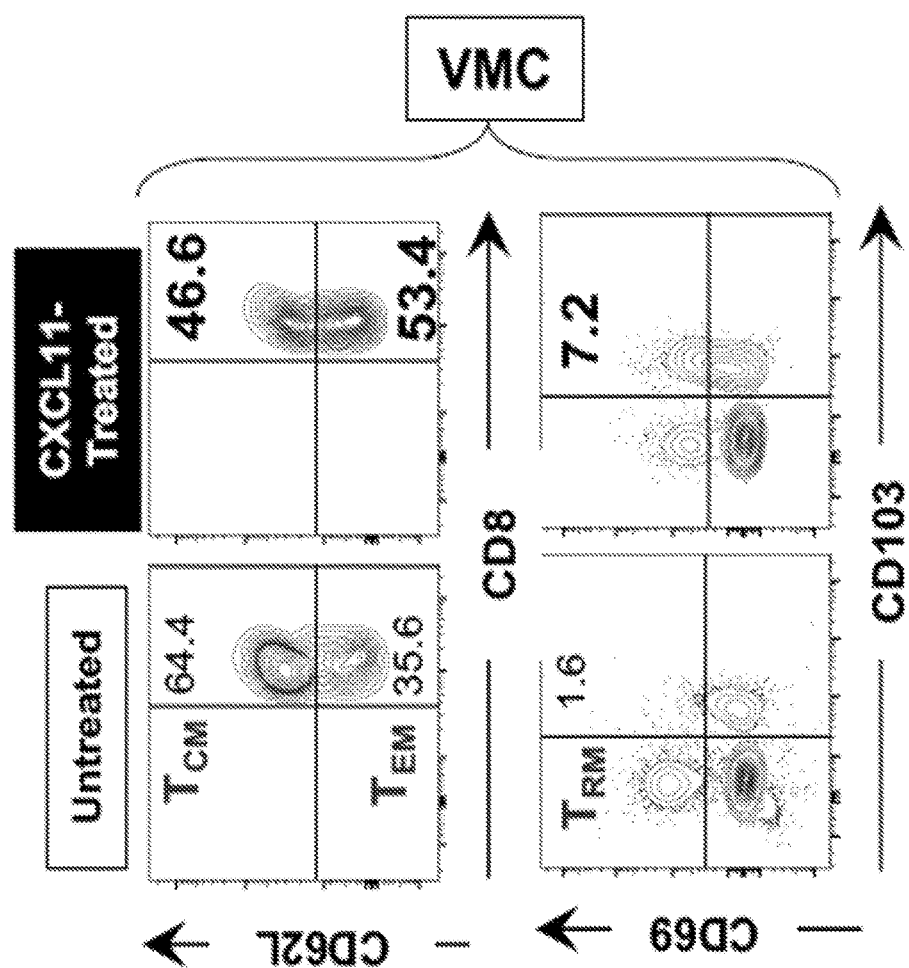
FIG. 17 depicts data demonstrating that treatment of HSV-2 infected guinea pigs with CXCL11 was associated with increased frequency of VMC issue-resident memory TRM cells and effector memory TEM cells. Gates on CD44pos cells.
Figures 19A, 19B:
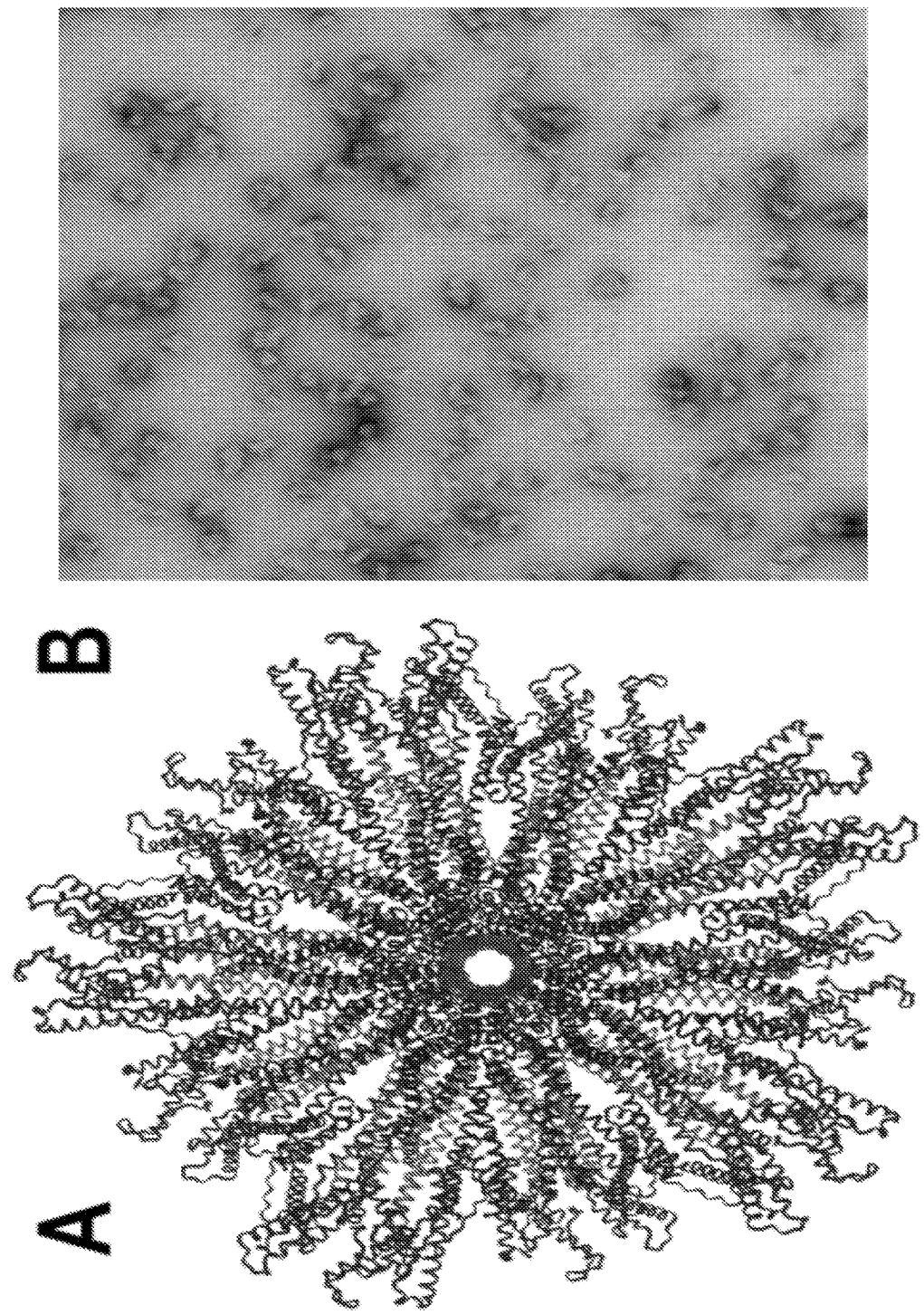
FIG. 19A and FIG. 19B depict diagrams of the SAPN-VP22 vaccine particle.

Antigen Selection and Self-Assembling Protein Nanoparticles (SAPNs) Delivery System that Targets both Endogenous (MHC-I) and Exogenous (MHC-II) Pathways A proteomic library containing a near-complete collection of the HSV-2 84+ open reading frames (ORFome) of HSV-2 has been cloned and corresponding proteins expressed individually (Kalantari-Dehaghi, et al., 2012, J Virol, 86: 4328-39; Dasgupta et al., 2012, J Virol, 86: 4358-69). HSV-2 protein antigens recognized by T cells from "naturally protected" seropositive individuals, resistant to recurrent genital herpetic disease despite being infected—were selected as antigen targets for designing a protein-based subunit herpes prime/pull vaccine for this project. A set of four HSV-2 Ags, VP16, VP22, RR1 and RR2 tegument and regulatory proteins, were recognized mostly by CD4+ and CD8+ cells from "naturally protected" ASYMP individuals (Example 1). Moreover, VP16, VP22, RR1 and RR2 based vaccines induced both HSV-2 neutralizing antibodies and antiviral vaginal mucosa-resident CD4+ and CD8+ T cells (Example 1). Spherical self-assembling protein nanoparticle (designated as SAPNs)-Ag-based vaccines have been reported to induce protective antibody CD4+ and CD8+ T-cell responses in other systems (Burkhard et al., 2015, Expert Rev Vaccines, 14: 1525-7; Doll et al., 2015, Nanomedicine, 11:1705-13; El Bissati et al., 2014, Vaccine, 32: 3243-8; El Bissati et al., 2017, NPJ Vaccines, 2: 24; Guo et al. 2013, Methods, 60: 242-7; Kaba et al., 2009, J Immunol, 183: 7268-77; Kaba et al., 2018, Vaccine, 36: 906-14; Kaba et al., 2012, PLoS One, 7: e48304; Karch et al., 2017, J Nanobiotechnology, 15: 62; McCoy et al., 2013, Malar J, 12: 136; Seth et al., 2017, Vaccine, 35: 5448-54). A SAPN delivery system was selected as it presents protein antigens to both exogenous (MHC-II) and endogenous (MHC-I) pathways, via a cross-presentation mechanism (Burkhard et al., 2015, Expert Rev Vaccines, 14: 1525-7; Doll et al., 2015, Nanomedicine, 11:1705-13; El Bissati et al., 2014, Vaccine, 32: 3243-8; El Bissati et al., 2017, NPJ Vaccines, 2: 24; Guo et al. 2013, Methods, 60: 242-7; Kaba et al., 2009, J Immunol, 183: 7268-77; Kaba et al., 2018, Vaccine, 36: 906-14; Kaba et al., 2012, PLoS One, 7: e48304; Karch et al., 2017, J Nanobiotechnology, 15: 62; McCoy et al., 2013, Malar J, 12: 136; Seth et al., 2017, Vaccine, 35: 5448-54). These nanoparticle-based vaccines are better able to present VP16, VP22, RR1, and RR2 protein antigens to the immune system in vivo. In these nanoparticles, a repetitive antigen display technology relies on the self-assembly of 60 protein chains into SAPNs, which protects these proteins from premature proteolytic degradation, and facilitates their uptake and processing by antigen presenting cells. In addition, SAPN technology is designed to eliminate toxicity and safety issues associated with the use of external immuno-adjuvants by incorporating portions of the TLR5 agonist flagellin, as a built-in immuno-adjuvant. By combining different molar ratios of VP16, VP22, RR1, and RR2 into portions of flagellin monomers before self-assembly, multiple nanoparticles were generated and their biophysical characteristics were investigated. Thus, the VP16, VP22, RR1, RR2 and gD proteins were assembled either as single HSV-2 protein together with flagellin (example of SAPN-VP22 nanoparticles shown in FIG. 10, left panel and FIG. 19) or as combinations of 2 different HSV-2 proteins together with flagellin (example of SAPN-VP16/VP22 nanoparticle shown in FIG. 10, right panel). Subcutaneous injection of a prototype SAPN vaccine induced significant IFNγ$CD8^+$ T-cell responses (FIG. 11). This result confirms and extends previous reports that SAPN protein-based vaccines induced protective $CD4^+$ and $CD8^+$ T-cell responses in other systems (Burkhard et al., 2015, Expert Rev Vaccines, 14: 1525-7; Doll et al., 2015, Nanomedicine, 11:1705-13; El Bissati et al., 2014, Vaccine, 32: 3243-8; El Bissati et al., 2017, NPJ Vaccines, 2: 24; Guo et al. 2013, Methods, 60: 242-7; Kaba et al., 2009, J Immunol, 183: 7268-77; Kaba et al., 2018, Vaccine, 36: 906-14; Kaba et al., 2012, PLoS One, 7: e48304; Karch et al., 2017, J Nanobiotechnology, 15: 62; McCoy et al., 2013, Malar J, 12: 136; Seth et al., 2017, Vaccine, 35: 5448-54).

The CXCL9, CXCL10, CXCL11/CXCR3 Axis for T Cell Activation: A Target for a Novel Prime/Pull Therapeutic Herpes Vaccine:

Chemokines are proteins that induce chemotaxis, promote T cell differentiation, and cause tissue extravasation (Zlotnik et al., 2012, Immunity, 36: 705-16). CXCL-9, -10, and -11 are mainly secreted by monocytes, endothelial cells, and fibroblasts (Ohmori et al., 1997, J Biol Chem, 272: 14899-907). CXCL9 and CXCL10 expression is critical for control of genital HSV-2 infection while CXCR3 deficiency increases susceptibility to HSV-2 infection (Thapa et al., 2008, J Immunol, 180: 1098-106; Thapa et al., 2009, J Virol, 83: 9486-501; Wuest et al., 2011, J Neuroimmunol, 234: 103-8). Intravaginal administration of CXCL10 chemokine in non-infected immunized mice attracted T cells to VMC and protect from HSV-2 challenge (Shin et al., 2012, Nature, 491: 463-7). Using several molecular biology and immunological assays, it was demonstrated that the CXCL9, CXCL10, CXCL11/CXCR3 axis is highly activated in DRG and healed VMC of HSV-2 infected and protected guinea pigs (i.e., asymptomatic) compared to non-protected guinea pigs that present severe genital herpes symptoms (FIG. 12B to FIG. 12E). RNA-Seq results revealed that similar to HSV-2 VP16-specific $CD8^+$ T cells in asymptomatic humans (FIG. 12A), elevated levels of the CXCR3 receptor gene in tissue-resident $CD8^+$ T cells FACS-sorted from DRG of HSV-2 infected and protected vs. non-protected guinea pigs (FIG. 12B). In contrast, RNA-Seq showed a modest upregulation of CCR5 and CCR10 receptor genes in T cells from protected compared to non-protected guinea pigs. Moreover, phenotypic profiling of latently healed VMC-resident T cells in protected guinea pigs showed frequent $CXCR3^+$ $CD4^+$ and $CXCR3^+$ $CD8^+$ T cells, compared to non-protected guinea pigs (FIG. 12C). Western blot and immunostaining confirmed significant expression of the CXCL9, CXCL10, CXCL11 chemokines in healed VMC of HSV-2 infected and protected guinea pigs (FIG. 12D and FIG. 12E) suggesting that the CXCL9, CXCL10, CXCL11/CXCR3 axis is involved in activating antiviral tissue-resident $CD4^+$ and $CD8^+$ T cell responses locally in DRG (FIG. 12F) and VMC. Without being bound by theory, it was hypothesized that successful HSV therapeutic vaccination attracts large numbers of protective T cells to the affected DRG and VMC.

Identifying the Neurotropic Adeno-Associated Virus Serotype 8 (AAV8) as a Vector for Increasing Numbers of Protective T Cell in the Guinea Pigs' DRG and VMC AAV vectors are useful vehicles for delivering transgenes to infected tissues and organs in vivo (Bloom et al., 2019, Methods Mol Biol, 1950: 237-47; Watson et al., 2016, J Virol, 90: 7894-901; Khan et al., 2017, J Immunol, 199: 186-203). Recently, there has been much progress in delivering AAV vectors to sensory neurons following application to the peripheral epithelium, such as skin or eye (Bloom et al., 2019, Methods Mol Biol, 1950: 237-47; Watson et al., 2016, J Virol, 90: 7894-901; Khan et al., 2017, J Immunol, 199: 186-203). This delivery requires scratching the epithelium to access the underlying nerve termini. AAV1-GFP, AAV8-GFP, and AAV9-GFP vectors were compared in HSV-2 infected guinea pig and the AAV8-GFP vector was found to be superior at 8 days after footpads inoculation (FIG. 13-FIG. 15). Compared to intravaginal, a better transduction in DRG and VMC was obtained following footpad inoculation (FIG. 15C). Moreover, a neurotropic AAV8 expressing GFP and the guinea pigs' T cell-attracting CXCL11 chemokine, both under the neurotropic human synapsin 1 gene promoter (hSYN) (AAV8-hSYN-eGFP-hSYN-gpCXCL11 vector) (FIG. 13), resulted in specific transduction of guinea pigs DRG and VMC tissues. Moreover, the AAV8 vector expressing the guinea pigs' CXCL11 chemokine (a CXCR3 ligand) specifically in infected DRG tissue reduced recurrent genital herpes lesions (FIG. 16) associated with increased the number of antiviral tissue-resident $CD4^+$ and $CD8^+$ $T_{RM}$ and $T_{EM}$ cells (FIG. 17).

Prime/Pull Therapeutic Vaccine

Increased number and function of DRG- and VMC-resident CD4+ and CD8+ T cells was associated with reduced severity and rate of recurrent genital herpes. To date, no study has reported the effect of expression of T cell attracting chemokines on DRG-resident T cells and how that affects recurrent infection and disease. Preliminary data indicate that intravaginal inoculation of HSV-2-infected guinea pigs with a neurotropic AAV8 vector expressing the guinea pigs' CXCL11 chemokine under the neurotropic hSYN promoter (AAV8-hSYN-eGFP-hSYN-gpCXCL11 vector) (FIG. 13), increased the pool of DRG- as well as of VMC-resident CD4+ and CD8+ T cells (FIG. 17, FIG. 23, FIG. 24 and FIG. 25). This was associated with a significant decrease recurrent genital herpes disease (FIG. 16). These data support the hypothesis that a successful HSV therapeutic vaccine attracts large numbers of protective T cells to the affected DRG and VMC.

On day 18 post-infection, latently infected guinea pigs (n=20) receive: (a) Sub-cutaneous (SC) injection of 50 μg of SAPNs particles expressing HSV-2 antigens (i.e., VP16, VP22, RR1, RR2, or gD protein (as shown in FIG. 10 and FIG. 19); and (b) on day 25 post-infection foot-pad (FP) inoculation with 5×106 pfu of AAV8 vector expressing T-cell attracting chemokines, CXCL9, CXCl10 and/or CXCL11 (FIG. 20). Footpad inoculation of AAV8 was chosen, instead of intravaginal administration, because this route showed better transduction of DRG and VMC (FIG. 15). The SAPNs delivery stem was selected as it presents protein antigens to both exogenous (MHC-II) and endogeous (MHC-I) pathways, via a cross-presentation mechanism (Burkhard et al., 2015, Expert Rev Vaccines, 14: 1525-7; Doll et al., 2015, Nanomedicine, 11:1705-13; El Bissati et al., 2014, Vaccine, 32: 3243-8; El Bissati et al., 2017, NPJ Vaccines, 2: 24; Guo et al. 2013, Methods, 60: 242-7; Kaba et al., 2009, J Immunol, 183: 7268-77; Kaba et al., 2018, Vaccine, 36: 906-14; Kaba et al., 2012, PLoS One, 7: e48304; Karch et al., 2017, J Nanobiotechnology, 15: 62; McCoy et al., 2013, Malar J, 12: 136; Seth et al., 2017, Vaccine, 35: 5448-54). The neurotropic AAV8 vector was selected because: (i) it is safe. Clinical trials using AAV vectors in gene therapies have shown only mild and transient inflammation while demonstrating clinical benefits (Flotte et al., 2011, Hum Gene Ther. (2011); 22: 1239-47); and (ii) it is efficient and specific in delivering chemokines to sensory neurons of the DRG (Liu et al., 2008, J Virol, 82: 7467-74; Foust et al., 2008, Hum Gene Ther, 19: 61-70; Zheng et al., 2010, Neurosignals, 18: 49-56). AAV8-GFP persistently expressed GFP both in the cell body of neurons (DRG) and in the axon termini (VMC) of guinea pigs latently infected with HSV-2 (FIG. 15A); and (iii) AAV8 vector can accommodate up to 4.7 kb of DNA expressing multiple chemokines. Thirty-two different groups of HSV-2 infected guinea pigs (n=20/group) are treated as shown in FIG. 18. Virologic and clinical impact in guinea pigs that receive the prime/pull vaccine (n=20) is compared to the replication-defective HSV-2 d15-29 mutant virus (i.e., d15-29 vaccine) used as a positive control (n=20). To ensure the safety, the group of animals that received the lead vaccine out of 18 candidates (n=20), are monitored up to 12 months post-immunization for potential short-term local reactogenicity (e.g., swelling, inflammation, and redness at injection site) and long-term unwanted systemic side effects (e.g., loss of food consumption and reduction of body weight). Any undesirable side effect is recorded and followed by histopathological examinations of pivotal organs (e.g., brain, sensory ganglia, and VMC).

Monitoring Genital Herpes Infection and Disease

Figure 20:
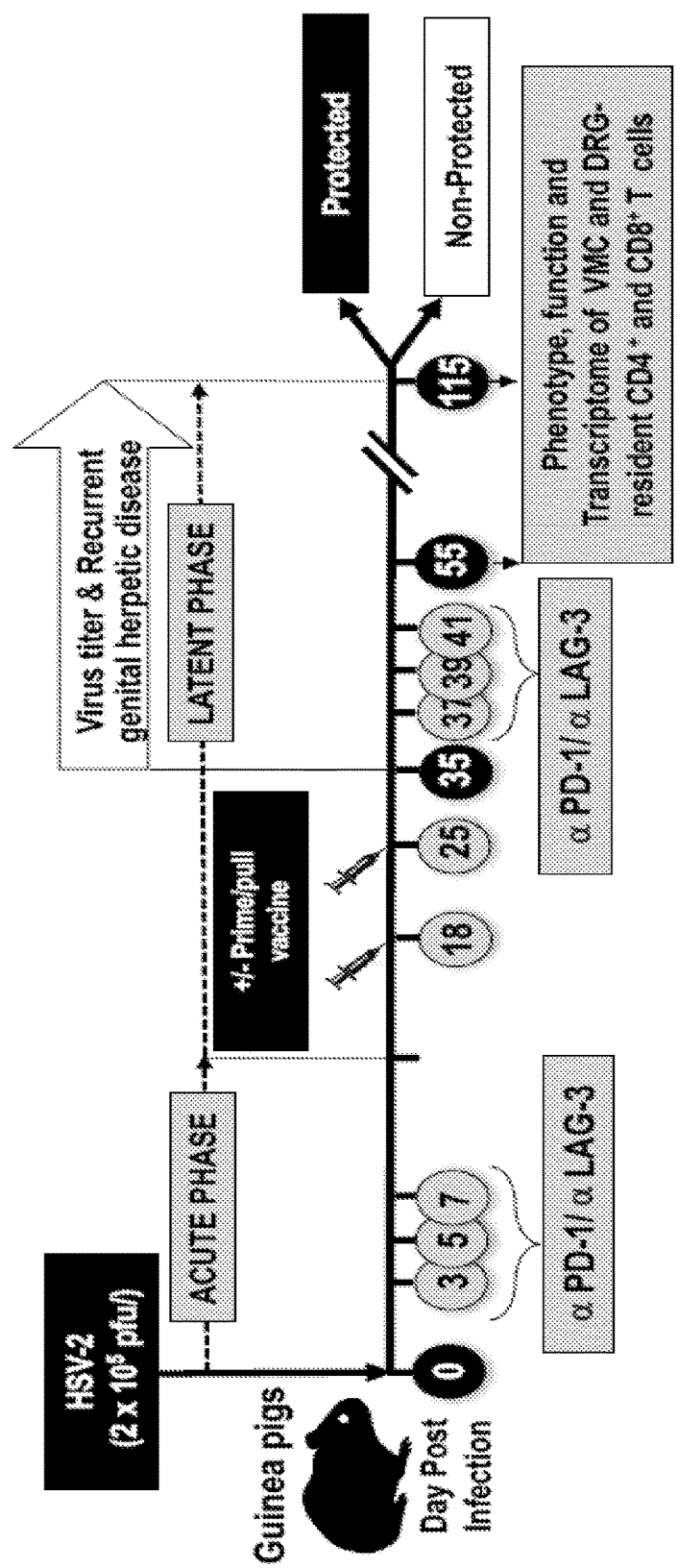
FIG. 20 depicts a time course of prime/pull therapeutic vaccination, immune checkpoint blockade and the immunological and virological assays in HSV-2 infected guinea pigs.

The primary endpoint is to prevent HSV-2 shedding and replication in the VMC. The secondary endpoint is the prevention of recurrent genital herpetic lesions caused by HSV-2 replication in the VMC tissues. These two parameters are followed for 20, 30 and 60-days post-vaccination, as illustrated in FIG. 20. The rate of viral shedding immediately after vaccination is compared to baseline shedding rates before vaccination as well as to the rate of mock-vaccinated controls (Van Wagoner et al., 2018, J Infect Dis, 218: 1890-99). Genital herpes disease and virus shedding are monitored daily by investigators blinded to guinea pig vaccination and treatment and are scored according to a standard 0-4 scale. Mean disease score measured daily for 60-days post-vaccination and cumulative mean lesion severity scores is determined. The number of days with recurrent lesions is determined in vaccinated and control groups.

Latency in DRG

A third endpoint is used to assess the amount of latency in DRG, of vaccinated vs. mock-vaccinated groups, as previously reported (Zhang et al., 2009, Mucosal Immunol, 2: 129-43). DRG are harvested and the expression of immediate early, early, and late genes are quantified by droplet digital RT-PCR (ddRT-PCR), to determine evidence of virus latency in DRG (Zhang et al., 2009, Mucosal Immunol, 2: 129-43; Pieknik et al., 2019, J Virol). Using IHC, will also determine whether tissue-resident CD4+ and CD8+ T cells are co-localized around sensory neurons in DRG. Latency in SSG: Evidence of HSV-2 reactivation in the autonomic sacral sympathetic ganglia (SSG) was recently reported by Dr. Krause's group (Pieknik et al., 2019, J Virol). Besides latency in DRG, latency in autonomic SSG neurons of vaccinated vs. mock-vaccinated groups is determined. In addition, whether tissue-resident CD4+ and CD8+ T cells are co-localized around autonomic neurons in SSG is determined.

Longevity of Protection

Whether protection induced by the lead prime/pull vaccine is long-lasting in the vaccinated guinea pigs (i.e., 12 months after vaccination) is determined.

Ex Vivo Reactivation in Explanted DRG

Figure 21:
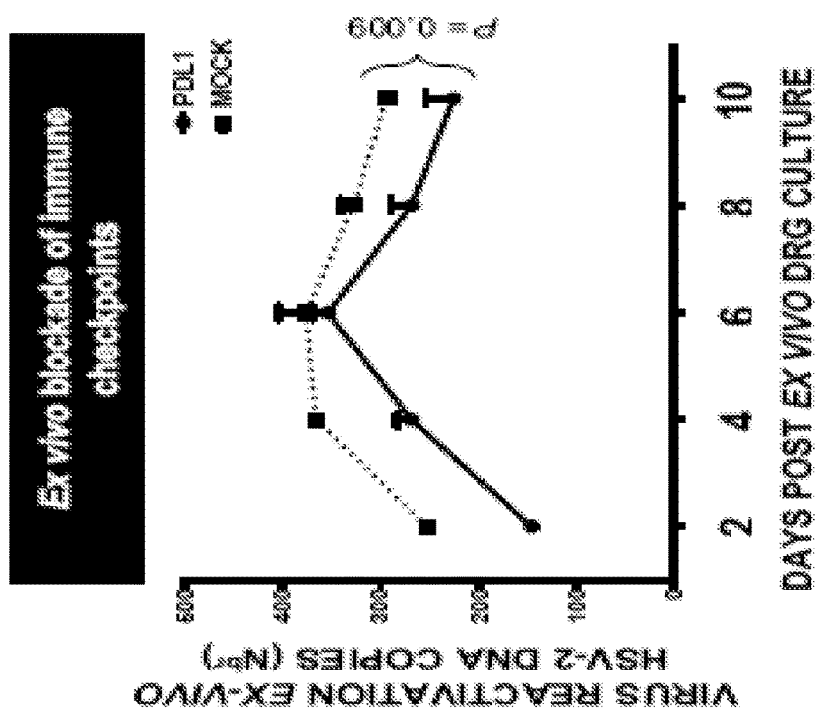
FIG. 21 depicts data demonstrating that blockade of PD-L1 significantly reduces virus reactivation in DRG explants in theHSV-2 infected guinea pig.
Figure 22:
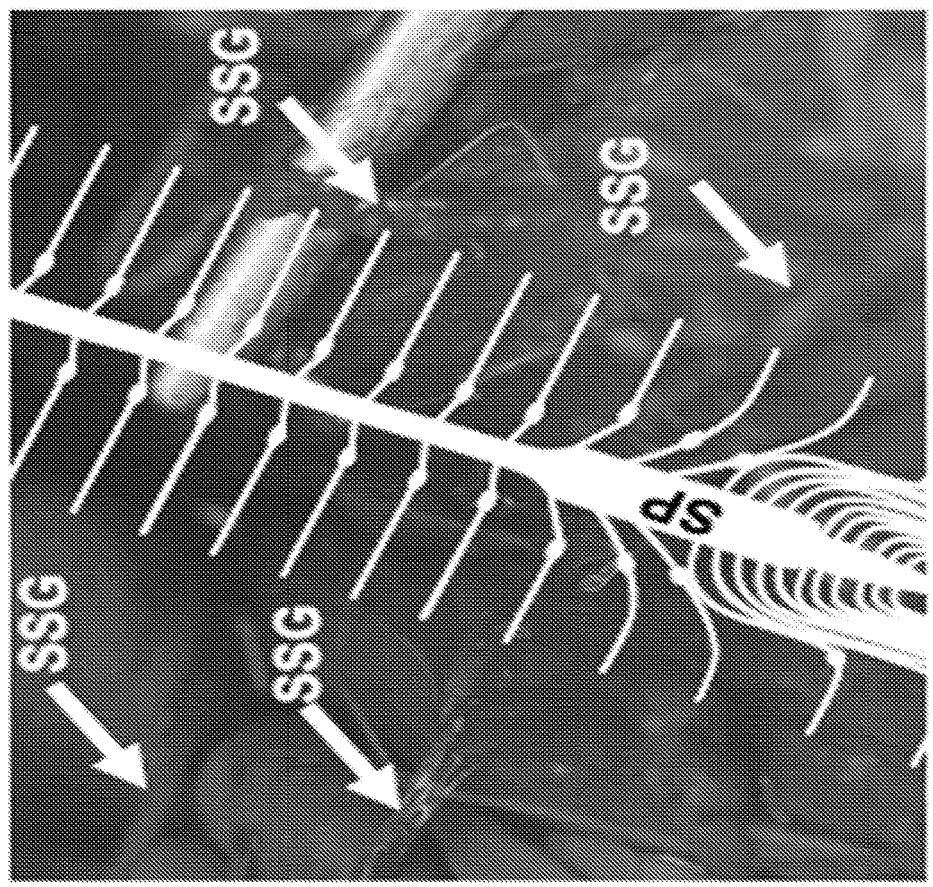
FIG. 22 depicts a diagram demonstrating that blockade of PD-L1 significantly reduces virus reactivation in the sacral sympathetic ganglia (SSG).
Figures 23A, 23B:
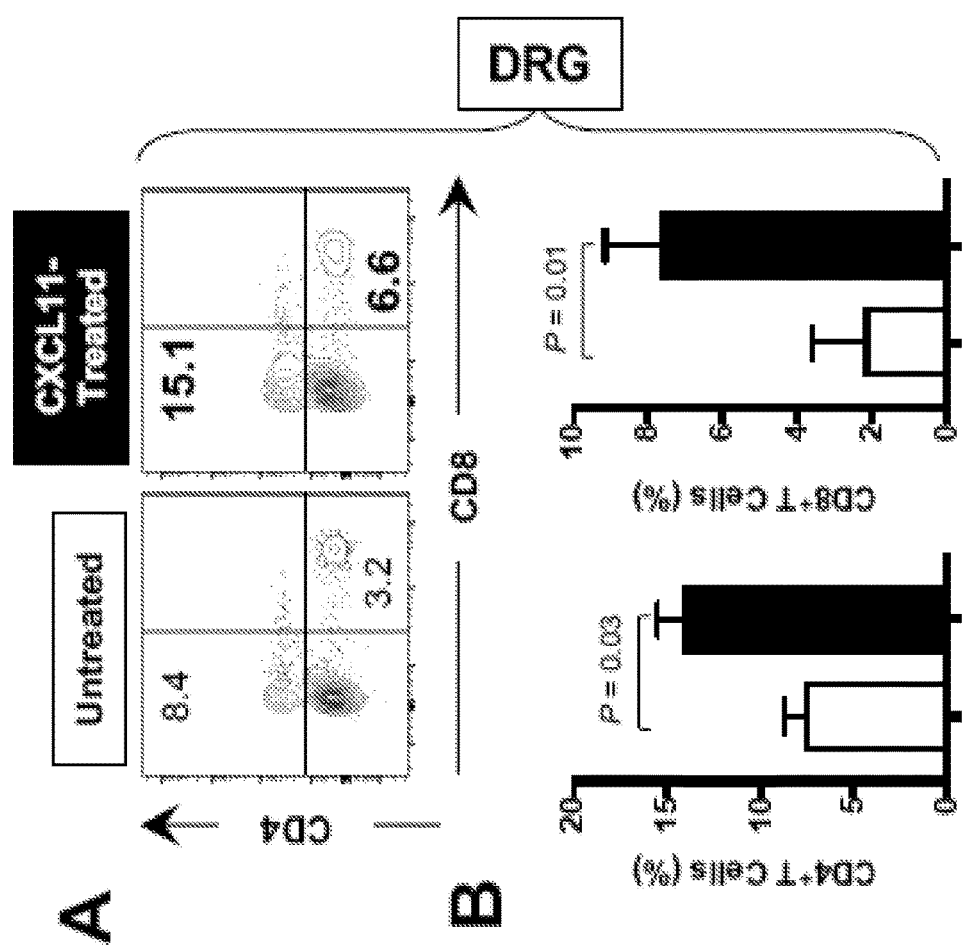
FIG. 23A and FIG. 23B depict exemplary data demonstrating that tissue-resident memory CD4+ and CD8+ T cells increased in the DRG of HSV-2 infected and protected guinea pigs following treatment with CXCL11.
Figure 24:
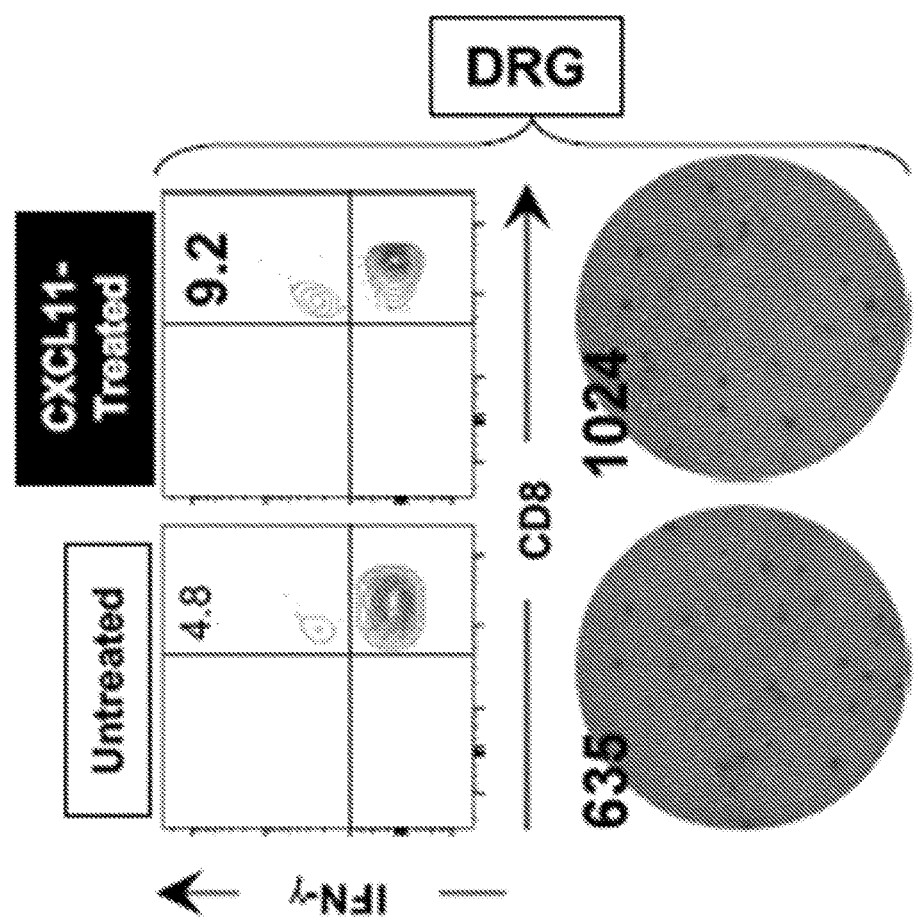
FIG. 24 depicts data demonstrating frequent IFNγ(+) CD8+ T cells were detected in the DRG of HSV-2 infected and protected guinea pigs following treatment with CXCL11.
Figure 25:
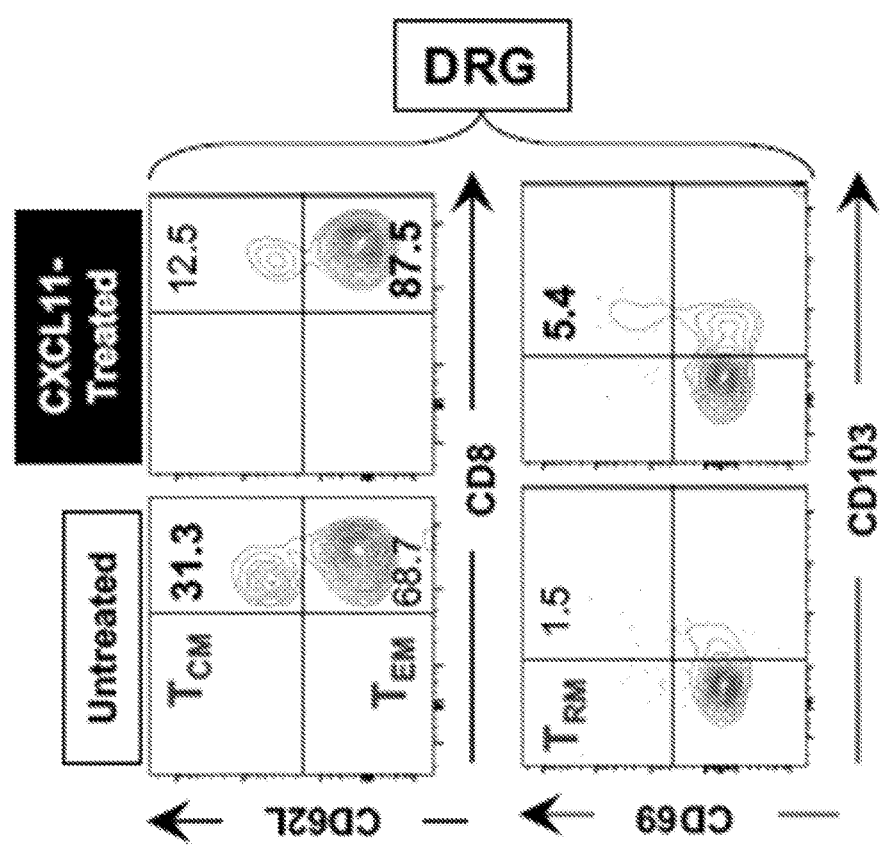
FIG. 25 depicts data demonstrating that tissue-resident memory TRM cells and effector memory TEM cells are increased in the DRG of HSV-2 infected and protected guinea pigs following treatment with CXCL11. Gated on CD44pos cells.

A separate experiment uses latently infected prime/pull vaccinated (n=20) and mock-vaccinated (n=20) guinea pigs to assess the vaccine's effect on viral reactivation, ex vivo, in explanted sensory ganglia as shown in FIG. 21. Seven and 21 days after immunization, DRG are harvested and individually explanted into tissue culture media to permit detection of reactivating virus, as described (Pieknik et al., 2019, J Virol, Khan et al., 2015, J Virol). Immediate early, early, and late gene expression are quantified by droplet digital RT-PCR (ddRT-PCR) for evidence of viral reactivation in the explanted DRG, as recently described (Pieknik et al., 2019, J Virol). The time course of first appearance of the reactivated virus is determined (Khan et al., 2015, J Virol). The % of DRG that reactivate and the kinetics of ex vivo reactivation is compared in the vaccine vs. control groups.

Subtypes of Sensory Neurons

Previous studies in guinea pigs by Dr. Bertke have shown that HSV preferentially replicate and establish latency in different subtypes of sensory neurons (Pieknik et al., 2019, J Virol; Ohashi et al., 2011, J Virol, 85: 3030-2; Bertke et al., 2009, J Virol, 83: 10007-15; Bertke et al., 2011, J Virol, 85: 6669-77; Tang et al., 2011, J Virol, 85: 4501-9; Bertke et al., 2012, PLoS One, 7: e53281; Bertke et al., 2013, J Virol, 87: 6512-6). Therefore, CD4+ and CD8+ T cells are stained together with Fe-A5 mAb (A5+) and isolectin IB4 mAb (KH10+), and whether different subtypes of sensory neurons are co-localized with DRG-resident CD4+ and CD8+ T cells is determined by confocal microscopy. Finally, whether different phenotypes of CD4+ and CD8+ T cells are co-localized with the cell body of sensor neurons vs. the axon ends is determined by localizing T cells around the neuronal cell body in DRG and around the axon termini that extend in VMC.

Immune Checkpoints Blockade

HSV-2 is able to escape T cell surveillance by inducing phenotypic and functional exhaustion of CD4+ and CD8+ T cell responses to successfully coexist with the host and establish long-term latency. An increased frequency of PD-1 and LAG-3-positive CD4+ and CD8+ T cells in the VMC and DRG of HSV-2-infected guinea pigs correlates with a lack of protection (Example 1). The mAbs anti-PDL-1 decreased virus reactivation ex vivo in guinea pigs' DRG explant, suggesting a reversion of T cells exhaustion (FIG. 21). PD-1 and LAG-3 pathway is blocked in vivo following treatment with specific mAbs or peptide inhibitors on days 3, 5, 7 post infection (acute phase) and then on days 37, 39, 41 post infection (latent phase), as was recently demonstrated (FIG. 20). This is performed in groups of guinea pigs with less protective prime/pull vaccine to see whether immune checkpoint would improve protection.

Statistical Analyses

Virological, immunological, transcriptional, and disease parameters are determined in every animal from the same group. A Generalized Estimating Equations (GEE) approach is applied to analyze the Time-Average Difference (TAD) in means of severity scores between the vaccinated groups (Group 1 to Group 18 in FIG. 18) and the negative control groups (Group 19 to Group 32) (Zhang et al., 2013, Comput Stat Data Anal, 58:283-91; Zhang et al., 2018, Contemp Clin Trials, 64:274-80). Without being bound by theory, based on preliminary evidence, it was assumed that a sample of two guinea pigs will develop severe recurrent genital herpes infection or disease, each measured on days 35 to 55 for a total of 20 measurements. This demonstrated that the methods achieve a power of at least 0.90 using a two-sided Wald test from a GEE analysis to test whether the TAD of the vaccinated guinea pigs differs from that of the control guinea pigs by more than 0.40 at a significance level of 0.05.

Protection Against Genital Herpes Infection and Disease

The VP16, VP22, RR1 and/or RR2 prime/pull therapeutic vaccine candidates (Groups 1 to 18 in FIG. 18) significantly reduce the frequency and/or magnitude of virus reactivation form DRG and viral shedding in VMC. No or little HSV-2 DNA is detected in any vaginal swab sample from the best prime/pull vaccinated animals, a result that suggests that viral reactivation and/or shedding is significantly reduced by the prime/pull vaccine. This was also associated with a significant reduction of the frequency recurrent lesion outbreaks, to decrease the total lesion days per animal, and decrease lesion severity scores relative to the protein-based vaccinated counterpart group (n=20) and relative to the mock-vaccinated control group (n=20). The frequency with which prime/pull vaccinated animals shed virus was also reduced as compared to the protein-based vaccinated counterpart groups (Groups 25 to 30 in FIG. 18) and/or mock-vaccinated control (group 32, in FIG. 18). This suggests that a decrease in the number of days with recurrent lesions, lesion severity, and shedding may be due to enhanced antiviral DRG-tissue-resident CD4+ and CD8+ T cells that control reactivation. Thus, VP16, VP22, RR1 and/or RR2 prime/pull vaccine candidates (i.e., Groups 1 to 18 in FIG. 18) decrease viral loads in the DRG as compared to the gD control group (Groups 22 to 24 in FIG. 18). The combination of protein with T-cell attracting chemokines have an advantage over the protein vaccine alone. A reduction in the frequency by which animals shed virus after prime/pull vaccination with at least one of the 18 VP16, VP22, RR1 and/or RR2 prime/pull vaccine candidates suggests that immune responses to that vaccine plays a role in controlling viral reactivation from DRG. A decrease in the number of days with recurrent lesions, lesion severity, and shedding may also be due to an increase in number and function of tissue-resident CD4+ and/or CD8+ T cells that control reactivation in DRG and subsequent viral replication in VMC.

Latency in DRG

At least one prime/pull vaccine decreases the load of latency in this DRG along the spinal column. Evidence of viral reactivation/latency in SSG, as recently reported (Pieknik et al., 2019, J Virol) was confirmed. In addition, a low latency level in the SSG of the vaccinated group (Pieknik et al., 2019, J Virol) was confirmed. At least one lead prime/pull induce protection that lasts up to 12 months after vaccination.

Subtypes of Sensory Neurons

Antiviral DRG tissue-resident CD4+ and CD8+ T cells are localized around KH10 neurons, but not A5 neurons. DRG tissue-resident CD4+ and CD8+ T cells are both co-localized with the cell body of sensory neurons in DRG and the axon ends in VMC.

Immune Checkpoints Blockade

In vivo blockade of PD-1 and LAG-3 immune checkpoints with mAbs and/or peptide inhibitors reduces virus reactivation and improves protection. This suggests a reversion of would-be exhausted antiviral DRG-tissue resident CD4+ and CD8+ T cells that control reactivation, confirming the ex vivo finding (FIG. 21).

Figure 12A:
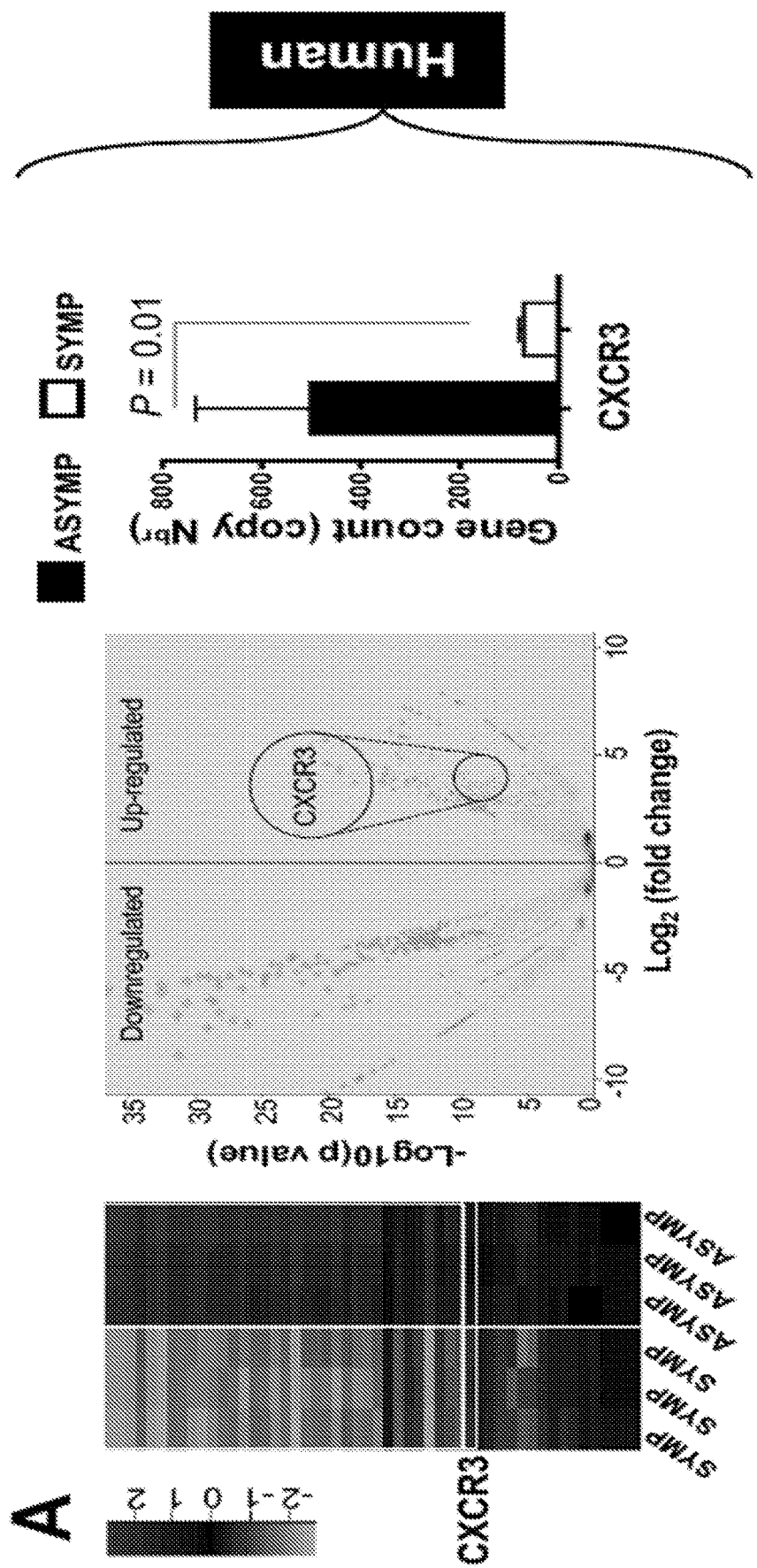
FIG. 12A through FIG. 12F depicts exemplary experimental results demonstrating that frequent HSV-specific tissue-resident CXCR3+CD8+ T cells in healed VMC tissue of protected guinea pigs are associated with stimulation of the CXCL9, CXCL10, CXCL11/CXCR3 axis.
Figures 12B, 12C:
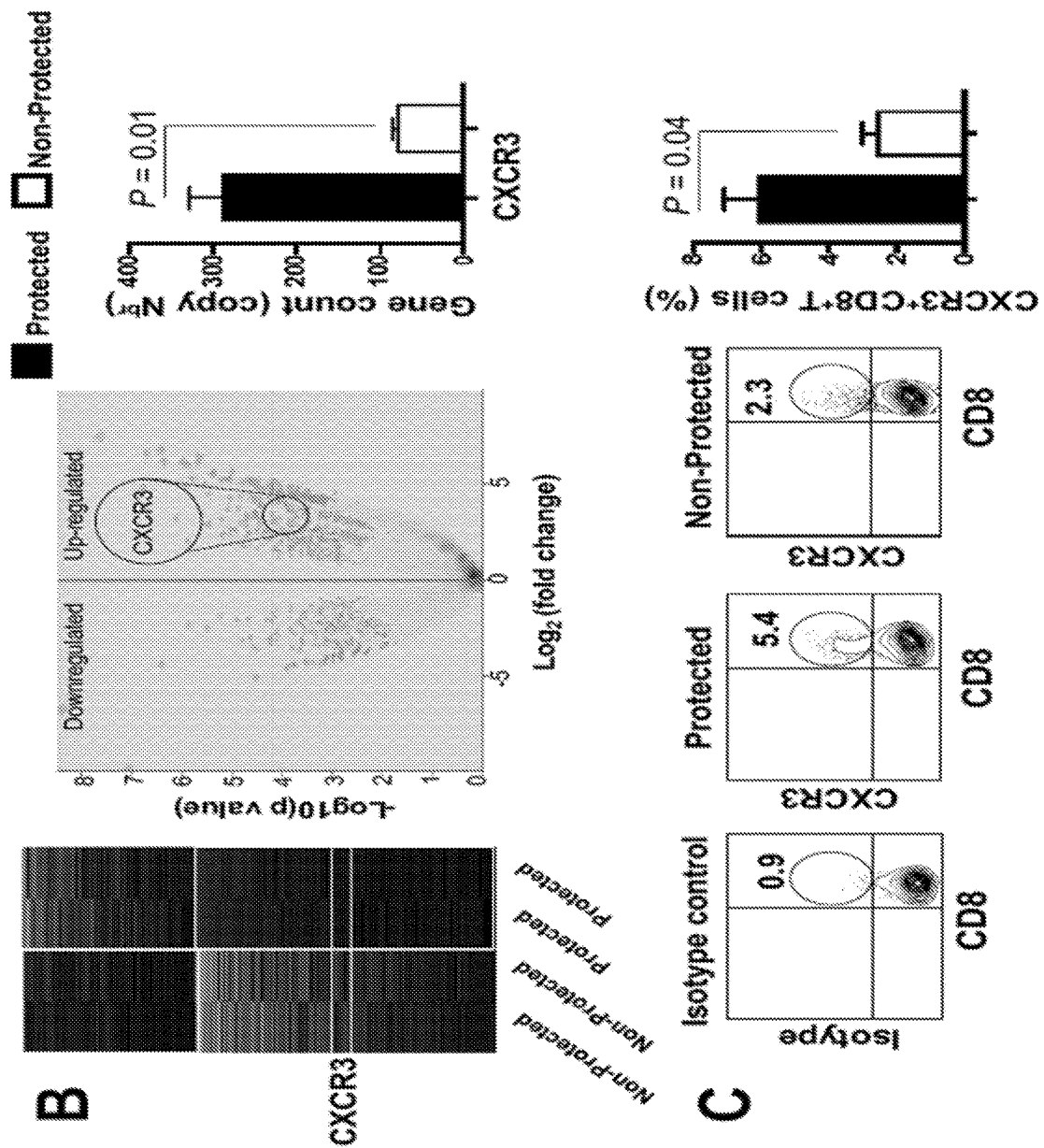
Figures 12D, 12E:
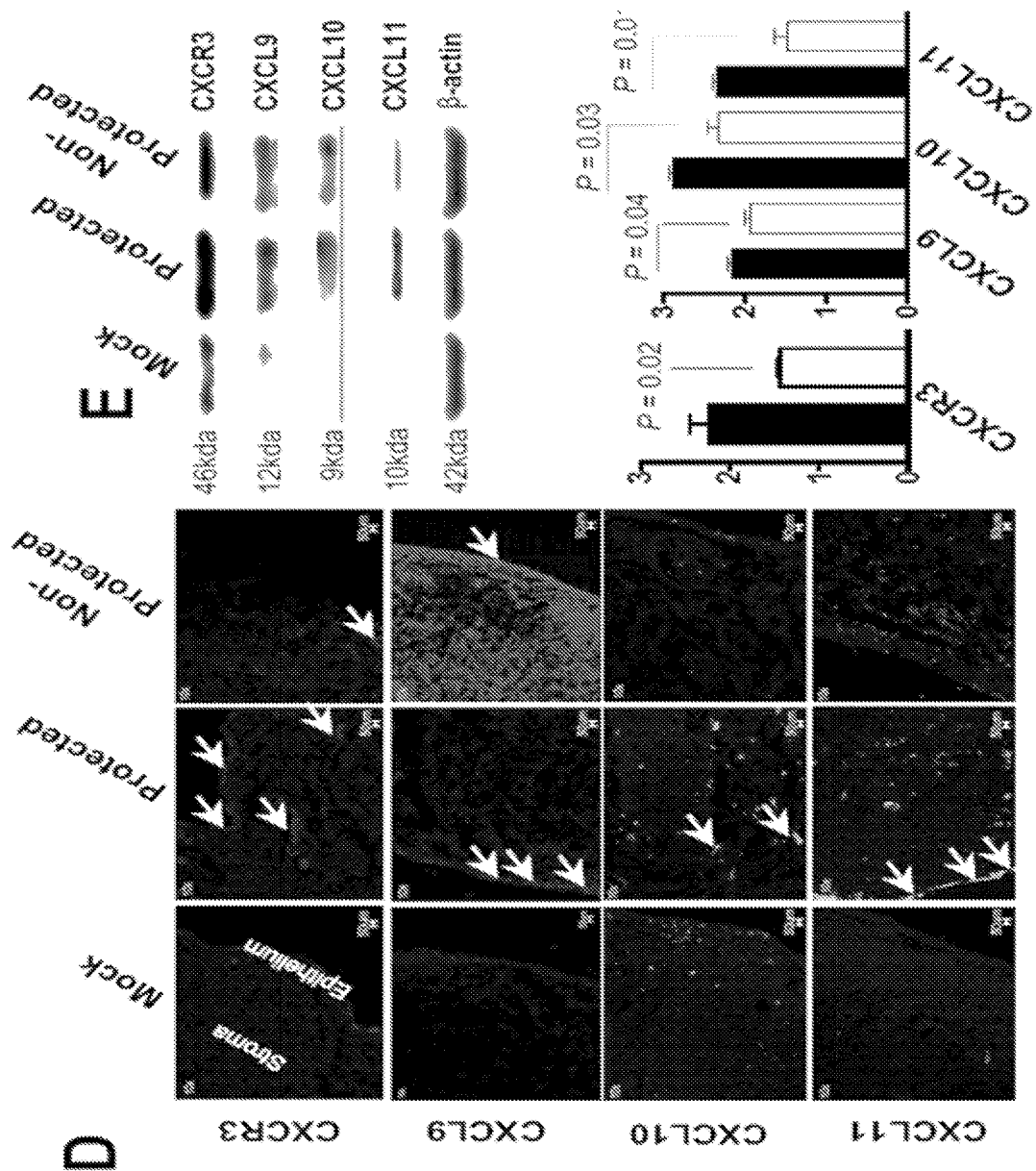
Figure 12F:
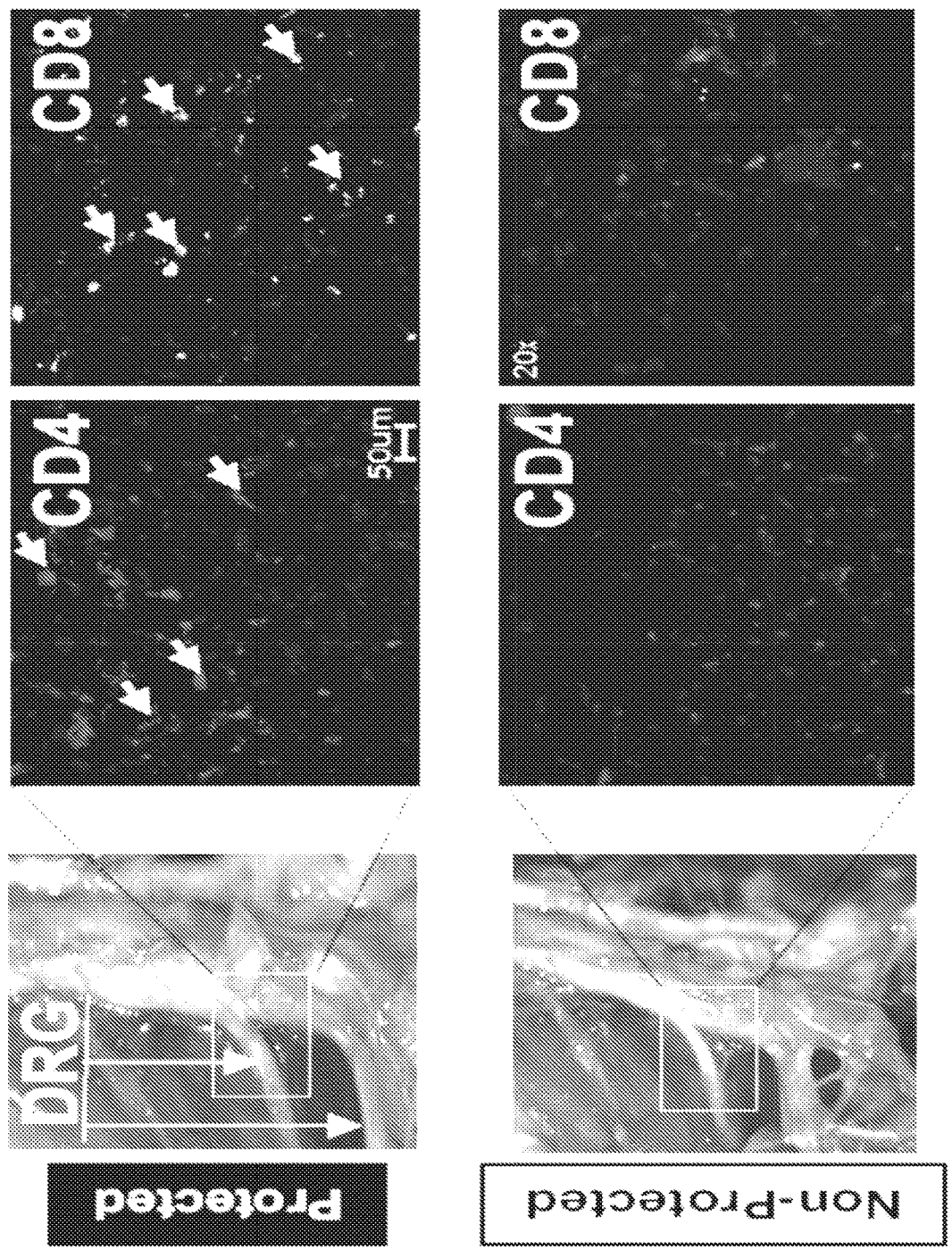
Figure 13:
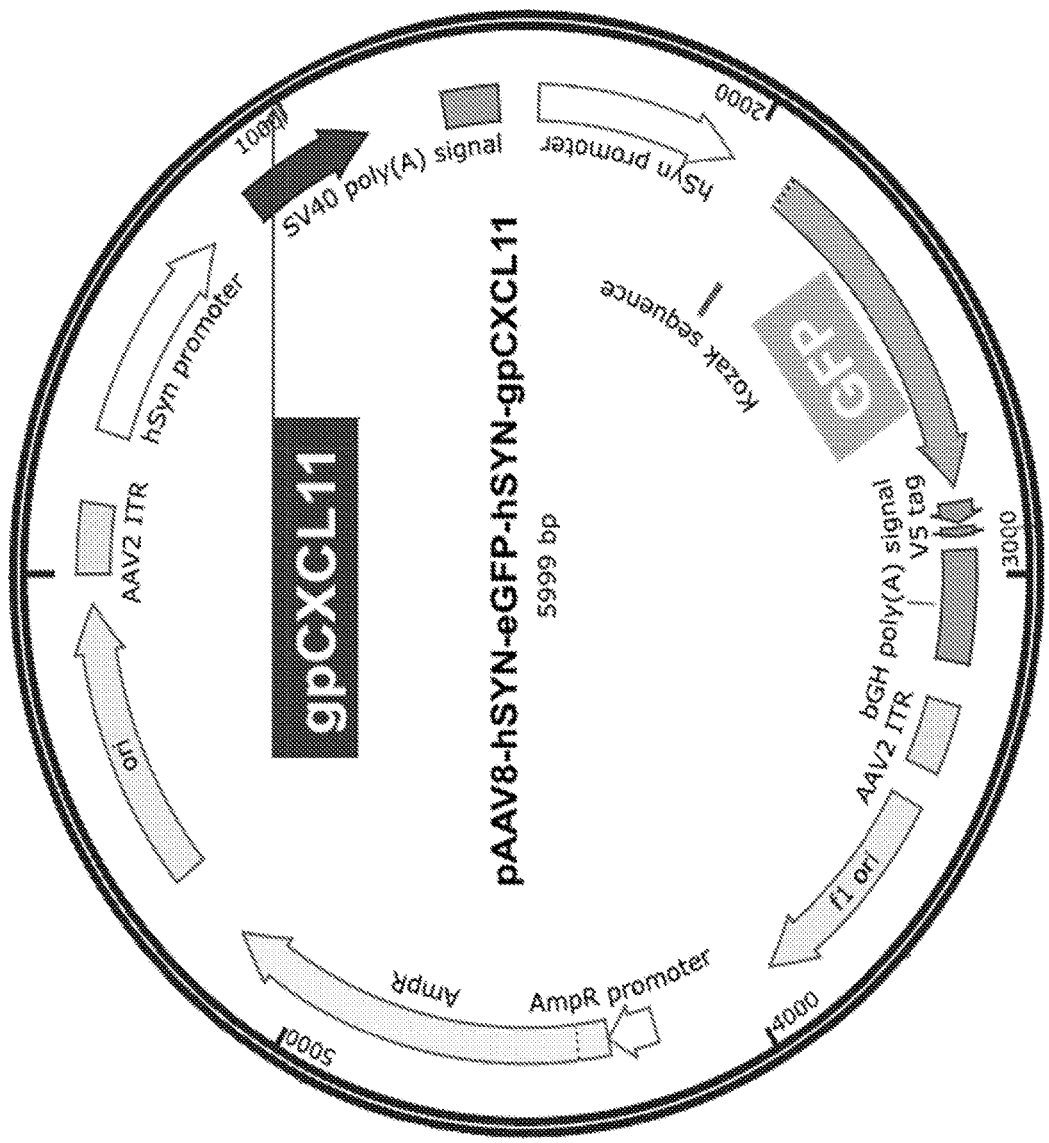
FIG. 13 depicts a diagram of the neurotropic AAV8 expressing the green fluorescent protein (GFP) and the guinea pigs' gpCXCL11 under the neurotropic human synapsin 1 promoter (hSYN). ITR from AAV2 and AAV8 capsid was used for packaging.
Figure 14:
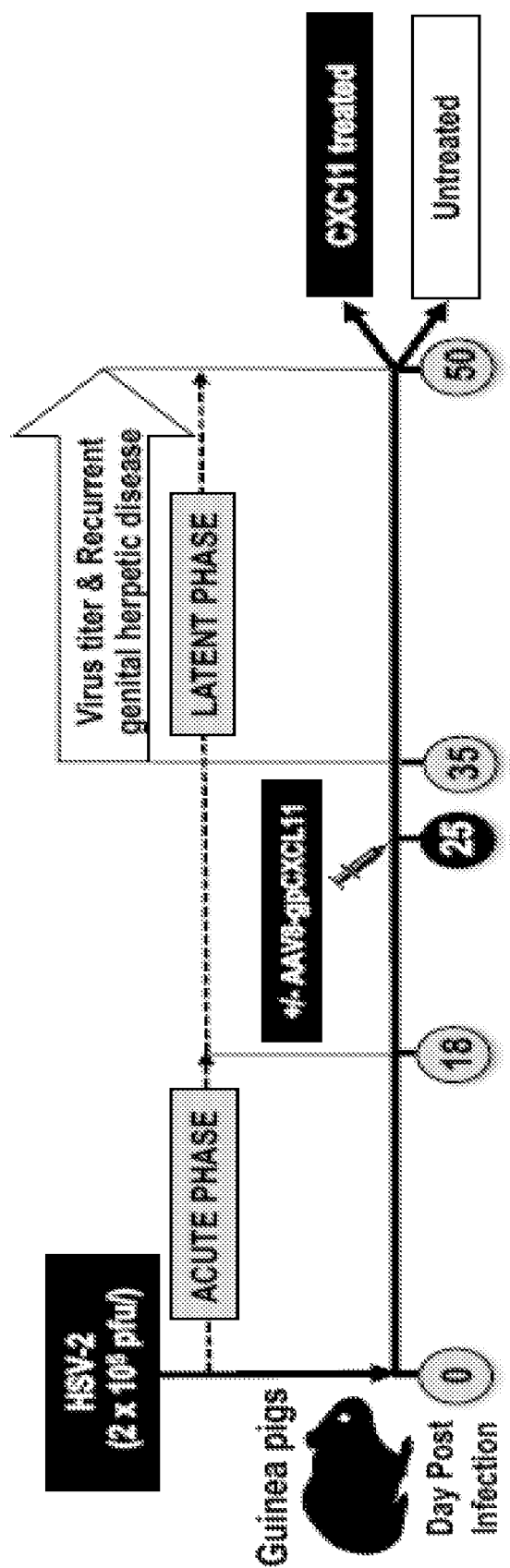
FIG. 14 depicts a diagram for treatment of HSV-2 infected guinea pigs with CXCL11.

Increase in the Number and Function of Antiviral Tissue-Resident CD4+ and CD8+ T Cells Within: (1) DRG (Central Neuronal Immunity); and (2) VMC (Peripheral Epithelial Immunity) Correlates with Protection Against Recurrent Genital Herpes Infection and Disease Dorsal root ganglia (DRG) and vaginal muco-cutaneous (VMC) are the most obvious battlefield sites for the host's B- and T-cells to control recurrent genital herpes. Preliminary phenotypic, functional, and transcriptomic T cell results (obtained in the guinea pig model of recurrent genital herpes revealed that: (1) Increased numbers of CXCR3+ CD4+ and CXCR3+ CD8+ T cells were detected in the VMC and DRG tissues of protected compared to non-protected guinea pigs (FIG. 12F and FIG. 12C); and (2) Similar to HSV-2 VP16-specific CD8+ T cells in HSV-2 infected and asymptomatic women (FIG. 12A), elevated levels of CXCR3 receptor and T-cell attracting CXCL9, CXCL10 and CXCL11 (ligands of CXCR3) were detected in CD8+ T cells from DRG and VMC of HSV-2 infected and protected guinea pigs, at both RNA transcript by RNA-Seq (FIG. 12B), and protein levels by immunostaining (FIG. 12D) and western blot (FIG. 12E), as compared to non-protected guinea pigs. In silico, in vitro, in situ, ex vivo, and in vivo assays are used to shed more light on the relative contribution of the central neuronal T cell immunity (in the DRG) vs. peripheral epithelial T cell immunity (in the VMC) in protection against recurrent genital herpes.

T Cell Correlates of Central Neuronal Protective Immunity were Determined using the Following:

Frequency

The DRG are harvested from groups of protected and non-protected guinea pigs that are sacrificed before and 10, 15, 30, and 90-days post-immunization (n=20/group, FIG. 20). The number and function of HSV-specific memory CD4+ and CD8+ T cells within the DRG, their association with the level of latency and the frequency of virus reactivation from the DRG are determined. The number and % of CXCR3(+)CD4+ and CXCR3(+)CD8+ T cells in DRG is determined by FACS (FIG. 12F, FIG. 17, FIG. 21, FIG. 23 and FIG. 25). The frequency of CXCR3(+)CD4+ and CXCR3(+)CD8+ T cells in HSV-2 DNAPOS vs. HSV-2 DNANEG DRG is determined, as has been performed in human TG (van Velzen et al., 2013, PLoS Pathog, 9:e1003547; Theil et al., 2003, Am J Pathol. 163:2179-84; Theil et al., 2003, Ann Neurol, 54:678-82). Expression levels of CD69, CD103 (known as integrin $\alpha 4\beta 7$), CCR7, CD62L (also known as L-selectin), T-bet, and Eomes are evaluated.

The prime/pull vaccine candidates "pull" more protective local CD4+ and CD8+ T cells into the DRG compared to HSV-DL5-29-vaccine and to mock-vaccine. There are increased numbers and % of CXCR3(+)CD4+ and CXCR3 (+)CD8+ T cells in DRG of prime/pull vaccinated protected animals consistent with mobility and attraction by local CXCL9, CXCL10 and CXCL11 chemokines. This confirms the results that human ganglia that show CD8+ T cells express high levels of both CXCR3 and CCR1(119, 128). Frequent CXCR3(+)CD4+ and CXCR3(+)CD8+ T cells are present in HSV-2 DNAPOS vs. HSV-2 DNANEG DRG and SSG, suggesting attraction of HSV-specific T cells to infected ganglia. Increased expression levels of CD69 and CD103, and decreased expression of receptors and transcription factors required for tissue egress and blood recirculation, such as CCR7, CD62L, S1PR1, KLRG1, T-bet, and Eomes, on CD4+ and CD8+ T cells in DRG of prime/pull infected animals, suggests molecular involvement in permanent retention of CD4+ and CD8+ T cells in peripheral DRG tissues.

Location

The anatomic localization of sensory ganglia-resident CD4+ and CD8+ T cells was defined relative to individual HSV-infected neurons. Imaging was used to determine whether different subtypes of sensory neurons (i.e., A5+ and KH10+) are co-localized and targeted by CD4+ and CD8+ T cells.

CD4+ and CD8+ T cells in prime/pull vaccinated protected guinea pigs, but not in non-protected guinea pigs, selectively cluster around both ends of infected neurons. This leads to efficient inhibition of virus reactivation from the infected neurons and a greater reduction in HSV shedding seen in vaccinated and protected guinea pigs. Such a result indicates that prime/pull vaccination delivers T-cell attracting chemokines CXCL9, CXC10 and CXCL11 in infected neurons, and does "pull" vaccine-induced T cells closer to infected neurons, where they can react rapidly and abort any attempts at virus reactivation. Further, antiviral CD4+ and CD8+ T cells are co-localized around KH10 neurons, but not A5 neurons, as previously shown in mice.

Function

Functional properties of DRG-resident CD4+ and CD8+ T cells in prime/pull-vaccinated guinea pigs that show rapid and effective peripheral control of HSV-2 with low shedding and fast-healing tissue are determined. These functional properties are compared to those of mock-vaccinated and non-protected guinea pigs. Chemokine levels (both mRNA and protein) are determined in DRG using RT-PCR and Luminex assays (Zhang et al., 2009, Mucosal Immunol, 2:129-43; Theil et al., 2003, Ann Neurol, 54:678-82; Derfuss et al., 2007, Brain Pathol, 17:389-98; Hufner et al., 2006, J Neuropathol Exp Neurol, 65:1022-30; Theil et al., 2001, Brain Pathol, 11:408-13; Liu et al., 1996, J Virol, 70:264-71). HSV-specific CD4+ and CD8+ T cell function are measured by IFN-γ ELISPOT assays. CD4+ and CD8+ T cells' cytotoxic activity are analyzed by CD107a/b degranulation assays (Dervillez et al., 2013, J Immunol, 191:5124-38). Tissue-derived signals, including TNF-α, TGFβ, IL-15, and IL-33, which support CD4+ and CD8+ TRM differentiation and survival in local tissue are also evaluated (Mackay et al., 2013, Nat Immunol, 14:1294-301; Mackay et al., 2015, Immunity, 43:1101-11; Mami-Chouaib et al., 2018, J Immunother Cancer. (2018); 6: 87; Tian et al., 2019, Oncoimmunology, 8:e1538440).

High effector function of DRG-resident CD4+ and CD8+ TRM cells, including increased expression of cytotoxic CD107a/b granules, antiviral IFN-γ and TNF-α cytokines, and T cell-attracting CXCL9, CXCL10 and CXCL11 chemokines are associated with effective control of HSV-2 reactivation from DRG/SSG. An increased number of HSV-specific IFN-γ-producing CD4+ and CD8+ T cells, and an increased number of CD107a/b+CD4+ and CD107a/b+ CD8+ cytotoxic T cells are identified in DRG/SSG of prime/pull vaccinated animals. Expression of in situ RNA transcripts of Granzyme (GzmA, GzmB and GzmK) and perforin markers for cytotoxic function, IFN-γ, and CXCL9, CXCL10, and CXCL11 chemokines as representative genes for T cell-attracting factors are measured using an ultrasensitive FISH assay. Finally, upregulation of tissue-derived protective factors, including TGF-β, TNF-α, IL-15, and IL-33, which have been implicated in the process of TRM differentiation and survival in peripheral tissues (Mackay et al., 2013, Nat Immunol, 14:1294-301; Mackay et al., 2015, Immunity, 43:1101-11; Mami-Chouaib et al., 2018, J Immunother Cancer. (2018); 6: 87; Tian et al., 2019, Oncoimmunology, 8:e1538440). An increase in the CD69, CD103, CD101, and CD49a receptors in the prime/pull vaccinated and protected animals are identified, which are implicated in sequestration of TRM cells in infected tissues (Woon et al., 2016, PLoS Pathog, 12:e1005799).

Single Cell scRNA-Seq

Single-cell RNA sequencing (scRNA-Seq) in protected and non-protected guinea pigs, is performed to identify biomarkers predictive of protection and to define T cell pathways in sensory ganglia. DRG-resident HSV-specific CD4+ and CD8+ T cells are profiled longitudinally as they respond to vaccine and virus reactivation. On days 4, 7, 30, and 60 after vaccination of HSV-2-infected guinea pigs, CD4+ and CD8+ T cells are sorted from the DRG and VMC. Isolation of single-cell RNA and cDNA synthesis is performed using the Fluidigm C1 Single-cell RNA sequencing integrated fluidic circuit and C1 Single-Cell Auto Prep System. Post-scRNA-Seq, reads are mapped to the guinea pig genome (Cavpor3.0) using the spliced transcript aligner STAR35.

These results to provide important insights into the molecular mechanisms of antiviral central neuronal T cell immunity in DRG/SSG. In addition, biomarkers predictive of protection and that define immune pathways are identified.

Correlation

Correlation between HSV-2 reactivation (virus shedding in genital tract) and recurrent genital herpetic disease with number and function of local CD4+ and CD8+ TRM cells in DRG and SSG is determined. CD4+ and CD8+ T cells in DRG of prime/pull vaccinated animals, correlates with elevated production of cytolytic granules, increased expression of antiviral cytokine/chemokine, and onsite proliferation. One of the hallmark features of memory CD4+ and CD8+ TRM cells is their ability to perform immune surveillance and rapid clearance of re-encountered virus. Thus, more antiviral effector CD4+ and CD8+ TRM cells retained in latently-infected DRG of prime/pull vaccinated animals should interfere with "attempts" or clear "ongoing" virus reactivations in neurons of DRG. This translates into a reduction in subsequent virus shedding in the VMC and less recurrent genital herpes disease. CD4+ and CD8+ TRM cells greatly outnumber recirculating TRM and TCM cells within non-lymphoid DRG and VMC tissues of protected guinea pigs (Steinert et al., 2015, Cell, 161:737-49). These results (1) reveal tissue compartmentalization as a major determining factor for immune-mediated protection against recurrent herpes; and (2) suggest that the temporal limitation on access of antiviral CD4+ and CD8+ T cells into the immunologically restricted DRG compartment is overcome with the prime/pull vaccine. T cell immunity in the autonomic ganglia has an important role in controlling viral reactivation recurrent disease.

Ex Vivo Depletion of CD4+ and CD8+ T Cells

Ex vivo T cell depletion in explanted DRG: HSV-2 can be transmitted asymptomatically in the absence of genital lesions, allowing efficient virus spread amongst the general population(1). Similar to humans, in the guinea pig model, recurrent genital lesions arise from spontaneous reactivation of latent virus in sensory neurons cell bodies of dorsal root ganglia (DRG) (Example 1). However, HSV-2 has also recently been found to reactivate from latently infected autonomic SSG(6). This suggests that, in addition to sensory ganglia, HSV-2 reactivation from autonomic ganglia may also contribute to viral shedding in the genital tract and lead to recurrent genital herpes. However, local immune responses may also decrease local virus replication in the VMC tissue. HSV-2 reactivation is assessed directly ex vivo by explanting guinea pigs' DRG-induced reactivation (FIG. 21). DRG from latently infected prime/pull vaccinated guinea pigs are harvested at 7 and 21 days post-immunization. Ex vivo explant DRG are cultured as is, or depleted ex vivo of CD4+ and/or CD8+ T cells as described (Khan et al., 2015, J Virol). Explant ganglia from the animals at 10, 15, 30, and 90 days post-infection during the latent phase of infection are used for immunostaining of CXCR3(+)CD4+ and CXCR3(+)CD8+ T cells and to determine their co-localization with infected neurons in DRG.

The prime/pull vaccine reduces HSV-2 reactivation in the ex vivo explant DRG-induced model. Ex vivo depletion of CD4+ and/or CD8+ T cells increases virus reactivation in explanted DRG.

In Vivo Depletion of CD4+ and CD8+ T Cells

To assess the involvement of CD4+ and CD8+ T cell subsets in the protection induced by a candidate vaccine, in vivo depletion of either CD4+ or CD8+ T cells using specific mAbs injected intravenously are performed in infected guinea pigs before and after each immunization. CD4+ or CD8+ T cells not only infiltrate to the sites of infection, but also persist in DRG and VMC for prolonged time periods after viral clearance. In vivo depletion of CD4+ and/or CD8+ T cells abrogated the central and/or peripheral immunity induced by the prime/pull vaccine.

T Cell Correlates of Peripheral Epithelial Protective Immunity were Determined using the Following:

Frequency

The frequency of CD4+ and CD8+ T cells that reside in the VMC of protected vs. non-protected guinea pigs was quantified and 10, 15, 30, and 90 days post-immunization (n=20/group, FIG. 20). The location of CD4+ and CD8+ T cells are determined at the dermal-epidermal junction (DEJ) of the epidermis.

At least 1 out of the 18 prime/pull vaccine candidates in Table 1 to "pull" more protective local CD4+ and CD8+ T cells into the VMC. A high number of CD4+ and CD8+ T cells were at the dermal-epidermal junction (DEJ) of protected guinea pigs with no lesions.

Function

Using the same markers as for central T cell immunity in DRG/SSG as above, the function and exhaustion of dermal-epidermal junction tissue-resident memory CD4+ and CD8+ TRM cells was determined in vaccinated and control animals. The longevity of tissue-resident CD4+ and CD8+ T cell responses was determined for up to 12 months.

Guinea pigs with higher density of functional CD4+ and CD8+ T cells in the epidermis have a lower shedding rate. Increased expression of cytotoxic CD107a/b granules, anti-viral IFN-γ and TNF-α cytokines are associated with low shedding rate. At least one prime/pull vaccine candidate induced tissue-resident CD4+ and CD8+ T cell-dependent protection that lasts up to 12 months after vaccination.

Single Cell scRNA-Seq

Before and 10, 15, 30, and 90 days post-immunization, CD4+ and CD8+ TRM cells were sorted from the VMC. Similar to DRG/SG, scRNA-Seq was used to identify biomarkers predictive of protection in the VMC and to define T cell pathways in VMC of protected animals and subsequently perform scRNA-Seq for DRG/SSG. T cell pathways were identified in the VMC epithelium barrier that associated with peripheral epithelial immunity.

Correlation

The number of CD4+ and CD8+ T cells was correlated with rates and level of virus shedding and recurrent disease severity. The association of the HSV-specific CD4+ and CD8+ T cell responses, the frequency of virus shedding and replication in the VMC epithelial cells, and subsequent recurrent genital herpes was determined. In addition, the longevity of tissue-resident CD4+ and CD8+ T cell responses that are associated with protection were determined for up to 12 months after vaccination. Prime/pull vaccinated and protected guinea pigs present low virus shedding rates and healed VMC tissue correlates with frequent VMC-resident CD4+ and CD8+ T cells.

Tissue-Resident vs. Circulating Memory T Cells in Protection

It was determined whether increased number of T cells in VMC and DRG was due to: (1) a boost of a pre-existing pool of tissue-resident TRM cells; or (2) circulating memory T cells (TCM and TEM) migrating toward T-cell attracting chemokines delivered locally. TCM, TEM, and TRM were detected in guinea pig VMC and DRG. A separate group of prime/pull vaccinated latently infected guinea pigs (n=20) was treated with the fungal metabolite fingolimod FTY720, a CCR7 chemokine antagonist that blocks T-cell migration from circulation and regional lymph nodes to home in to peripheral inflamed tissues, such as VMC and DRG (Johnson et al., 2010, Clin Immunol, 137:15-20; Pinschewer et al., 2000, J Immunol, 164:5761-70; Johnson et al., 2010, Arch Neurol, 67:1449-55). FTY720 was given IP, 5 times, 1 day before AAV8-chemokines treatment and then every other day.

FTY720 treatment significantly reduced the % and Nbr of CD4+ and CD8+ T cells within the DRG and VMC and abrogated protection induced by the prime/pull vaccine. This suggests the importance of circulating T cells (i.e. TCM and TEM) migrating toward the T-cell-attracting chemokines delivered locally in infected DRG and VMC.

Neutralizing Antibodies

The prime/pull vaccine induced neutralizing antibodies (in addition to T cells). Neutralizing antibodies from serum (IgG) and vaginal washes (IgA) also correlated with protection, as was reported (Example 1).

Mathematical Modeling

Mathematical modeling was used to shed light the relative contribution of the peripheral epithelial immunity vs. central neuronal immunity in protection. Dynamical mathematical models were designed to identify the relative contribution of the peripheral epithelial T cell immunity (in the VMC) vs. central neuronal T cell immunity (in the DRG) in the protection against recurrent genital herpes The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a herpes simplex type I (HSV1) or herpes simplex virus 2 (HSV2) related infection in a subject, the method comprising contacting a cell of the subject with a therapeutically effective amount of a non-viral composition selected from the group consisting of:
    a) a composition comprising a combination of at least two HSV antigens selected from the group consisting of RR1, RR2, VP22, UL25, VP16, VP13/14, and VP11/12; and
    b) a composition comprising at least one recombinant nucleic acid molecule encoding a combination of-at least two HSV antigens selected from the group consisting of RR1, RR2, VP22, UL25, VP16, VP13/14, and VP11/12.

2. The method of claim 1, wherein the composition is administered as a prime vaccine in a prime and pull treatment regimen.

3. The method of claim 2, wherein the pull treatment of the prime and pull treatment regimen comprises administration of at least one cytokine selected from the group consisting of CXCL9, CXCL10 and CXCL11.

4. The method of claim 1, wherein the herpesvirus-associated disorder is selected from the group consisting of labial herpes, genital herpes, primary herpes infection with a human alpha-herpesvirus, Bell's palsy, vestibular neuritis, and herpetic neuralgia.

5. The method of claim 1, wherein the subject has an asymptomatic herpesvirus infection.

6. The method of claim 1, wherein the composition comprises a combination of an HSV RR2 antigen and at least one additional HSV antigen.

7. The method of claim 6, wherein the at least one additional HSV antigen is selected from the group consisting of RR1, VP22, UL25, VP16, VP13/14, and VP11/12.

8. The method of claim 1, wherein the composition comprises at least one recombinant nucleic acid molecule encoding a combination of an HSV RR2 antigen at least one additional HSV antigen.

9. The method of claim 8, wherein the at least one additional HSV antigen is selected from the group consisting of RR1, VP22, UL25, VP16, VP13/14, and VP11/12.

10. The method of claim 1, wherein the composition further comprises at least one additional HSV antigen.

11. The method of claim 10, wherein the at least one additional HSV antigen is selected from the group consisting of gD, RR1, RR2, VP22, gB, VP16, VP13/14, VP11/12 and UL25.

12. The method of claim 10, wherein the at least one additional HSV antigen is selected from the group consisting of gD and gB.

* * * * *

UNITED STATES PATENT AND TRADEMARK OFFICE
CERTIFICATE OF CORRECTION

| | |
|---|---|
| PATENT NO. | : 11,213,582 B2 |
| APPLICATION NO. | : 16/535534 |
| DATED | : January 4, 2022 |
| INVENTOR(S) | : Lbachir BenMohamed |

It is certified that error appears in the above-identified patent and that said Letters Patent is hereby corrected as shown below:

In the Specification

Column 1 Line 6 should read as follows:
STATEMENT REGARDING FEDERALLY SPONSORED RESEARCH OR DEVELOPMENT
This invention was made with government support under Grant No. 1R01AI150091-01 and 1R21AI147499-01 awarded by the National Institutes of Health (NIH). The government has certain rights in the invention.

Signed and Sealed this
Fourteenth Day of February, 2023

*Katherine Kelly Vidal*

Katherine Kelly Vidal
*Director of the United States Patent and Trademark Office*